(12) United States Patent
Lee et al.

(10) Patent No.: US 7,692,060 B2
(45) Date of Patent: Apr. 6, 2010

(54) GENES THAT ALTER CAPACITY TO ACCUMULATE HEAVY METALS AND SALTS OR RESISTANCE TO HEAVY METALS, SALTS OR DROUGHT, AND TRANSFORMANTS EXPRESSING THE GENES

(75) Inventors: Young-Sook Lee, Pohang (KR);
Won-Yong Song, Pohang (KR);
Do-Young Kim, Pohang (KR);
Dong-Hwan Shim, Pohang (KR);
Byeong-Wook Jeon, Pohang (KR)

(73) Assignee: Postech Academy - Industry Foundation, Pohang (KR)

( * ) Notice: Subject to any disclaimer, the term of this patent is extended or adjusted under 35 U.S.C. 154(b) by 0 days.

(21) Appl. No.: 11/833,226

(22) Filed: Aug. 2, 2007

(65) Prior Publication Data

US 2008/0127366 A1 May 29, 2008

(30) Foreign Application Priority Data

Nov. 28, 2006 (KR) .................... 10-2006-0118652

(51) Int. Cl.
*A01H 5/00* (2006.01)
*C12N 15/09* (2006.01)
*C12N 15/82* (2006.01)
*C12N 15/63* (2006.01)
*A01H 1/00* (2006.01)
(52) U.S. Cl. .................... 800/278; 800/298; 800/295; 800/306; 800/314; 800/317.2; 800/317.3; 800/323.1; 435/468; 435/320.1
(58) Field of Classification Search .................... None
See application file for complete search history.

(56) References Cited

U.S. PATENT DOCUMENTS

| | | | |
|---|---|---|---|
| 5,846,821 | A | 12/1998 | Guerinot et al. |
| 5,927,005 | A | 7/1999 | Gardea-Torresdey et al. |
| 7,173,163 | B2 | 2/2007 | Lee et al. |
| 2005/0091709 | A1 | 4/2005 | Song et al. |
| 2006/0230468 | A1 | 10/2006 | Lee et al. |

FOREIGN PATENT DOCUMENTS

| | | |
|---|---|---|
| KR | 10-2002-0077832 | 10/2002 |
| KR | 10-2002-0077832 A | 10/2002 |
| KR | 10-2003-031867 A | 4/2003 |
| KR | 10-2005-0023044 | 3/2005 |
| WO | WO 03/033705 A1 | 4/2003 |

OTHER PUBLICATIONS

Lee et al. (Plant Physiology, 138:827-836, 2005).*
Federspiel et al. (NCBI, GenBank Accession No. AC007258, Published Oct. 30, 2002).*
Kobae et al. (Plant Cell Physiol., 47:309-318, 2006).*
van den Brule et al. (Planta, 216:95-106, 2002).*
Crouzet et al. (FEBS Letters 580:1123-1130, 2006).*
Thornton et al. (Nature structural Biology, structural genomics supplement, Nov. 2000).*
Keskin et al. (Protein Science, 13:1043-1055, 2004).*
Guo et al. (PNAS, 101: 9205-9210, 2004).*
Wells (Biochemistry 29:8509-8517, 1990).*
Ngo et al., (The Protein Folding Problem and Tertiary Structure Prediction, K. Merz., and S. Le Grand (eds.) pp. 492-495, 1994).*
Crouzet et al. FEBS Letters 580:1123-1130, 2006.*
Guo et al. PNAS, 101: 9205-9210, 2004.*
Lee et al. Plant Physiology, 138:827-836, 2005.*
Federspiel et al. NCBI, GenBank Accession No. AC007258, Published Oct. 30, 2002.*
Van den Brule et al. Planta, 216:95-106, 2002.*
Keskin et al. Protein Science, 13:1043-1055, 2004).*
Thornton et al. Nature structural Biology, structural genomics supplement, Nov. 2000.*
Wells. Biochemistry 29:8509-8517, 1990.*
Ngo et al. The Protein Folding Problem and Tertiary Structure Prediction, K. Merz., and S. Le Grand (eds.) pp. 492-495, 1994).*
Entry DQ323065 for Triticum aestivum cadmium tolerance factor mRNA from NCBI Nucleotide Database (www.ncbi.nlm.nih.gov/entrez); record dated Jan. 2, 2006; document printed Aug. 28, 2007.
S. Park et al., "A wheat gene *TaTM20* enhances cadmium tolerance when expressed in baker's yeast and Arabidopsis," presented at ASPB Conference held at Pohang University of Science and Technology, Republic of Korea, Aug. 4-9, 2006.
Article—Phytoremediation: A Novel Strategy for the Removal of Toxic Metals from the Environment Using Plants; David E. Salt, et al.; Biotechnology vol. 13, May 1995; pp. 468-474.
Article—Phytoremediation of metals: using plants to remove pollutants from the environment; Ilya Raskin, et al; Current Op. in Biotechnology, 1997, 8:221-226.
Article—Heavy metal accumulation and tolerance in British populations of the metallophyte *Thlaspi caerulescens* J.&C. Presl (Brassicaceae); A. J. M. Baker, et al; New Phytol. (1994); 127:61-68.
Article—Expression of Arabidopsis *CAX2* in Tobacco. Altered Metal Accumulation and Increased Manganese Tolerance; Kendal D. Hirschi, et al; Plant Physiology, Sep. 2000, vol. 124, pp. 125-133.
Article—Enhanced metabolism of halogenated hydrocarbons in transgenic plants containing mammalian cytochrome P450 2E1; Sharon Lafferty Doty, et al; PNAS Jun. 6, 2000, vol. 97, No. 12, pp. 6287-6291.

(Continued)

*Primary Examiner*—Medina A Ibrahim
(74) *Attorney, Agent, or Firm*—Marshall, Gerstein & Borun LLP

(57) ABSTRACT

The present invention relates to a gene being capable of modifying resistance against a heavy metal or salt, or accumulation properties, a recombination vector including the genes, and a transformant using the recombination vector. A gene having heavy metal resistance and accumulation properties includes a sequence encoding a transmembrane protein having five times repeated similar four transmembrane domains. A recombination vector includes the gene having heavy metal resistance and accumulation properties, and further includes a salt or drought resistance gene having at least one selected from the group consisting of a sequence encoding an ABC transporter including twice repeated six transmembrane domains and ATP-binding domains.

15 Claims, 33 Drawing Sheets

OTHER PUBLICATIONS

Article—AtATM3 Is Involved in Heavy Metal Resistance in Arabidopsis; Do-Young Kim, et al.; Plant Physiology, Mar. 2006, vol. 140, pp. 922-932.

Article—A tobacco plasma membrane calmodulin-binding transporter confers $Ni^{2+}$ tolerance and $Pb^{2+}$ hypersensitivity in transgenic plants; Tzahi Arazi, et al.; The Plant Journal (1999) 20(2), pp. 171-182.

Article: Overexpression of Glutathione Synthetase in Indian Mustard Enhances Cadmium Accumulation and Tolerance; Yong Liang Zhu, et al.; Plant Physiology, Jan. 1999, vol. 119, pp. 73-79.

Article : A Novel Family of Cys-Rich Membrane Proteins Mediates Cadmium Resistance in Arabidopsis, Won-Yong Song, et al.; Plant Physiology, Jun. 2004, vol. 135, pp. 1027-1039.

Article: AtPDR12 Contributes to Lead Resistance in Arabidopsis; Miyoung Lee, et al.; Plant Physiology, Jun. 2005, vol. 138, pp. 827-836.

Article: Phytoremediation of methylmercury pollution: *merB* expression in *Arabidopsis thaliana* confers resistance to organomercurials; Scott P. Bizily, et al.; Proc. Natl. Acad. Sci USA, vol. 96, pp. 6808-6813, Jun. 1999 Ecology.

Article: Functional Expression of a Bacterial Heavy Metal transporter in Arabidopsis Enhances Resistance to and Decreases Uptake of Heavy Metals; Joohyun Lee, et al., Plant Physiology, Oct. 2003, vol. 133, pp. 589-596.

Article: Engineering tolerance and accumulation of lead and cadmuium in transgenic plants; Won-Yong Song, et al; Nature Biotechnology, vol. 21, No. 8, Aug. 2003, pp. 914-919.

\* cited by examiner

FIG.1C

```
TM1-4    ------------------------------MECGGVSAVVQPAVHMGQPGQPAKPPVVQPWEYSLRKYLLLLAALVTVTVAAGFSPPGG--VWQAAHDGQPAGDPIIRGTHYRRYL  84
TM5-8    DVMSTPDPDSDAVTIPSPLRDSDPNVKEEEDRKREALKKLKANERLRKVLMLLATFAVSITYVAGLSMPGG-FWDSTGTSYRPGDAILKDRHRPRLT  95
TM9-12   ------------------------------TDNVSARKGLDKA-------------RSLVLLLATLAATITYTAGLDPPGG--LWQDKGDGVIAGDPILITNIRRYR  62
TM13-16  ------------------------------KDDQEDELLEKR--------------RKRLLLFAILAATITYQAGLTPPGGFLLQDDTLGHAGDPILLHNYPVRYH  63
TM17-20  ------------------------------EKNEDEEEAKKHAR-----------RKYLMLLGILVASVAYQAGLEPPGG--AVQNNDNGYEAGNPVMNDNRRPRYL  63
                                         .  .:*.  :.::::.*. *:.*** .  . ..:::: *

TM1-4    AFFYCNATAFAASLVUIVLILILAVRHDKKGKDSRWUVUPLRLVMVLDLLSLMGAYGAGTCQDKISIVYSAVLVAAVFLYAVLKMMDVWCPDNKTG 182
TM5-8    AFLLCNTTSFVASLLLIIMLLIIDGKKLRDKKARS-----------LVLYGFIVVALVSLVGAYTAGSCRETKTTIYVVSLTGGILAMAYILLYAFYTLKSSRSS 189
TM9-12   AFYYCNSVAFVASLLVLULULVQTERLIKHH----------------VLEAAMILDLFGLIGAYAAGSCRNVNSSVYVMALAGAALIYVVIHIVFTLELDQKDK 150
TM13-16  AFFYCNSVSFMLSIALIILLVNPNLYRPAIQSN---------------ALSVCTAVGLFCLMGAYAAGSTQHRKTSIYIFVLVAVVLLVAGGLLLVFLLKRKLSNA 155
TM17-20  TFFYSNSUSFVASIVVIIMLFALLVAYAAGSNRGLKTSLYVVALIFAVLGYFAIHTVLACTVCRHERR 161
         *  . .:::.* *:  *:*::                                    :.  .   .*  :  *:  **:.  ::  **   *

TM1-4    PGCDGTMSSAPNSNSNSG 200
TM5-8    PTQPTDALQQT------- 200
TM9-12   ----------------- 150
TM13-16  VVSPPREQNEEERKEVE- 172
TM17-20  Q-------SSSVV----- 167
```

GENES THAT ALTER CAPACITY TO ACCUMULATE HEAVY METALS AND SALTS OR RESISTANCE TO HEAVY METALS, SALTS OR DROUGHT, AND TRANSFORMANTS EXPRESSING THE GENES

CROSS-REFERENCE TO RELATED APPLICATION

This application claims priority to and the benefit of Korean Patent Application No. 10-2006-0118652, filed in the Korean Intellectual Property Office on Nov. 28, 2006, the entire contents of which are incorporated herein by reference.

BACKGROUND OF THE INVENTION (a) Field of the Invention

The present invention relates to a gene being capable of modifying resistance against a heavy metal or salt, or accumulation properties, and a transformant produced using the gene. More particularly, the present invention relates to a gene being capable of modifying resistance against a heavy metal or salt, or accumulation properties, a recombination vector including the gene that improves resistance against salt or drought, a transformant produced using the recombination vector, a transgenic plant that has good resistance against a heavy metal, salt, or drought, efficiently removes or accumulates a heavy metal, and decreases uptake of a heavy metal, a phytoremediation method using the transgenic plants, and a method of developing a safety plant.

(b) Description of the Related Art

Heavy metals are major environmental toxicants, which cause reactive oxidation species generation, DNA damage, and enzyme inactivation by binding to active sites of enzymes in cells.

Contamination of the environment with heavy metals has increased drastically due to industrialization. By the early 1990s, the worldwide annual release had reached 22,000 tons of cadmium, 954,000 tons of copper, 796,000 tons of lead, and 1,372,000 tons of zinc (Alloway B J & Ayres D C 1993 Principles of environmental pollution. Chapman and Hall, London). The soils contaminated with heavy metal inhibit normal plant growth and cause contamination of foodstuffs. Many heavy metals are very toxic to human health and carcinogenic at low concentrations.

Therefore removal of heavy metals from the environment is an urgent issue. Traditional methods of dealing with soil contaminants include physical and chemical approaches, such as the removal and burial of the contaminated soil, isolation of the contaminated area, fixation (chemical processing of the soil to immobilize the metals), and leaching using an acid or alkali solution (Salt D E, Blaylock M, Kumar N P B A, Viatcheslav D, Ensley B D, et al. 1995. Phytoremediation: a novel strategy for the removal of toxic metals from the environment using plants. Bio-Technology 13, 468-74; Raskin I, Smith R D, Salt D E. 1997 Phytoremediation of metals: using plants to remove pollutants from the environment. Curr. Opin. Biotechnol. 8, 221-6). These methods, however, are costly and energy-intensive processes.

Phytoremediation has recently been proposed as a low-cost, environment-friendly way to remove heavy metals from contaminated soils, and is a relatively new technology for cleanup of contaminated soil that uses general plants, specially bred plants, or transgenic plants to accumulate, remove, or detoxify environmental contaminants. The phytoremediation technology is divided into phytoextraction, rhizofiltration, and phytostabilization. Phytoextraction is a method using metal-accumulating plants to extract metals from soil into the harvestable parts of the plants; rhizofiltration is a method using plant roots to remove contaminants from polluted aqueous streams; and phytostabilization is the stabilization of contaminants such as toxic metals in soils to prevent their entry into ground water, also with plants (Salt et al., *Biotechnology* 13(5): 468-474, 1995).

Examples of phytoremediation are methods using the plants of *Larrea tridentate* species that are particularly directed at the decontamination of soils containing copper, nickel, and cadmium (U.S. Pat. No. 5,927,005), and a method using Brassicaceae family (Baker et al., *New Phytol.* 127:61-68, 1994).

In addition, phytoremediation using transgenic plants that are generated by introducing genes having resistant activity for heavy metals have been attempted. Examples of heavy metal resistant genes are AtATM3 (ABC transporters of mitochondria), CAX2 (Calcium exchanger 2), cytochromium P450 2E1, NtCBP4 (*Nicotiana tabacum* calmodulin-binding protein), GSHII (glutathione synthetase), AtPcr1 (plant cadmium resistance), AtPDR12 (pleiotropic drug resistance), or MRT polya peptide (metal-regulated transporter polypeptide). AtATM3 is an ABC-type transporter that improve cadmium and lead resistance of over-expressed transgenic plants, and increases cadmium contents in transgenic plants (Kim et al., *Plant Physiol.* 140:922-932, 2006), CAX2 accumulates heavy metals including cadmium and manganese in plants (Hirschi K D et al., *Plant Physiol.* 124:125-134, 2000), cytochromium P450 2E1 uptakes and decomposes organic materials such as trichloroethylene (TCE) (Doty S L et al., *Proc. Natl. Acad. Sci.* USA 97:6287-6291, 2000). Transgenic plant transformed with NtCBP4 has resistant activity for nickel (Arazi T et al. *Plant J.* 20:171-182, 1999), GSHII accumulates cadmium (Liang Zhu Y et al., *Plant Physiol.* 119:73-80, 1999), plants that over-express AtPcr1 has cadmium resistance by decreasing cadmium content (Song et al., *Plant Physiol.* 135:1027-1039, 2004, Korean Patent Application No. 2003-0058299 and U.S. patent application Ser. No. 10/907,694), transgenic plants transformed with AtPDR12 improves lead resistance by lead contents in a plant (Lee et al., *Plant Physiol.* 138:827-836, 2005), and MRT polypeptides remove heavy metals such as iron, cadmium, manganese, and zinc from soils (U.S. Pat. No. 5,846,821.

Recently, it is reported that bacteria and yeast genes as well as plant genes can be introduced into a plant to effectively improve heavy metal resistance and accumulation. For example, merB (organomercurial lyase) was reported to be able to decompose organic mercury materials (Bizily S P et al., Proc. Natl. Acad. Sci. USA 96:6808-6813, 1999). In addition, a ZntA gene, which is a P-type pump of bacteria, was reported to increase resistance against and also, less uptake them when it was over-expressed by merB (Lee et al., Plant Physiol. 133:589-596, 2003; Korean Patent No. 0515520). An Ycf1 (yeast cadmium factor1) gene, which is an ABC-type carrier of yeast, was reported to be expressed in a plant and thereby, increase resistance against cadmium and lead and accumulation thereof when it was over-expressed by merB (Song et al., Nat Biotechnol. 21:914-919, 2003; International patent PCT/KR02/01934). Likewise, another method was reported that a transgenic plant could be developed by expressing a MRP-type ABC carrier of yeast in a plant when it was over-expressed by merB (Korean Patent No. 0480843).

However, these transgenic plants including a gene with heavy metal resistances outgrew a wild-type one in a contaminated soil but did not have much improved accumulation in the shoot region. In general, a plant for environment purification should not only have resistances against contamination materials but also be able to carry them to the shoot region and thereby, accumulate them there. The reason is that the shoot region of a plant can be more safely and economically harvested and disposed rather than the root.

However, a conventional transgenic plant including a gene with heavy metal resistance a little outgrew a wild-type one in a contaminated soil but turned out to be not be able to effectively pump up heavy metals from root to shoot region and thereby, accumulate them in the shoot region.

In general, a plant uptakes various contamination materials in the environment when it uptakes water. Accordingly, when a plant can uptake more water and transpire it, it can accumulate more contamination materials in its body faster. Therefore, this kind of a plant can decrease contamination in the environment in a shorter term than a wild-type one, contributing to diminishing time and cost for purifying the environment.

In addition, water insufficiency is world-widely raised as a serious problem. The world already started to be desertificated in several areas. This is subsequently causing another serious problem in farming and environment. Therefore, a plant that can need less water and successfully survive in a dry and highly-salted environment should be desperately developed. In particular, when a plant is developed for economically purifying environment in a dry area, it should ideally have improved resistance against drought as well as contamination materials. On the other hand, when a plant can decrease transpiration, it can contribute to purifying environment and increasing agricultural productivity in a very arid area.

Unlike a plant for purifying environment, a crop is required to uptake contamination materials to a minimum. If a crop absorbs heavy metals or other contamination materials, it can hurt people and domestic animals consuming it. Therefore, a crop cannot be poisoned but safe from heavy metals by expressing a gene removing a heavy metal therein. In addition, when a gene accumulating a heavy metal in a cell is artificially less expressed or suppressed to oppositely work, a transgenic plant including the gene can have less accumulated heavy metals than a wild-type one, contributing to development of a safer plant.

On the other hand, a gene related to have heavy metal resistance, salt resistance, drought resistance, and the like can be used to rehabilitate an environment. The rehabilitation of environment can be accomplished by recovering nature artificially or naturally destroyed once and rebuilding ecosystem as it used to be. Accordingly, the environment can not only be refreshed but natural resources also can be preserved, so that human can cohabit with other living species. A method of rehabilitating environment includes removal of contamination materials, planting of a resistant plant, reintroduction of extinct animals, and the like. For example, Daegoo arboretum was created by planting a wild plant and a medicinal plant in a landfill used for dumping trash and thereby, changing it into an ecosystem education center and a rest place. In addition, Kwangjoo Ooncheon reservoir used to be contaminated due to domestic sewage but was now rehabilitated into a natural ecosystem park. However, a landfill may release cadmium with leachate. An abandoned mine can be severely arid. Therefore, genes with high resistance against heavy metals and drought can be usefully used for rehabilitating a landfill or an abandoned mine. In addition, a gene with high salt resistance can be used for rehabilitating a reclaimed land with a high salt concentration.

SUMMARY OF THE INVENTION

One embodiment of the present invention provides a gene having heavy metal resistance or being capable of modifying heavy metal accumulation properties, and a gene having salt or drought resistance or being capable of modifying salt accumulation properties.

Another embodiment of the present invention provides a recombination vector including a gene being capable of modifying resistance against a heavy metal and heavy metal accumulation properties.

Another embodiment of the present invention provides a transformant having modified heavy metal resistance and accumulation properties.

Another embodiment of the present invention provides a method of producing a transformant having modified heavy metal resistance and accumulation properties.

Another embodiment of the present invention provides a method of changing areas contaminated with heavy metals to environmentally-friendly areas.

Another embodiment of the present invention provides a method of developing a plant having decreased heavy metal contents.

Another embodiment of the present invention provides a recombination vector including a gene being capable of improving resistance against salt or drought.

Another embodiment of the present invention provides a transformant having improved resistance against salt or drought.

Another embodiment of the present invention provides a method of producing a transformant having improved resistance against salt or drought.

Another embodiment of the present invention provides a method of changing salty or dried areas to environmentally-friendly areas.

According to an embodiment of the present invention, provided is a gene having heavy metal resistance and accumulation properties and including a sequence encoding a transmembrane protein having five times repeated similar four transmembrane domains.

According to an embodiment of the present invention, provided is a recombination vector that includes a gene linked to transcription and translation controlling element to be expressed in a plant, and having heavy metal resistance and accumulation properties and including a sequence encoding a transmembrane protein having five times repeated similar four transmembrane domains or a homologous sequence.

The recombination vector further includes a salt or drought resistance gene having at least one selected from the group consisting of a sequence encoding an ABC transporter including twice repeated six transmembrane domains and ATP-binding domains; a sequence encoding a protein including a GTP-binding domain and a CaaL domain (geranylgeranylation motif) being capable of transferring its position from a cytoplasm to cell membrane; and a homologous sequence with the above sequences.

According to another embodiment of the present invention, provided is a transformant produced using the recombination vector.

According to another embodiment of the present invention, provided is a transgenic plant transformed by the recombination vector.

According to another embodiment of the present invention, provided is a transgenic plant cell transformed by the recombination vector.

According to another embodiment of the present invention, provided is a method of producing a heavy metal resistant plant that includes (a) constructing expression cassette that includes a gene linked to a transcription and translation controlling element to be expressed in a plant, and having heavy metal resistance and accumulation properties and including a sequence encoding a transmembrane protein having five times repeated similar four transmembrane domains, or a homologous sequence of the gene, (b) preparing a recombination vector including the expression cassette, and (c) introducing the recombination vector into a plant cell or a plant tissue.

The expression cassette further includes a salt or drought resistance gene having at least one selected from the group consisting of a sequence encoding an ABC transporter including twice repeated six transmembrane domains and ATP-binding domains; a sequence encoding a protein including a GTP-binding domain and a CaaL domain (geranylgeranylation motif) being capable of transferring its position from a cytoplasm to cell membrane; and a homologous sequence with the above sequences.

BRIEF DESCRIPTION OF THE DRAWINGS

FIGS. 1A to 1C show positions of 20 transmembrane domains of TaTM20 in cell membrane (A); shows three dimensional domains that are interacted with each other and gethered (B); and shows homology between repeated transmembrane domain sequence of the TaTM20 (SEQ ID NO: 2)(black rod) and a protein kinase c phosphorylation motif (C).

DETAILED DESCRIPTION OF THE INVENTION

Figure 1A:
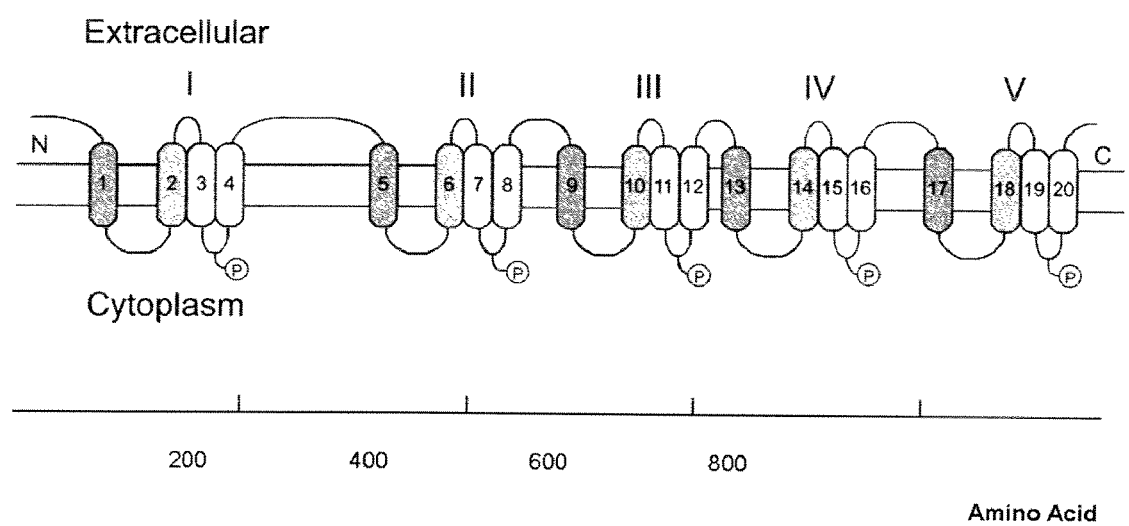

In the present invention, "transmembrane protein" refers to a transmembrane protein penetrating lipid double layer. The transmembrane protein includes similar four transmembrane domains that are repeated five times and acts in uptake and release of a heavy metal and a salt. Examples of the heavy metal includes arsenic, antimony, lead, mercury, cadmium, chromium tin, zinc, barium, bismuth, nickel, cobalt, manganese, iron, copper, vanadium, and so on.

The "ABC transporter (ATP-binding cassette transporters)" transports materials using an energy generated from ATP decomposition and acts in uptakes of nutrients into a cell and releases of toxic materials out of a cell.

The "homoglogy" refers to sequence similarity between nucleic acids (DNAs) or proteins.

The "expression suppressing method (RNAi)" refers to a method of suppressing expression of a corresponding gene by making a homoglogous base sequence into a hair-pin structure. RNAi defends against virus dsRNA by decomposing the virus dsRNA as follows. 1) A Dicer enzyme cuts dsRNA to obtain 21-23 base small-interfering RNA (siRNA). 2) Dicer helps the cut siRNA to bind with a RNA-induced silencing complex (RISC). 3) RISC bound with siRNA cuts antisense messenger RNA (mRNA) of siRNA. Therefore siRNA and antisense mRNA are decomposed. According to one embodiment of the present invention, a RNAi transgenic plant having reduced AtPDR8 expression is provided by transforming a construct designed to dsRNA using a specific gene; particularly a partial sequence of AtPDR8. RNAi is a gene silencing technique where siRNA recognizes specific sequences of mRNA and binds with them to decompose mRNA. Herein, siRNA binds with mRNA of another gene having similar sequences to siRNA (the gene has a homoglogy with AtPDR8) to decompose it.

The "heavy metal resistant protein" refers to a protein that makes growth of an organism not be suppressed in the presence of a heavy metal.

The "salt, drought resistant protein" refers to a protein that makes growth of an organism not be suppressed in the presence of a high concentration of salt or drought.

The "transgenic plant" refers to a plant including a foreign DNA sequence by genetic engineering, and expressing the foreign DNA sequence in a plant cell, a plant tissue, or a plant.

The gene having heavy metal resistance and accumulation properties includes a sequence encoding a transmembrane protein having five times repeated similar four transmembrane domains.

The sequence encoding a transmembrane protein having five times repeated similar four transmembrane domains may be a sequence encoding a TaTM20 protein of SEQ ID NO.: 1. The homologous sequence refers to a sequence having homoglogy of 70% or more with SEQ ID NO.: 1. According to one embodiment, it refers to a sequence having homoglogy of 80% or more with SEQ ID NO.: 1. According to another embodiment, it refers to a sequence having homoglogy of 90% to 95% or 90% to 99% with SEQ ID NO.: 1.

The expression cassette according to one embodiment of the present invention includes a gene or a homologous gene linked to a transcription and translation controlling element to be expressed in a plant.

The expression cassette further includes a gene modifying heavy metal, salt, or drought resistance and accumulation properties, or a gene having a salt or drought resistance having at least one selected from the group consisting of a sequence encoding an ABC transporter including twice repeated six transmembrane domains and ATP-binding domains; a sequence encoding a protein including a GTP-binding domain and a CaaL domain (geranylgeranylation motif) being capable of transferring its position from a cytoplasm to cell membrane; and a homoglogous sequence with the above sequences.

The sequence encoding an ABC transporter including twice repeated six transmembrane domains and ATP-binding domains may be a sequence encoding an AtPDR8 protein having SEQ ID NO.: 3. The homologous sequence refers to a sequence having homology of 70% or more with SEQ ID NO.: 3. According to one embodiment, it refers to a sequence having homoglogy of 80% or more with SEQ ID NO.: 3. According to another embodiment, it refers to a sequence having homoglogy of 90% to 95% or 90% to 99% with SEQ ID NO.: 3.

The expression cassette may further includes a gene encoding a protein (Rop2 protein) including a GTP-binding domain controlling plant pore movement and a CaaL domain (geranylgeranylation motif) being capable of transferring its position from a cytoplasm to cell membrane. The gene encoding the Rop2 protein has a sequence having homology of 70% or more with SEQ ID NO.: 5. According to one embodiment, it has a sequence having homoglogy of 80% or more with SEQ ID NO.: 5. According to another embodiment, it refers to a sequence having homoglogy of 90% to 99% with SEQ ID NO.: 5.

The expression cassette according to one embodiment of the present invention includes a promoter; a gene including at least one selected from the group consisting of a gene encoding a TaTM20 protein, a gene encoding TaTM20 and AtPDR8 proteins, a gene encoding TaTM20, AtPDR8, and Rop2 proteins, and homoglogous sequences with the above gene; and a transcription terminator. Examples of the promoter is a promoter for plant expression that includes at least one selected from the group consisting of a CMV (Cauliflower Mosaic Virus) 35S promoter, a CMV 19S promoter, a nos (nopaline synthase) promoter of an *Agrobacterium tumefaciens* Ti plasmid, an ocs (octopine synthase) promoter, a mas (mannopine synthase) promoter, and another known promoter.

The expression cassette may further a marker gene that indicates expression of genes encoding TaTM20, AtPDR8, or Rop2 protein and selects transformants. The marker gene may be a gene having resistance to antibiotics selected from the group consisting of kanamycin, hygromycin, zentamycin, and bleomycin or a gene encoding GUS (β-glucuronidase), CAT (chloramphenicol acetyltransferase), luciferase, or GFP (green fluorescent protein). The marker gene is transferred to a plant by an expression cassette to make transformant selected in a medium including specific antibiotics.

The recombination vector according to one embodiment of the present invention includes the expression cassette. The recombination vector may be a pGA1535/TaTM20 or pCAMBIA1302/AtPDR8. The pGA1535/TaTM20 includes pGA1535, a 35S promoter, a TaTM20 gene, and a nopaline synthesis enzyme transcription terminator, and the pCAM- BIA1302/AtPDR8 includes a 35S promoter, an AtPDR8 gene, and a nopaline synthesis enzyme transcription terminator.

According to one embodiment of the present invention provides a transformant including the recombination vector. The transformant includes a sequence encoding the transmembrane protein transferring a heavy metal; a sequence encoding an ABC transporter; and sequences encoding a transmembrane protein, an ABC transporter, and a protein controlling pores of a plant. The sequences are operably linked a transcription and translation controllers and is designed to be controlled by the controllers.

The transformant is a plant, a plant cell, and a plant tissue. The plant part includes a seed. The plants may be without limitation herbaceous plants and trees, and may include flowering plants, garden plants, an onion, a carrot, a cucumber, an olive tree, a sweet potato, a potato, a cabbage, a radish, lettuce, broccoli, tobacco such as *Nicotiana tabacum, Petunia hybrida*, a sunflower, *Brassica juncea*, turf, *Arabidopsis thaliana, Brassica campestris, Betula platyphylla*, a poplar, a hybrid poplar, or *Betula schmidtii*. The plant may be asexually reproduced using a method selected from the group consisting of somatic embryogenesis, tissue culture, and cell line culture.

Techniques for generating transformants are well known. An example is *Agrobacterium tumefaciens*-mediated DNA transfer. *A. tumefaciens* generated by electroporation, microparticle injection, or with a gene gun can be used.

According to another embodiment of the present invention, provided is a method of producing a heavy metal resistant plant that includes (a) constructing expression cassette that includes a gene linked to a transcription and translation controlling element to be expressed in a plant, and having heavy metal resistance and accumulation properties and including a sequence encoding a transmembrane protein having five times repeated similar four transmembrane domains, or a homologous sequence of the gene, (b) preparing a recombination vector including the expression cassette, and (c) introducing the recombination vector into a plant cell or a plant tissue.

The expression cassette further includes a salt or drought resistance gene having at least one selected from the group consisting of a sequence encoding an ABC transporter including twice repeated six transmembrane domains and ATP-binding domains; a sequence encoding a protein including a GTP-binding domain and a CaaL domain (geranylgeranylation motif) being capable of transferring its position from a cytoplasm to cell membrane; and a homoglogous sequence with the above sequences.

The transgenic plant that over-expresses a TaTM20 protein (SEQ ID NO.: 2) or a protein having a homology of 70% or more has an improved resistance to a heavy metal and modified heavy metal accumulation. In one embodiment, the transgenic plant may be transformed to over-express a protein having a homology of 80% or more, in another embodiment, it may be transformed to over-express a protein having a homology of 90% to 95%, and in yet another embodiment, it may be transformed to over-express a protein having a homology of 95% to 99%. The transgenic plant that over-expresses a AtPDR8 protein (SEQ ID NO.: 4) or a protein having a homology of 70% or more has an improved resistance to a heavy metal or a salt thereof and drought and modified heavy metal accumulation. In one embodiment, the transgenic plant may be transformed to over-express a protein having a homology of 80% or more, in another embodiment, it may be transformed to over-express a protein having a homology of 90% to 95%, and in yet another embodiment, it may be transformed to over-express a protein having a homology of 95% to 99%.

The transgenic plant that lower-expresses or inactivates a Rop2 protein (SEQ ID NO.: 6) or a protein having a homology of 70% or more using a RNAi method shows active transpiration by opening pores of the plant in a regular condition and thereby promotes movement of heavy metals into shoot region. It may improve drought resistance by closing pores of the plant in a drought condition. Resultantly, the Rop2 protein improves drought resistance. In one embodiment, the transgenic plant may be transformed to over-express a protein having a homology of 80% or more, and in another embodiment, it may be transformed to over-express a protein having a homology of 90% to 99%.

Therefore, the transgenic plant can transport heavy metals from a root to a shoot region and then effectively accumulate heavy metal. That is to say, the transgenic plant can transport contamination materials such as heavy metals along with water through transpiration to shoot regions by including a modified gene to control plant pore movement or changing expression level of genes resulting in improvement of drought resistance properties.

Figure 1B:
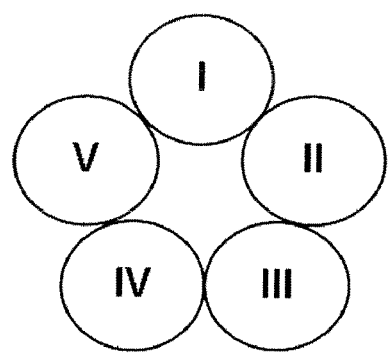

The genes encoding the TaTM20 and AtPDR8 proteins are introduced into plant protoplasts to be expressed in a cell membrane of a plant. FIG. 1A shows positions of 20 transmembrane domains of TaTM20 in cell membrane; FIG. 1B shows three dimensional domains that are interacted with each other and gethered; and FIG. 1C shows homology between repeated transmembrane domain sequence of the TaTM20 (black rod) and a protein kinase c phosphorylation motif.

A transgenic plant transformed with an ABC transporter and a transmembrane protein gene can grow well in an environment contaminated with a heavy metal. Thus, a safe plant having low uptake of a heavy metal and can be obtained. Alternatively, heavy metal reduction plant that uptakes heavy metals from soil, air, or water can be obtained by a low expression technique such as RNAi. The transgenic plant may also be required for removing a heavy metal inflowed with a yellow sand or natural disasters.

The following examples are provided for illustrative purposes and are not intended to limit the scope of the invention as claimed herein. Any variations in the exemplified compositions and methods which occur to the skilled artisan are intended to fall within the scope of the present invention.

EXAMPLE 1

Conditions for Incubating a Plant

Seeds of wild-type and transformed Arabidopsis and wheat (*Triticum aestivum* L. cv. Atlas 66) were sterilized on the surface with ethanol and bleach and thereafter, kept in the darkness at 40 ☐ for 2 days. Then, they were placed on a ½ MS medium (Murashige and Skoog, 1962). The medium was horizontally or vertically incubated for 2 to 3 weeks.

EXAMPLE 2

Identification of a Cadmium-Resistant Gene in the Wheat Root cDNA Library

Figure 5:
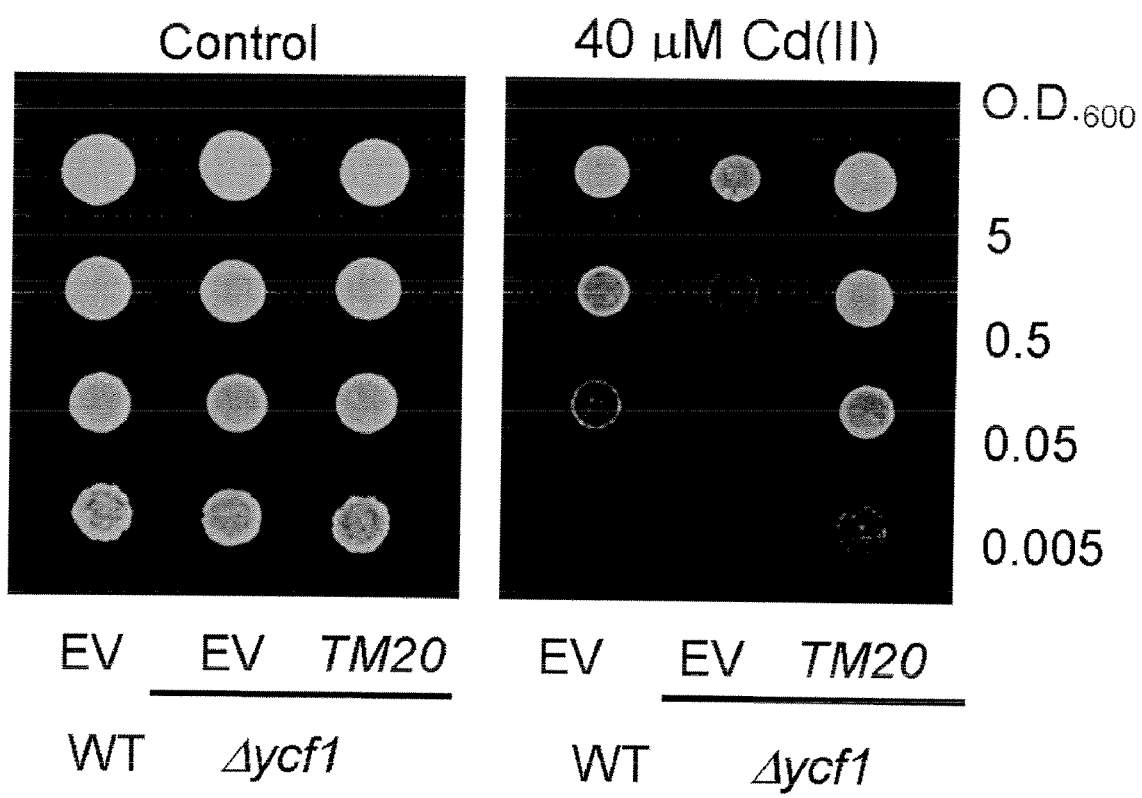
FIG. 5 is a photograph showing cadmium resistance improvement by over-expression of TaTM20 in yeast.

Identification of a cadmium-resistant gene the wheat root cDNA library was performed, after it was inserted into ycf1-null yeast using a lithium acetate method. Its functional complementation was also examined. In addition, identification of plasmid was performed by selecting a cell cluster incubated in a medium including 60 μM cadmium chloride (CdCl$_2$). Its base sequence was identified (SEQ ID NO.: 1), and then, it was reinserted in the ycf1-null yeast to confirm cadmium resistance again. When wild-type yeast (wt), the ycf1-null yeast inserted with an empty vector (EV), and the other ycf1-null yeast inserted with a vector including a TaTM20 gene were incubated in a medium and examined, the ycf1-null yeasts inserted with a vector including a TaTM20 gene turned out to outgrow the one inserted with empty vector as well as the wild-type one in a medium including cadmium (FIG. 5). Therefore, the result indicates that TM20 improved cadmium resistance in yeast.

EXAMPLE 3

Figure 6A:
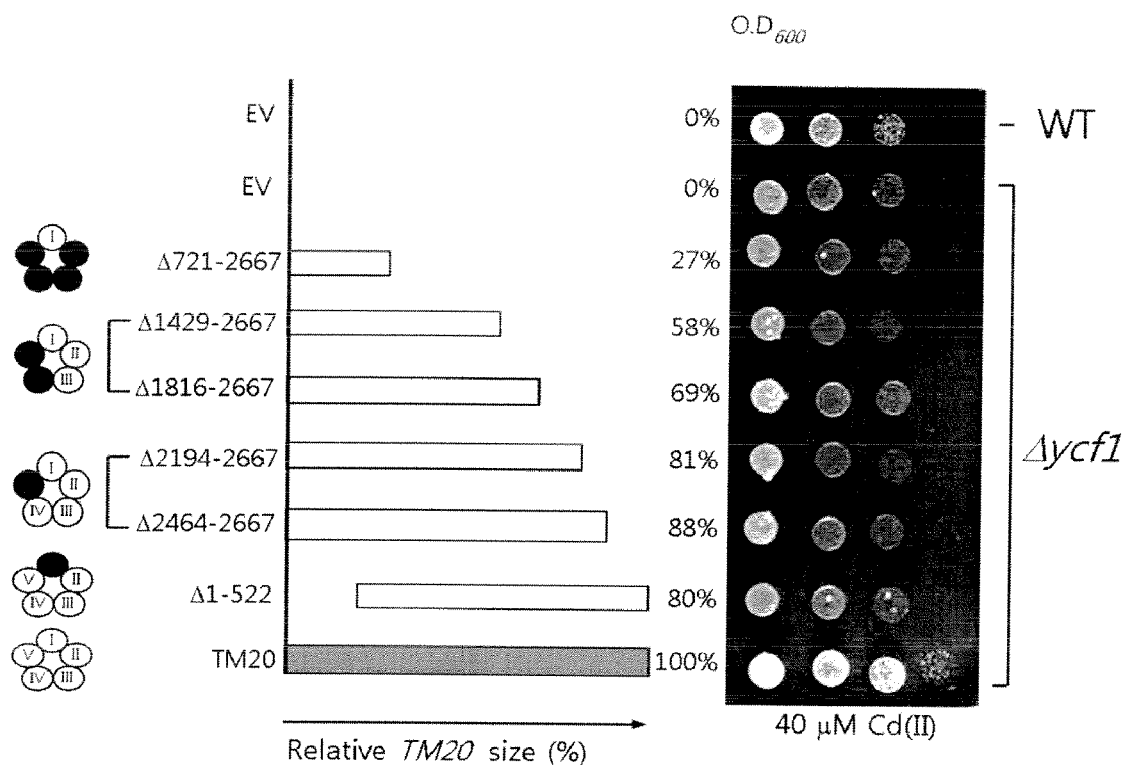
FIGS. 6A and 6B show that full-length TaTM20 confers cadmium resistance. A yeast where a protein without N-terminal and C-terminal is expressed shows similar cadmium resistance to a wild type (A), and gene fragments in (A) is actually expressed in yeast (B).
Figure 6B:
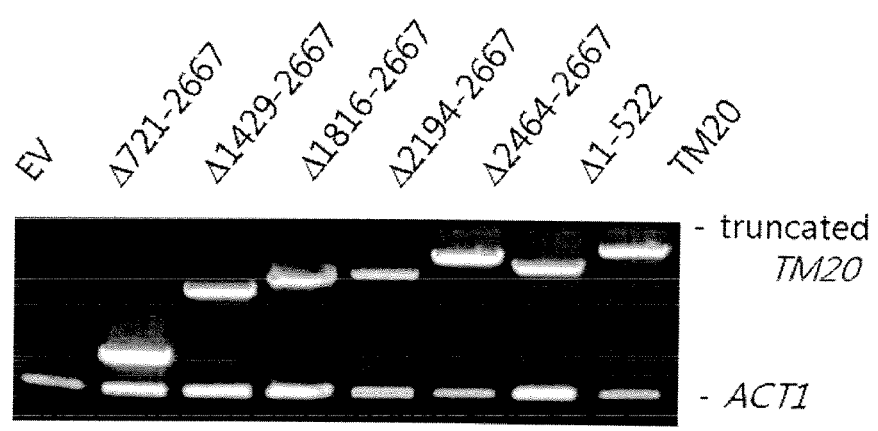

Preparation of a TaTM20 Construct Without N-Terminal and C-Terminal and Experiment of Cadmium Resistances in Yeast TaTM20 cDNA from which all N-terminals and C-terminals were removed was produced by severing restriction enzyme of a PCR product. Each gene was inserted into ycf1-null yeast in a lithium acetate method, and the yeasts were selected in a minimum medium lacking of uracil. The yeasts including each gene was incubated at 30° C. for 3 days in a ½ SG medium treated with 30 uM cadmium chloride to experiment cadmium resistance complementation. As a result, the yeast including a transformed gene whose N-terminals and C-terminals were a little removed turned out to have similar cadmium resistance to the one inserted with an empty vector (FIG. 6A). Accordingly, cadmium resistance of the yeast conferred by TaTM20 is showed, only when 4 TM20 transmembrane domains are five times repeated.

EXAMPLE 4

Preparation of Transformed Arabidopsis

A TaTM20 gene was recombined from a pYES2:TaTM20 gene to a plant expression vector by using a HindIII restriction enzyme. The separated HindIII fragments included a 5' untranslated region of 40 base pairs, a TaTM20 gene of full length 2670 base pairs, a 3' untranslated region of 109 base pairs, and a translation termination codon.

On the other hand, pGA1535 was used as a plant expression vector for preparing transformed Arabidopsis. It had a CaMV35S promoter, a plurality of cloning sites, and a nopaline synthetase terminator. Then, Arabidopsis was transformed by using Agrobacterium (LBA4404) including a pGA1535:TaTM20 gene in a floral dipping method (Clough and Bent, 1988). The transformed seed was selected in a ½ MS medium including 30 ug/L of kanamycin antibiotics and gathered from living plants. In addition, homogenous conjugation seeds through three-generation were used for a phenotype analysis.

An AtPDR8 gene was amplified by PCR using an AtPDR8F-SB (5'-TCCCCCGGGGGCGCGGATCCGC-GATGGATTACAATCCAAATCTTCC-3') (SEQ ID NO: 7)primer and an AtPDR8R-PX (5'-GACACGTGCTC-CGCTCGAGCGGTTATCTGGTCTGGAAGTTGAG-3') primer (SEQ ID NO: 8), using cDNA obtained from Arabidopsis as a template. Then, the gene was inserted into a T-vector and recombined into a pCambia1302 binary vector by using restriction enzyme. The pCambia1302 vector was used as a plant expression vector for preparing transformed Arabidopsis and included a CaM V35S promoter, a plurality of cloning sites, and a nopaline synthetase terminator.

The Arabidopsis was transformed by using Agrobacterium (GV3101) including pCambia1302:AtPDR8 in the same method as TaTM20. The transformed seed was selected from a ½ MS medium including 30 ug/L of hygromycin and gathered from living plants.

EXAMPLE 5

Examination of Cadmium Resistance

Figure 8A:
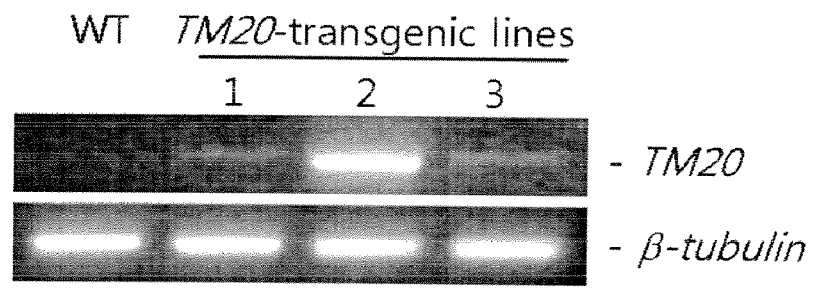
FIGS. 8A to 8D show that TaTM20 transformed Arabidopsis has improved cadmium resistance. Expression of TaTM20 gene in a transformant is confirmed by RT-PCR (A); transformants expressing TaTM20 genes has improved cadmium resistance when growing them in a medium including cadmium compared to a wild type; and biomass and root lengths of transformants are measured (C and D).
Figure 8B:
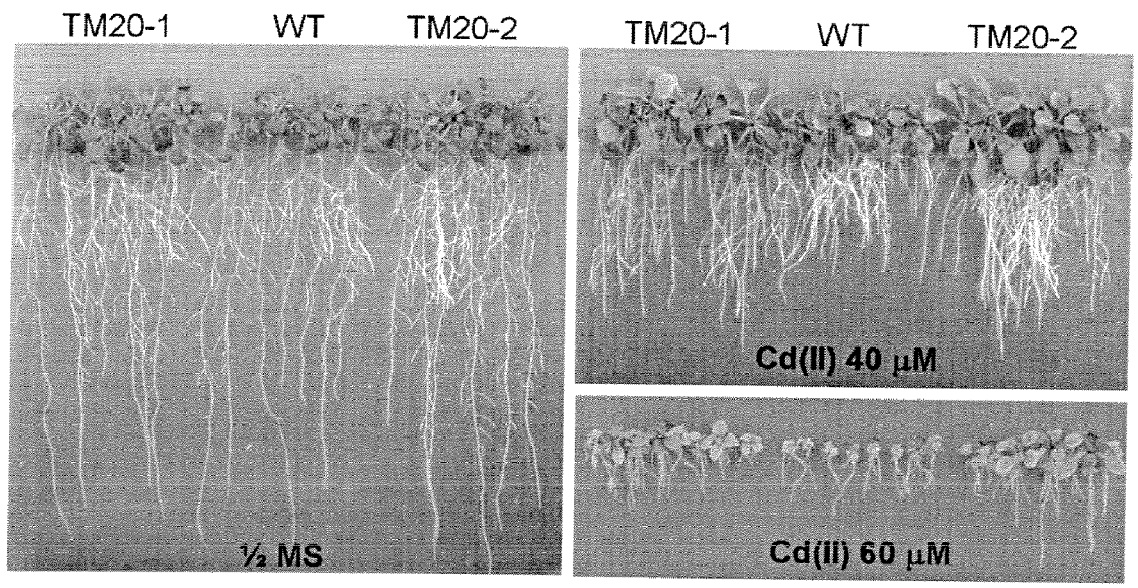
Figure 8C:
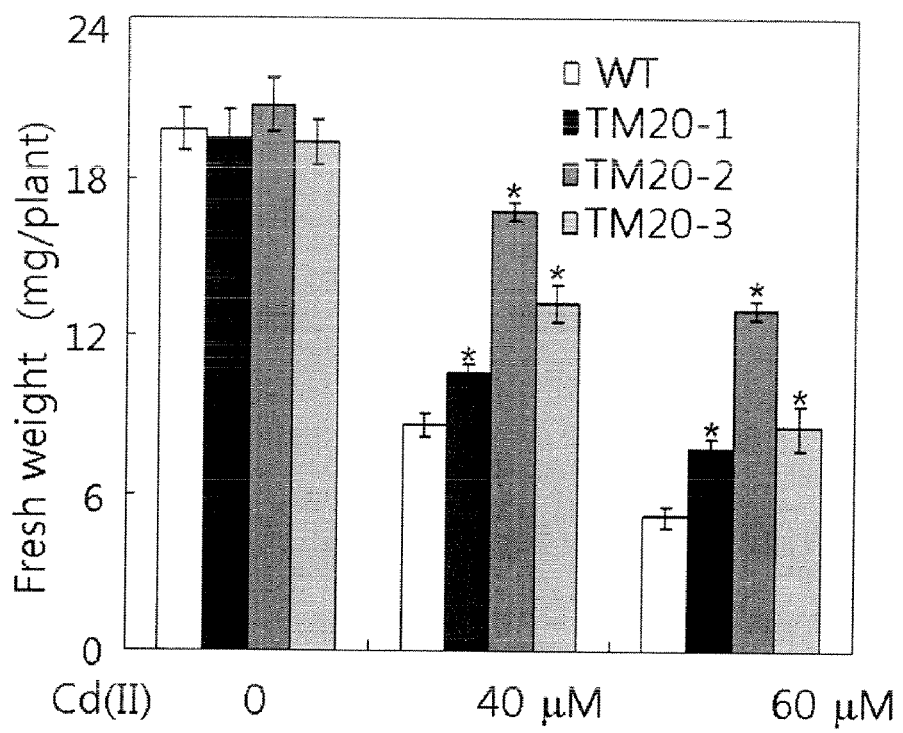
Figure 8D:
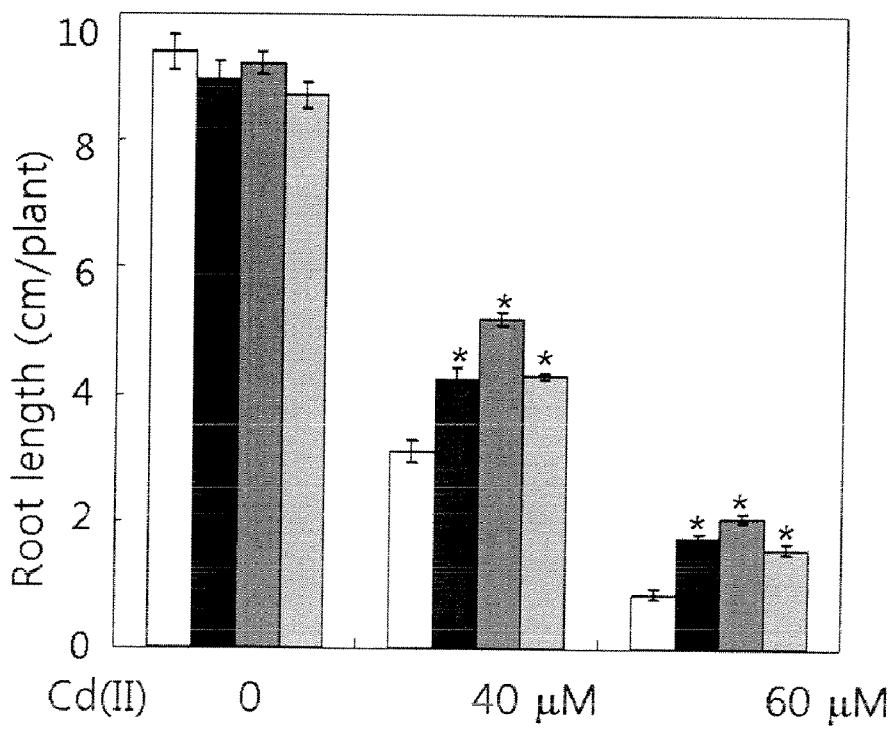

Wild-type Arabidopsis and TaTM20 over-expression Arabidopsis (TM20-1 and TM20-2) were incubated in a ½ MS medium including 40 or 60 μM cadmium chloride for three weeks and harvested. The harvests were measured regarding the weight and root length. The TaTM20 over-expression plant outgrew the wild one in a ½ MS medium including 40 or 60 μM cadmium chloride as shown in FIGS. 8A and 8B. In addition, it turned out to have more excellent biomass and root length than those of the wild one in a medium treated with a lower concentration of 15 μM and 25 μM cadmium chloride as shown in FIGS. 8C and 8D. Accordingly, these results indicate that TM20 can improve cadmium resistance in a plant.

Figure 11A:
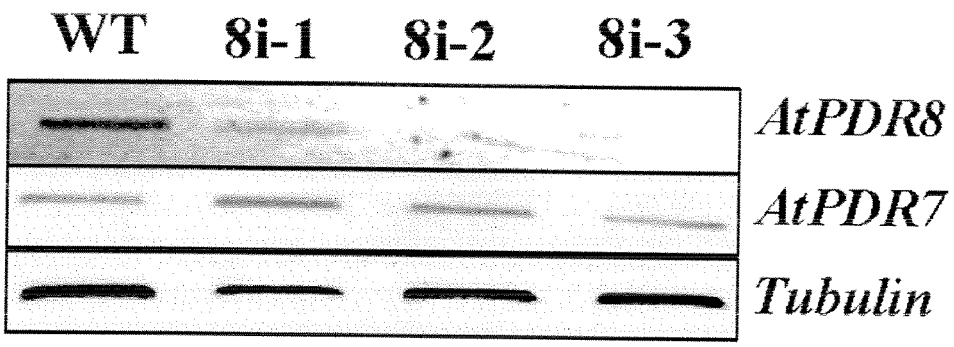
FIGS. 11A to 11E show that transformed Arabidopsis having reduced AtPDR8 expression is very sensitive to cadmium. AtPDR8 gene expression of a transgenic plant transformed with AtPDR8-RNAi is confirmed by RT-PCR (A); shows growth (B), chlorophyll contents (C), and biomass (D) of the transgenic plants when they are cultured in a medium including cadmium; and shows comparison of cadmium sensitivity of a wild type and AtPDR8-deficient plant (E).
Figure 11B:
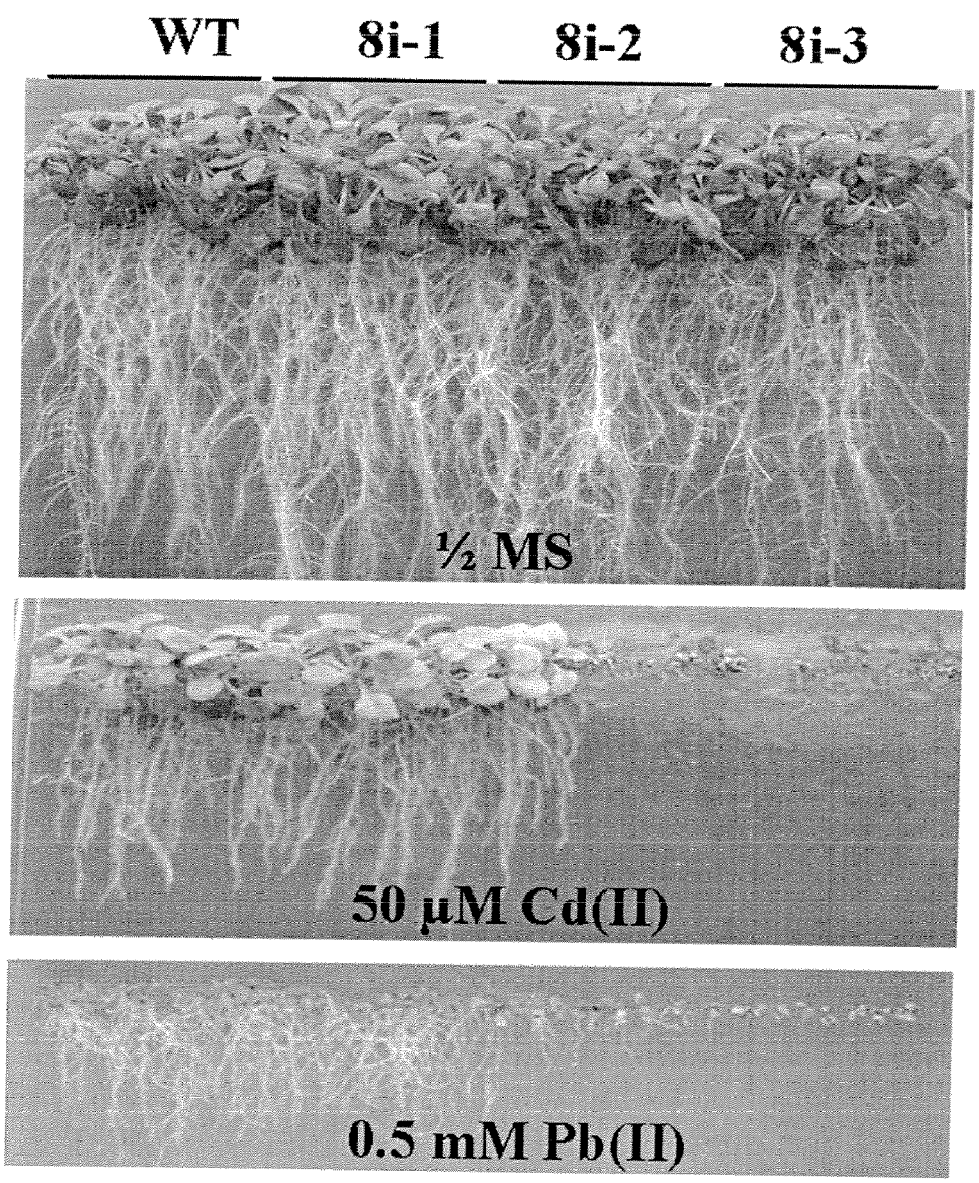
Figure 11C:
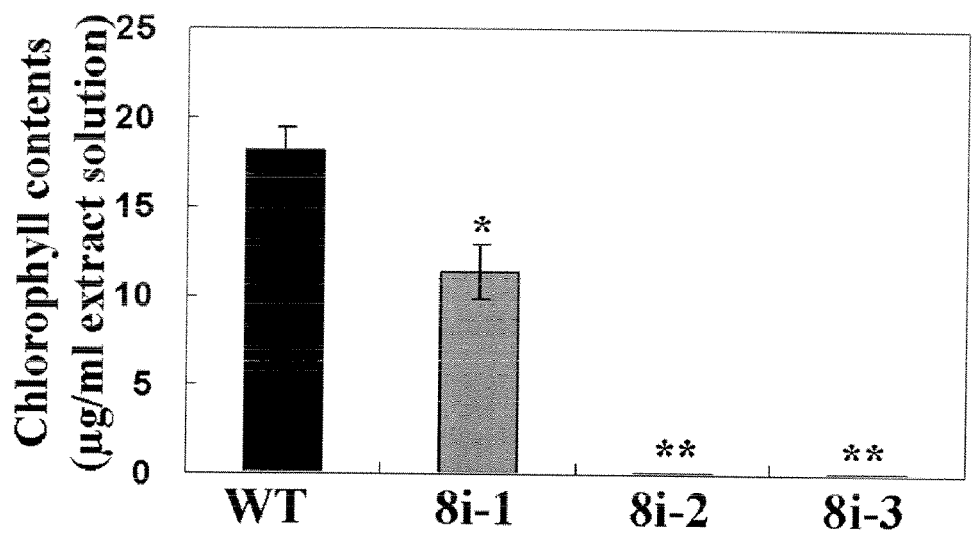
Figure 11D:
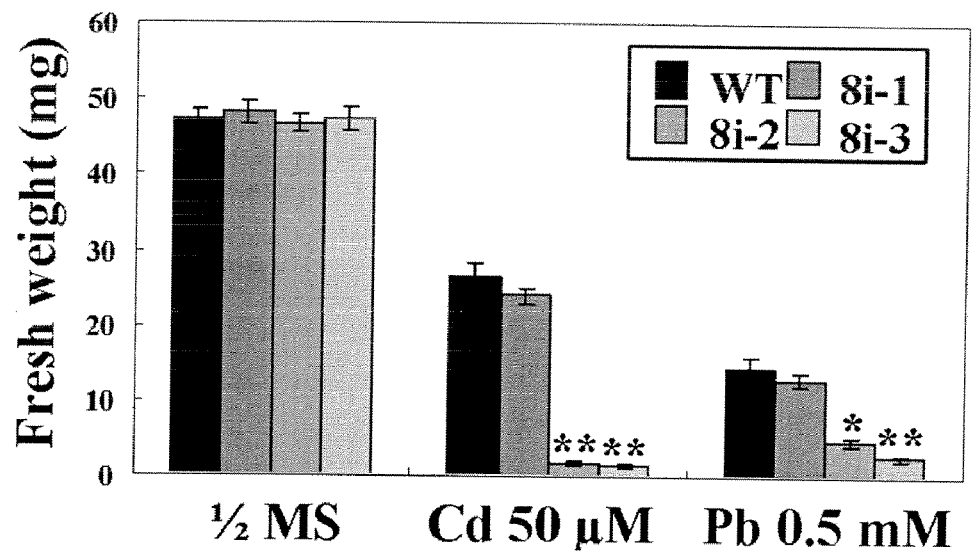
Figure 11E:
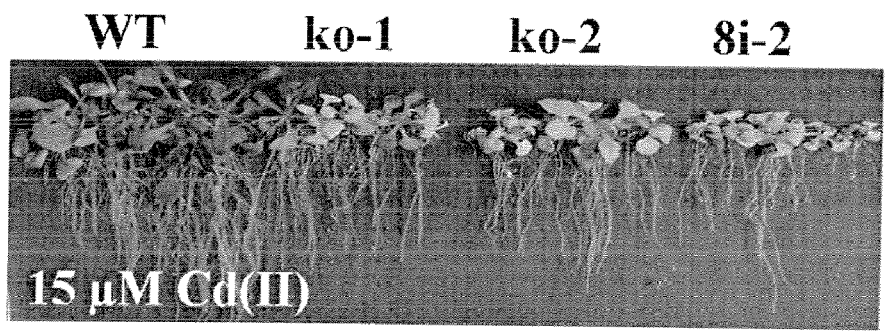

Wild-type and AtPDR8-transformed Arabidopsis (overexpression and expression-suppressing plants) were planted in a ½ MS medium including 30 μM to 50 μM cadmium chloride and vertically incubated for 2 to 3 weeks and then, harvested. The harvests were measured regarding the biomass and root length of the plants. In addition, wild-type and AtPDR8 over-expression plants (PDR8-1, -2, -3) were all incubated in a medium including 40 μM cadmium chloride and 0.4 mM lead nitrate. As a result, the AtPDR8 over-expression plant had more excellent biomass and root length than the wild one as shown in FIG. 10. Furthermore, an AtPDR8 expression-suppressing plant (RNAi; 8i-1, -2, -3) and an AtPDR8-deficient mutant (knock-out; ko-1 and ko-2) were incubated with a wild-type one in a medium including cadmium chloride and lead nitrate. As a result, the AtPDR8 expression-suppressing plant and the AtPDR8 deficient mutant were sensitive to cadmium and lead (FIGS. 11A, 11B, and 11E) and had sharply-decreased amount of chlorophyll and bio-mass (FIGS. 11C and 11D). Accordingly, these results indicate that AtPDR8 can improve resistances against cadmium and lead in a plant.

EXAMPLE 6

Examination of Cadmium Resistance Mechanism

Figure 12:
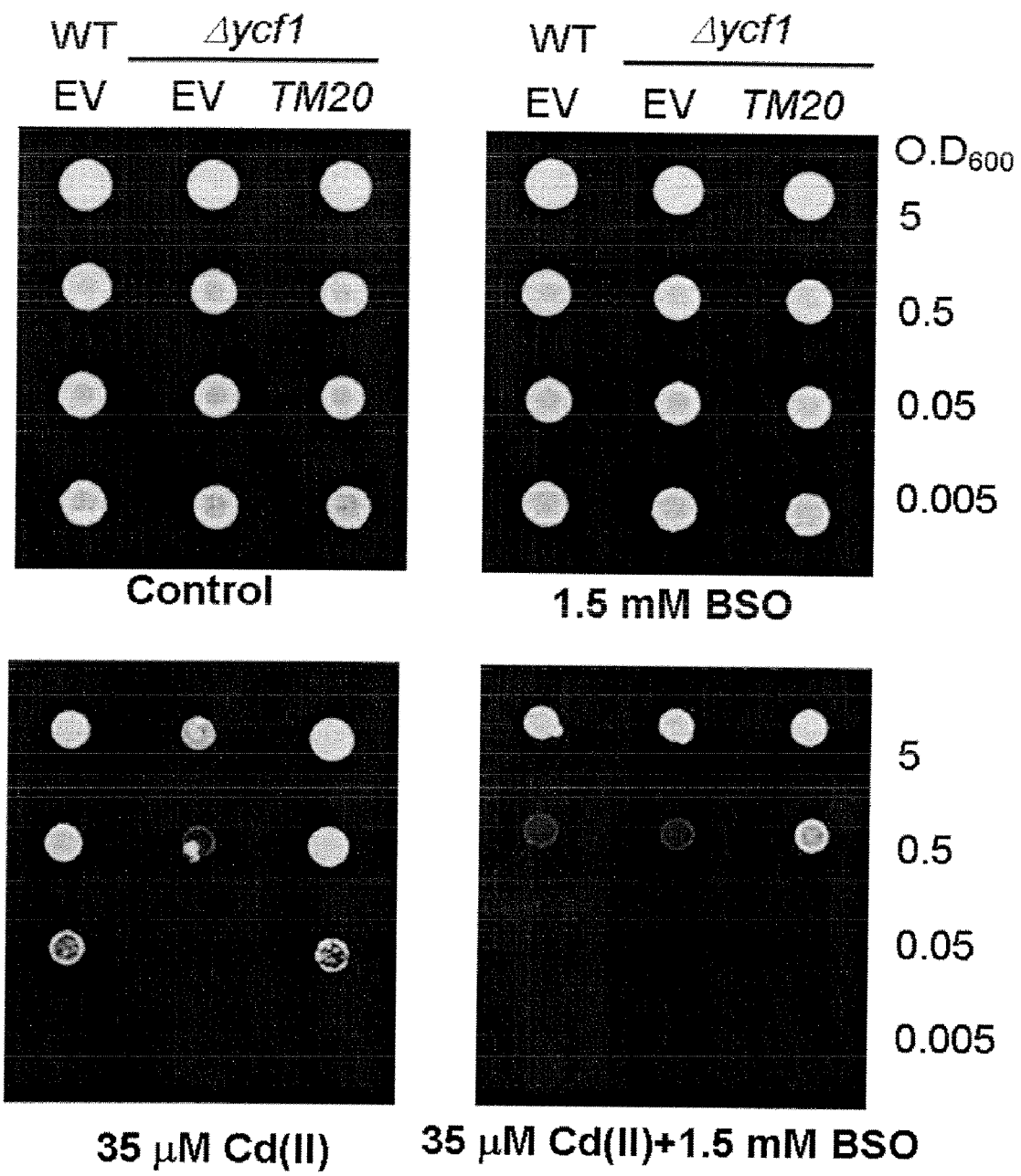
FIG. 12 shows that cadmium resistance conferred by TaTM20 is maintained in a TaTM20 over-expressing yeast even though glutathione is reduced in a cell by treatment of glutathione synthesis inhibitor, BSO.

BSO (buthionine sulfoximine) as a glutathione synthesis inhibitor was used to examine cadmium resistance and thereby, to see if TaTM20 and AtPDR8 cadmium resistance mechanism is related to glutathione. TaTM20-transformed yeast grew similar to the one inserted with an empty vector in a medium not including cadmium or BSO and one including only BSO. Accordingly, the TaTM20 transformed yeast turned out to have much increased cadmium resistance in a medium including cadmium. In addition, when it is incubated in a medium including cadmium and BSO, its cadmium resistance due to TaTM20 did not disappear but was maintained as shown in FIG. 12. Cadmium resistance of yeast is conventionally known to increase through glutathione but the above results indicate that cadmium resistance of yeast can be contributed by TaTM20 in a different mechanism from a conventional glutathione-mediated one.

Figure 13A:
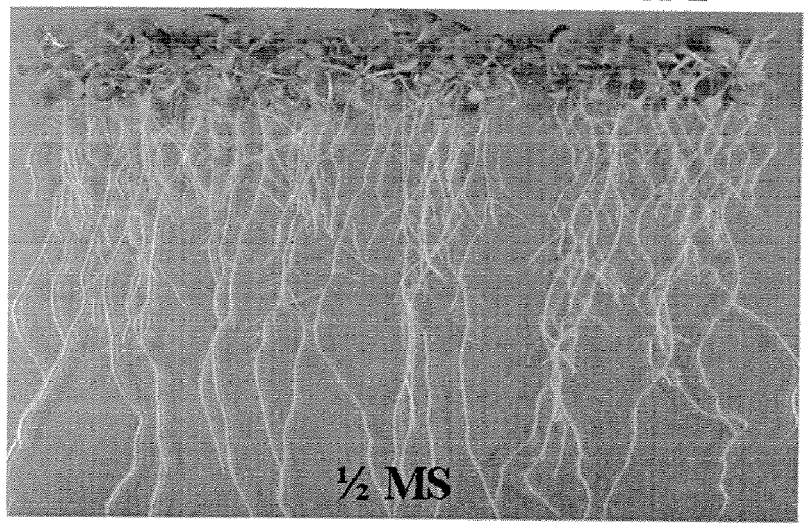
FIGS. 13A to 13D shows growth (A, B, and C) and biomass and root lengths (D) showing that cadmium resistance modified by AtPDR8 is maintained when an AtPDR8 over-expression plant (PDR8-1), a wild type (wt), a low-expression plant (8i-2) are incubated after treatment of glutathione synthesis inhibitor, BSO and cadmium.
Figure 13A:
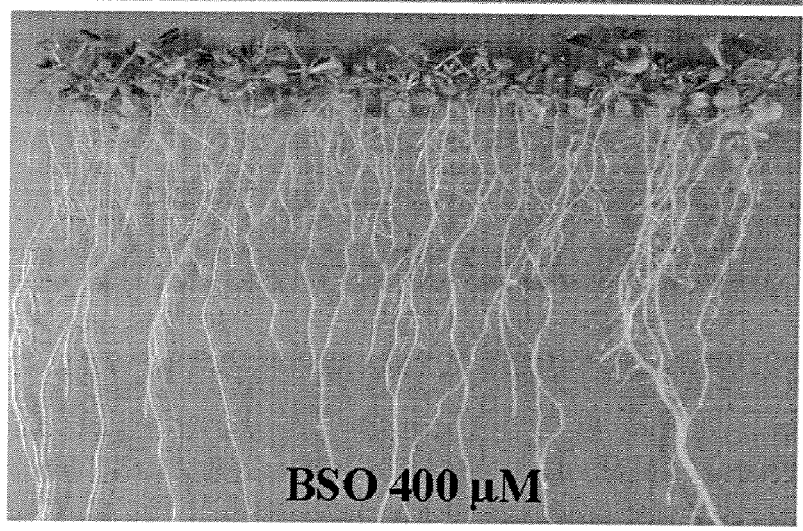
Figure 13B:
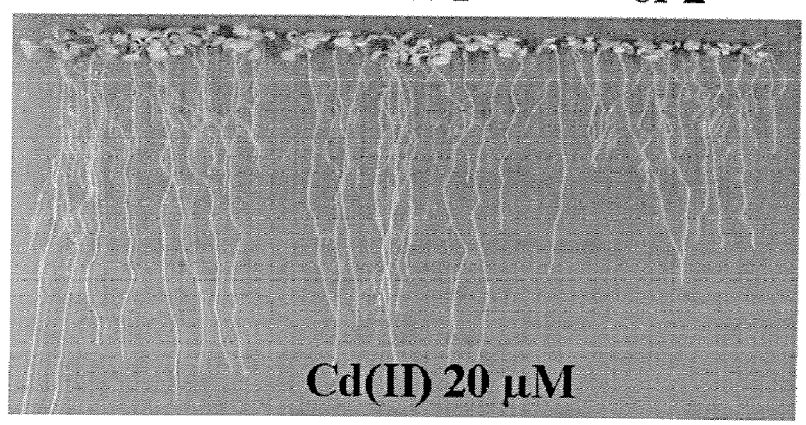
Figure 13C:
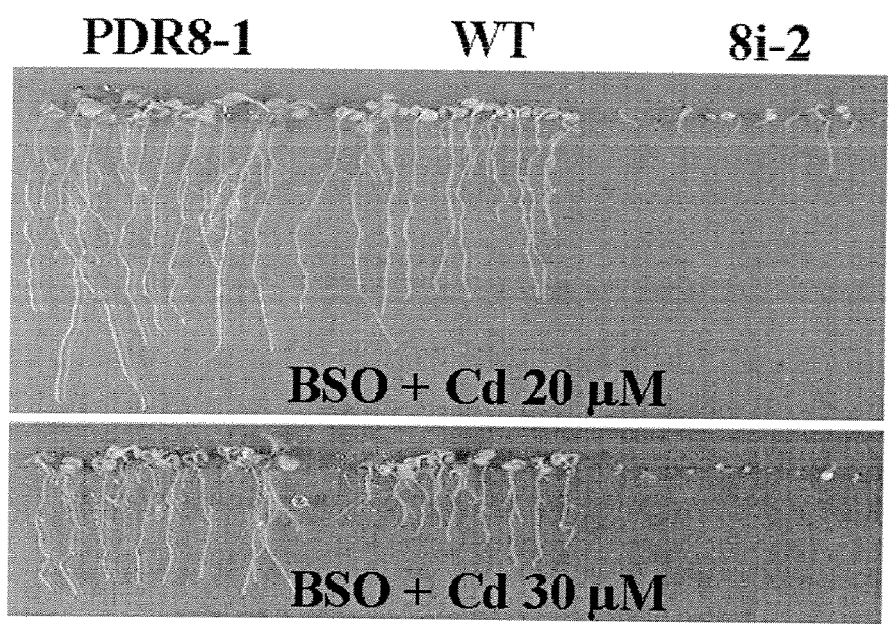
Figure 13D:
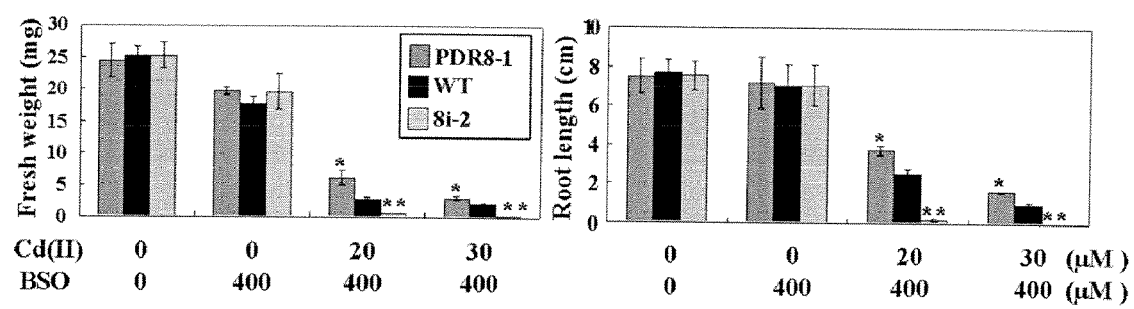

As for AtPDR8, a transgenic plant grew equivalently to a wild-type one in a ½MS or another ½ MS including only BSO (FIG. 13A). However, an overexpression plant grew outstandingly in a medium including cadmium, and an expression-suppressing plant turned out to be a sensitive phenotype (FIG. 13B). On the other hand, AtPDR8 transgenic and wild-type plants had increased growth difference in a medium treated with cadmium as well as BSO (FIGS. 13C and 13D). These results indicate that cadmium resistance due to AtPDR8 can differ from resistance mechanism due to glutathione.

EXAMPLE 7

Measurement of the Amount of Cadmium

Figure 14A:
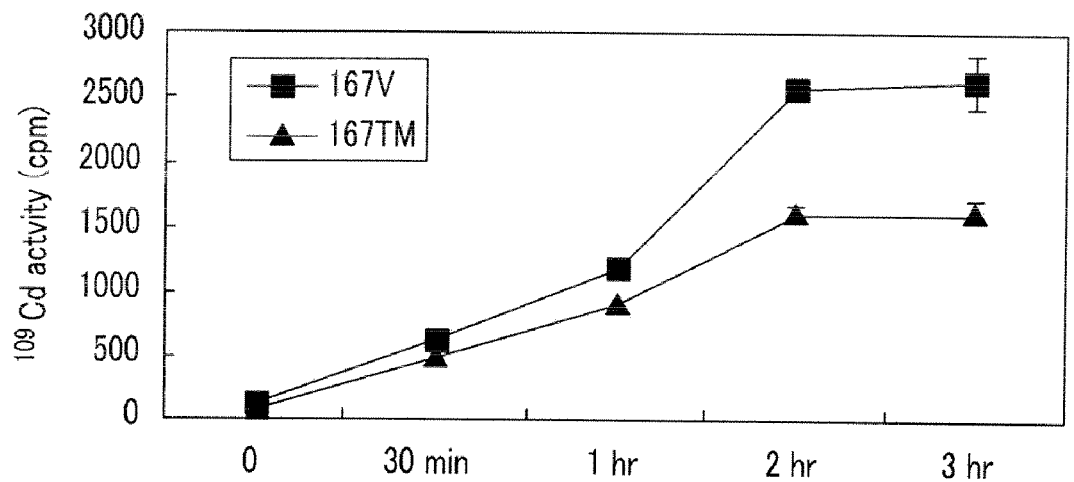
FIGS. 14A to 14C show that TaTM20 transformed yeast uptakes a small amount of cadmium and releases cadmium well. It shows measurement results of cadmium uptake (A and C), and release (B) in a wild type yeast and a TaTM20 transformed yeast using a cadmium Isotope and atomic absorption spectrometry.
Figure 14B:
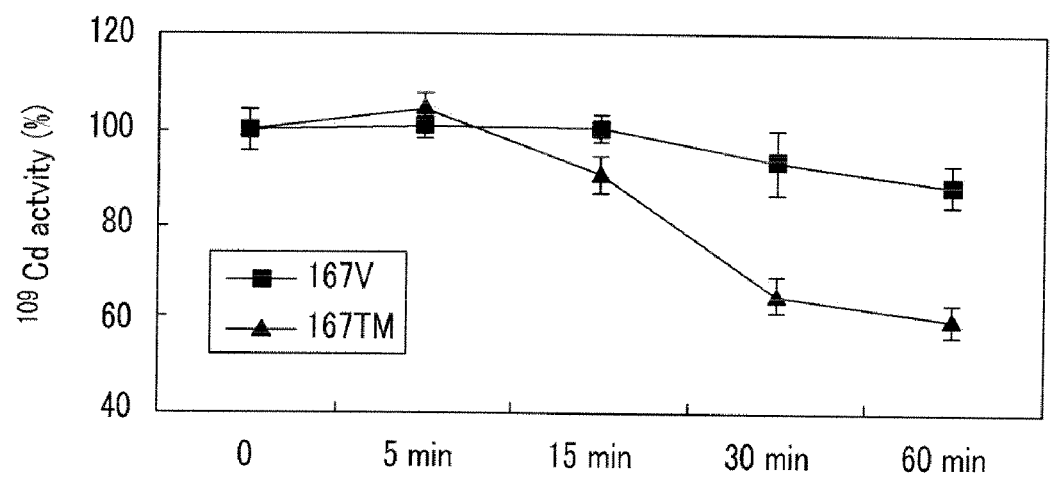
Figure 14C:
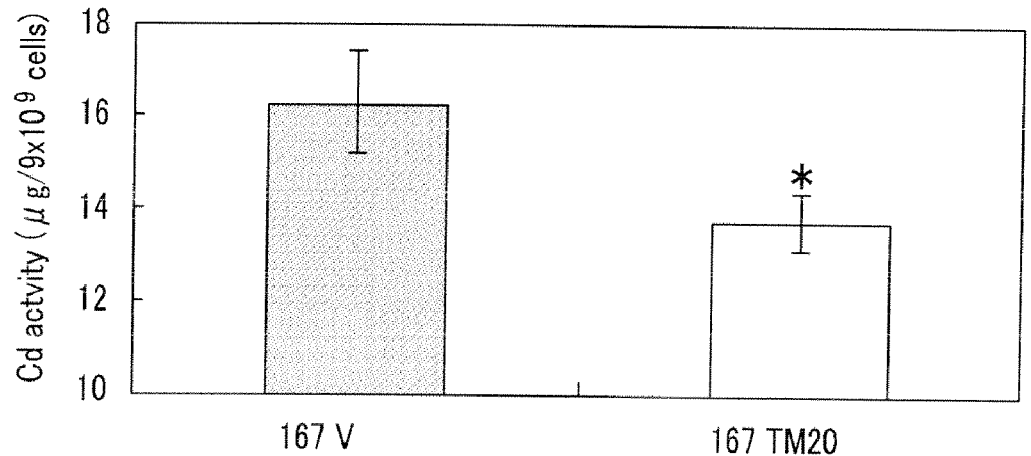

TaTM20 transformed yeast was incubated in a synthetic galactose medium (SG-ura) and treated with 10 μM cadmium chloride and 1 μM radioactive cadmium chloride. Cells were harvested from the TaTM20 transformed yeast at every hour to measure the amount of cadmium with a gamma-ray counter. Compared with ycf-null yeast (167V) injected with an empty vector, the yeast (167TM) injected with TaTM20 included small amount of cadmium inside the cell (FIG. 14A). However, based on measuring their releasing degree of cadmium, the TaTM20 yeast (167™) released cadmium faster than the ycf-null yeast (167V) did (FIG. 14B). In addition, yeasts were raised in a SG-Ura medium treated with 20 μM cadmium chloride, washed with ice water, and then, treated with 11 N nitric acid to dissolve the cells. Then, the amount of cadmium inside the transformed yeast cell was analyzed with an atomic absorption spectrometry (AAS). As a result, the transformed yeast turned out to include smaller amount of cadmium due to TaTM20 than the one injected with empty vector. The reason is that TaTM20 pumped out cadmium entering the cells and thereby, increased cadmium resistance of yeasts.

Figure 15A:
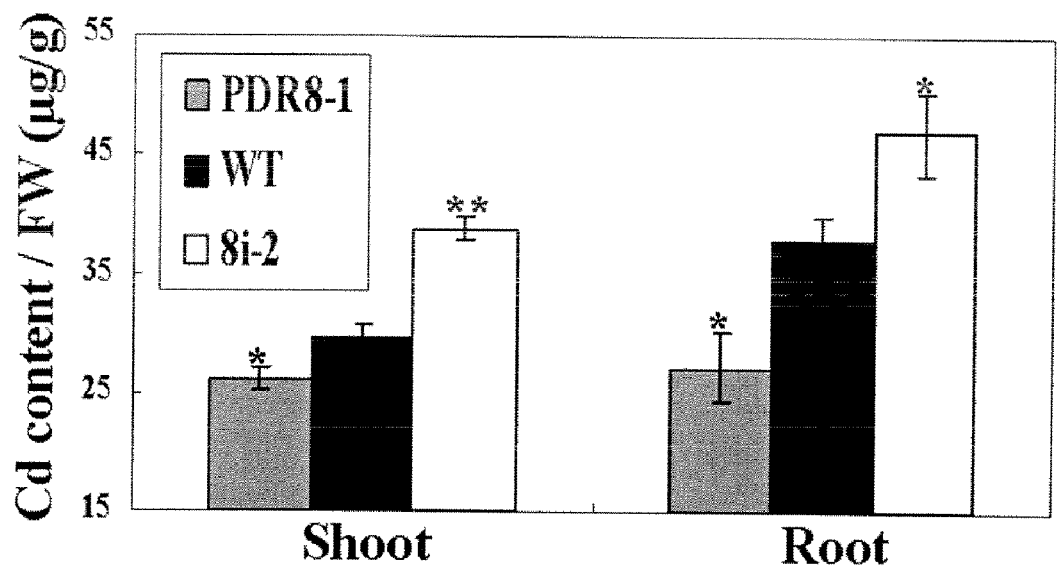
FIGS. 15A and 15B show that AtPDR8 reduces cadmium content in a plant. It is results of cadmium contents of an over-expression plant (PDR8-1), a wild type (wt), and a low-expression plant (8i-2) measured using atomic absorption spectrometry (A) and cadmium Isotope (B).
Figure 15B:
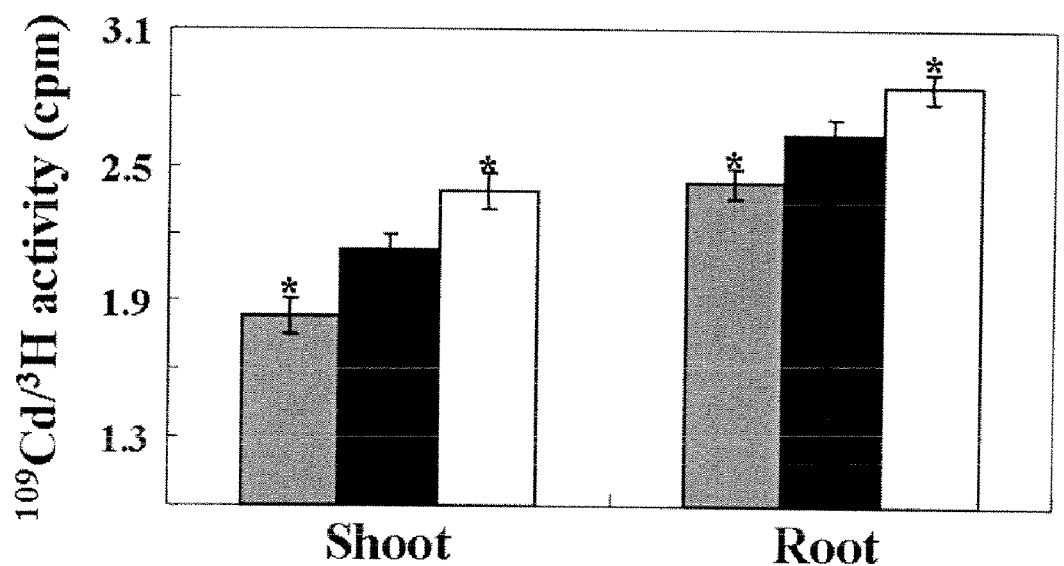

On the other hand, an AtPDR8 transgenic plant was measured regarding the amount of cadmium inside the cell, after it was vertically incubated in a ½ MS for 2 weeks, its root was treated with 100 μM cadmium chloride, and it was incubated again for 10 hours. Then, its shoot region and root were respectively separated and harvested. The harvests were washed with cold water and dried. The dried plant was measured regarding the amount of cadmium by using AAS according to the same method as aforementioned. The shoot and root of the AtPDR8 over-expression plant (PDR8-1) included smaller amount of cadmium than the wild-type one. However, the shoot and root of the AtPDR8 expression-suppressing plant (8i-2) included plenty of accumulated cadmium (FIG. 15A). In addition, the amount of cadmium in the plants was analyzed by using a cadmium isotope element. Plants, which vertically incubated in a ½ MS for 10 days, were incubated in a medium including radioactive cadmium chloride for 10 hours and well washed. Then, their shoots and roots were separated to analyze the amount of cadmium with a gamma-ray device. As a result, the AtPDR8 over-expression plant included smaller amount of cadmium in the shoot and root than a wild-type one, but the AtPDR8 expression suppressing plant included lots of accumulated cadmium in its shoot and root.

Figure 16A:
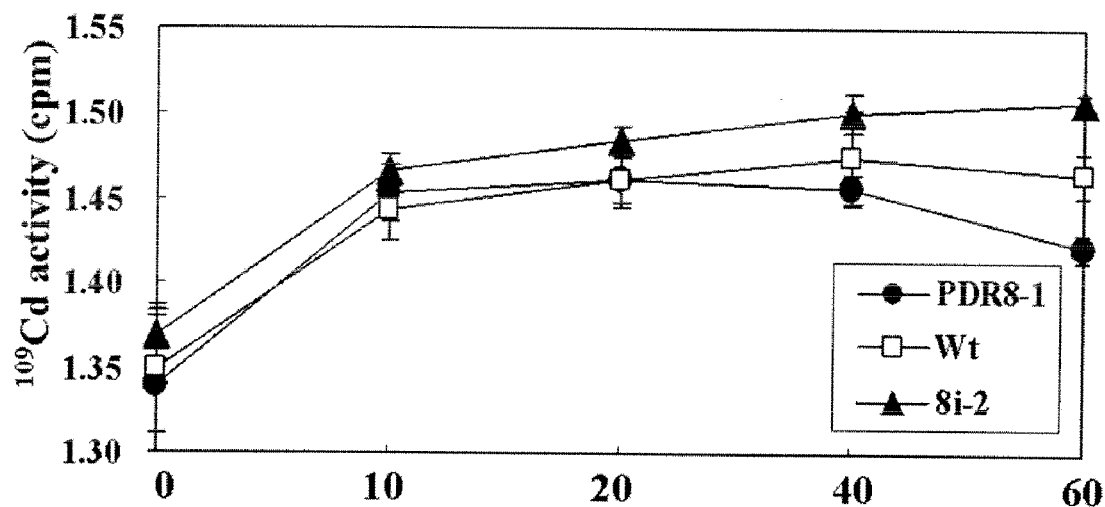
FIGS. 16A and 16B show that AtPDR8 improves cadmium release of a plant cell. It is results of cadmium content variation in cells when protoplasts separated from an over-expression plant (PDR8-1), a wild type (VA), and a low-expression plant (8i-2) are placed in cadmium Isotope-containing mediums (A and B).
Figure 16B:
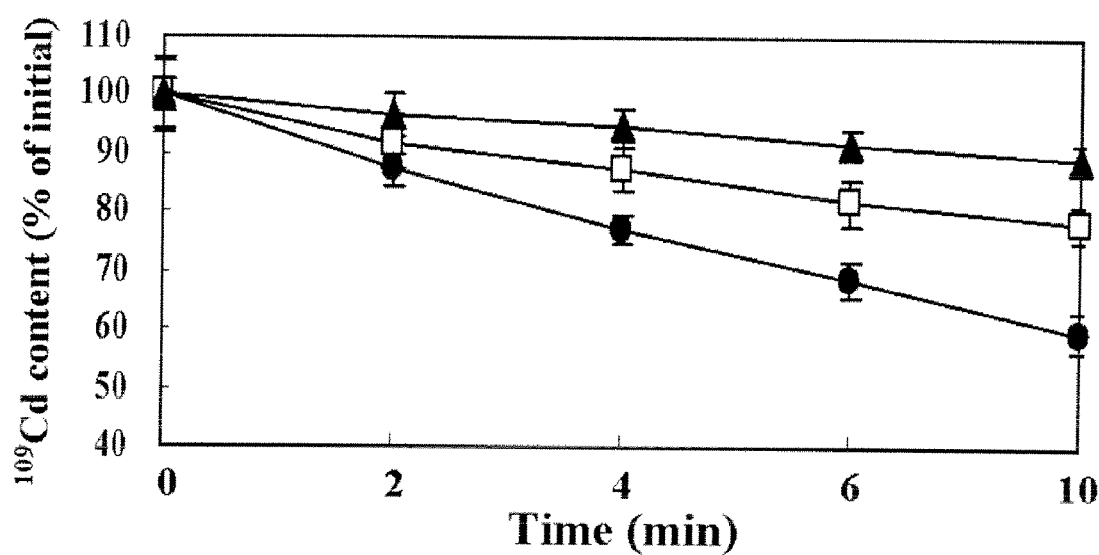

Then, cadmium transportation capability of AtPDR8 was measured. Cadmium isotope element was absorbed into a protoplast of an AtPDR8 transgenic plant, and the amount of cadmium inside the cell was measured. In other words, a cadmium isotope element was incubated with a protoplast. The protoplast was harvested at every hour to measure the amount of cadmium inside the cells. Compared with a protoplast acquired from a wild-type one (wt), the protoplast acquired from an over-expression plant (PDR8-1) had smaller amount of cadmium. However, a protoplast of an expression-suppressing plant (8i-2) had a larger amount of accumulated cadmium in as shown in FIG. 16A. In addition, their capability of releasing cadmium was examined. A cadmium isotope element was incubated with a protoplast together. After cadmium outside the cell was washed off, the amount of the remaining cadmium inside the cell was measured at each hour. As a result, the over-expression cell turned out to release cadmium faster than a wild-type one, but the expression-suppressing cell released cadmium slower than the wild-type one (FIG. 16B). This result means that AtPDR8 tends to pump out cadmium entering inside a cell and thereby, improves cadmium resistance of a plant.

Accordingly, an AtPDR8-overexpression transgenic plant can be resistant against cadmium and lead and thereby, release them out of itself. Herein, AtPDR8 plays a role of decreasing the amount of a heavy metal inside a plant and changing the plant safe. On the contrary, a transgenic plant suppressed from expression of AtPDR8 or a gene similar to it has decreased releasing function and thereby, cannot but include increased amount of a heavy metal. Accordingly, the plant can be used for purifying the environment.

EXAMPLE 8

Measurement of the Amount of Chlorophyll

When a plant is poisoned with a heavy metal such as cadmium, lead, and the like, it generally tends to be sulfide in leaves. Accordingly, a plant's resistance against these heavy metals can be examined through analysis of the amount of chlorophyll. The amount of chlorophyll in a plant was measured by gathering a leaf and performing an extraction at 80° C. for 20 minutes with 95% ethanol. The extract was measured regarding the absorbance at 664 nm and 648 nm. Then, the amount of chlorophyll A and B was calculated (Oh S A, Park J H, Lee G I, Paek K H, Park S K, Nam H G 1997 Identification of three genetic loci controlling leaf senescence in Arabidopsis thaliana. Plant J. 12, 527-35). In other words, AtPDR8 expression-suppressed transgenic plants (8i-1, 8i-2, and 8i-3) and a wild-type plant were incubated in a medium treated with 50 μM cadmium chloride for 3 weeks. Then, their amounts of chlorophyll were measured. As a result, the AtPDR8 expression-suppressing transgenic plants included a smaller amount of chlorophyll than the wild one as shown in FIG. 11C. Accordingly, these results indicate that AtPDR8 expression can contribute to a plant's resistance against cadmium.

EXAMPLE 9

Examination of Salt and Drought Resistances and the Amount of the Salt

Figure 17A:
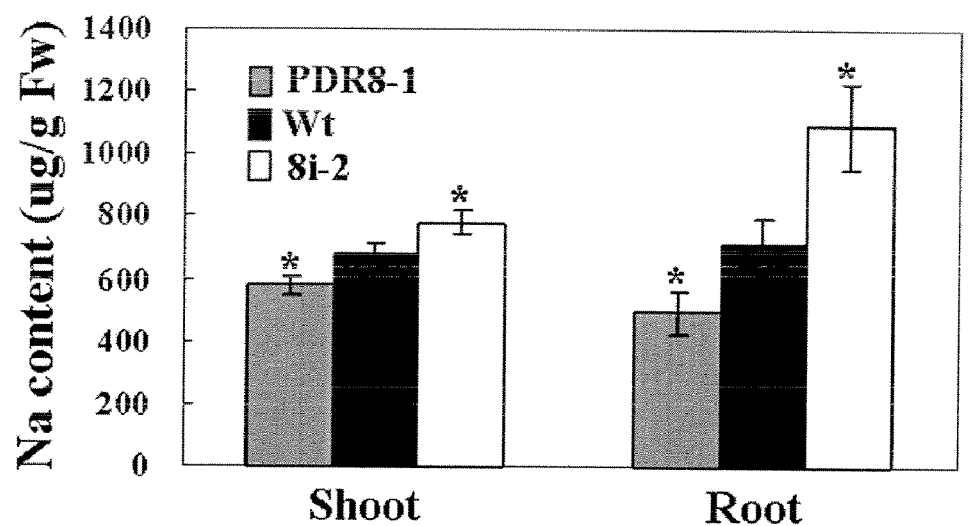
FIGS. 17A to 17F show that AtPDR8 improves salt and drought resistance of a plant. When an over-expression plant (PDR8-1), a wild type (wt), low-expression (8i-2), and a deficiency mutant (P8 ko-1) plant are cultured, it shows salt contents in a plant (A); growth (B) and root lengths (C) of an over-expression plants in a medium including an excessive amount of salt; and growth (D and F), biomass (E) of plants when they are cultured in a drought stress condition.
Figure 17B:
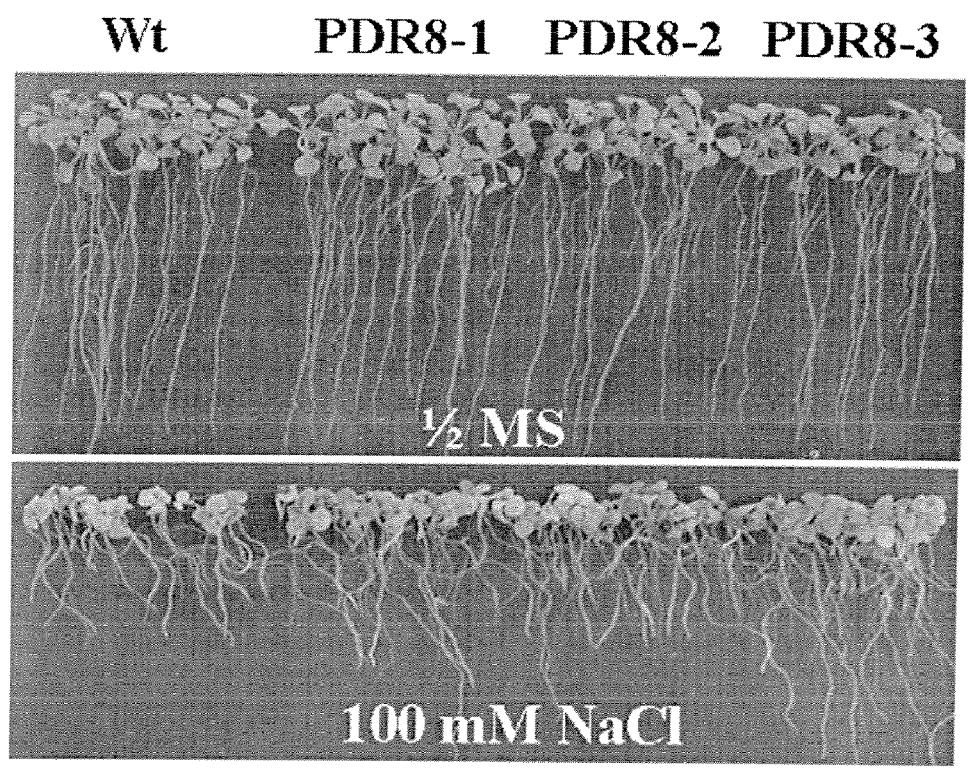
Figure 17C:
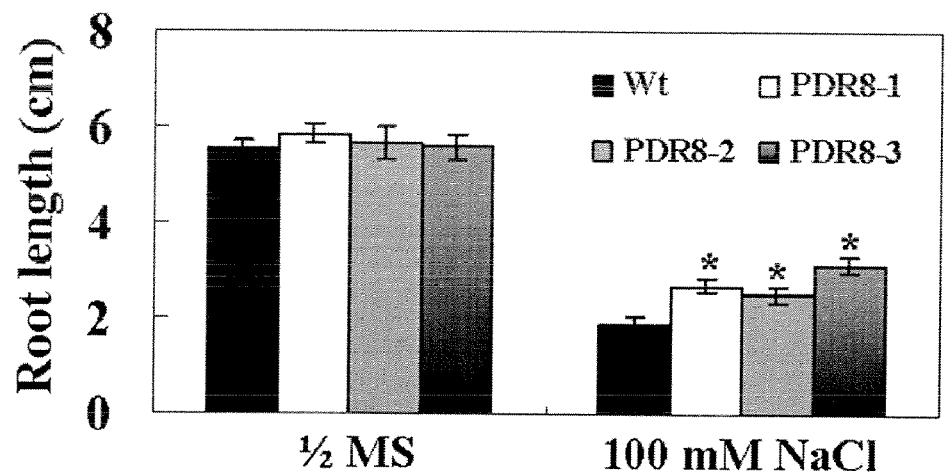
Figure 17D:
Figure 17E:
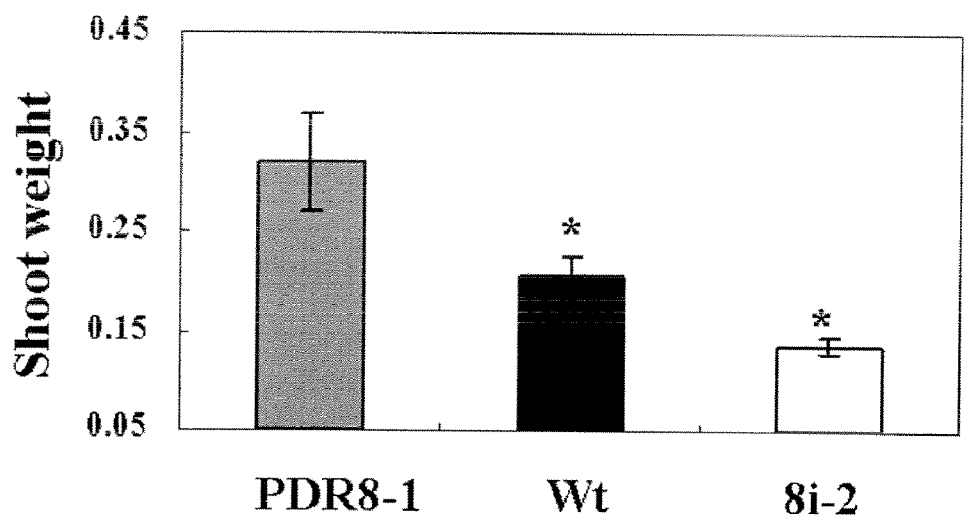
Figure 17F:
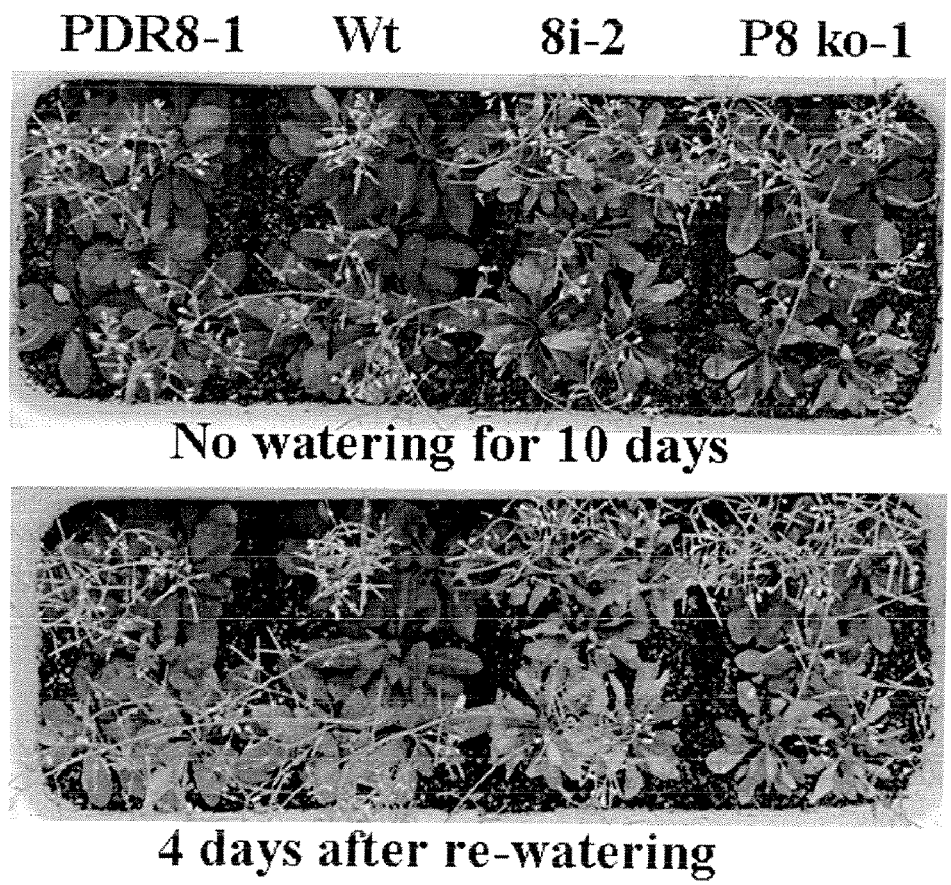

An AtPDR8 transgenic plant was experimented regarding resistances against base and drought stresses. An over-expression plant, a wild-type plant, and an expression-suppressing plant were incubated to measure the amount of base therein. The over-expression suppressing plant turned out to include less amount of base than the wild one, but the expression-suppressing plant included more amount of base than the wild one (FIG. 17A). In addition, the wild type and over-expression plants were incubated in a ½ MS medium including 100 mM chloride sodium for 3 weeks. Examining their root lengths and leaf colors, the over-expression plant turned out to have increased salt resistance unlike the wild-type one (FIGS. 17B and 17C). Then, AtPDR8 transgenic plants were examined regarding resistance against drought stress. They were incubated in the soil for 4 weeks and then, kept being incubated for 2 weeks with watering (+) or without watering (−) (FIG. 17D). Or, they were incubated in the soil for 3 weeks and then, not watered for 10 days, and then, watered again for 4 days for examination of their growth (FIG. 17F). As a result, the AtPDR8 over-expression plant outgrew the wild one, but expression-suppressed and mutant plants grew less than the wild one (FIG. 17E). Based on the above result, a plant highly-expressing an AtPDR8 gene had a less-accumulated base than the other ones and thereby, high resistance against base and drought.

Figure 21:
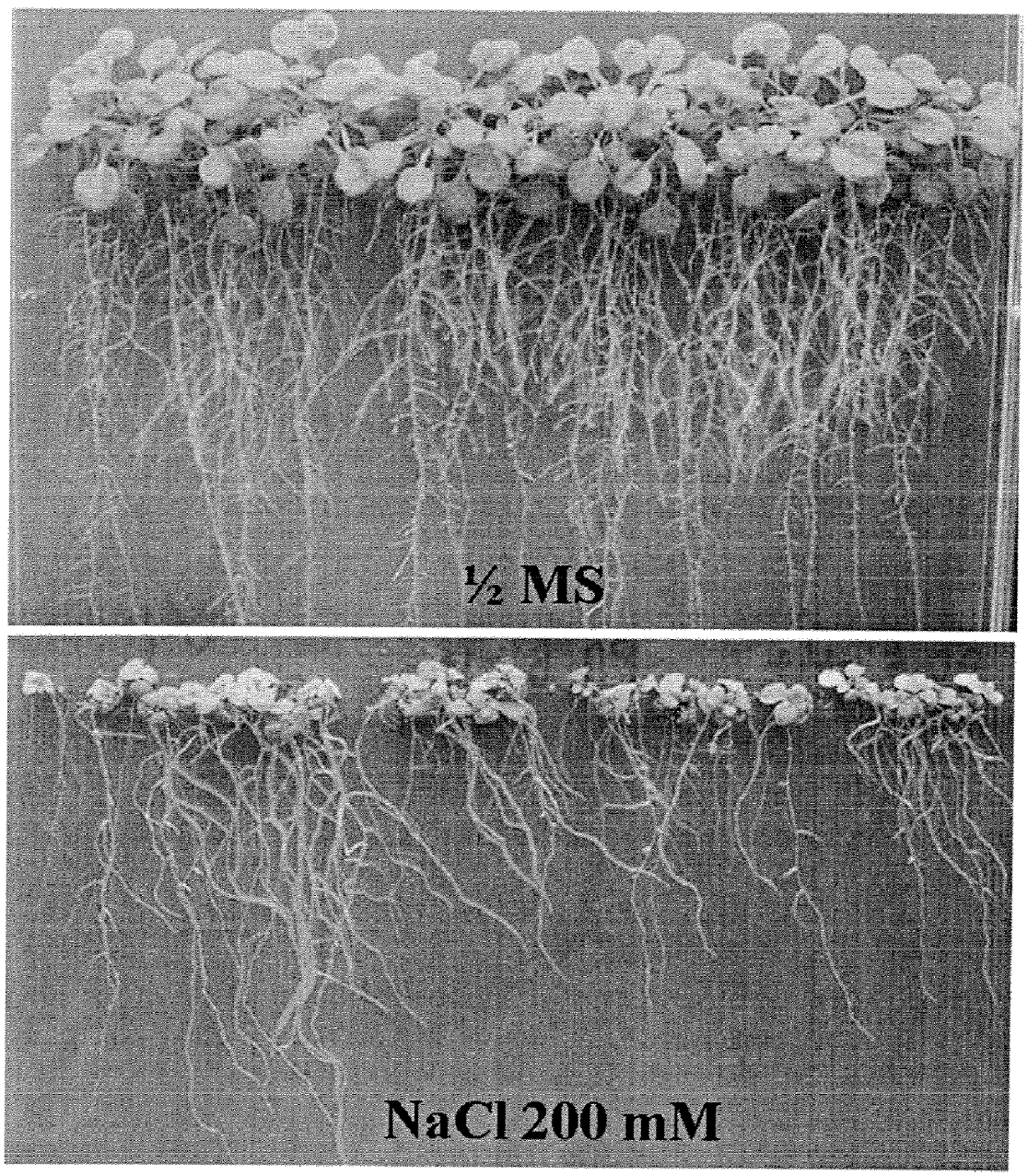
FIG. 21 shows that AtPDR7 mediates salt stress resistance. An AtPDR7 deficiency mutant plant is little grown compared to wild type when culturing it in an excessive amount of salt.

Furthermore, AtPDR7 with a similar base sequence to AtPDR8 was examined regarding its relation to resistance against base stress. AtPDR7-deficiency mutant plants (PDR7 k0-1, -2) were incubated in a ½ MS medium and another ½ MS medium including 200 mM chloride sodium for 3 weeks. As a result, the mutant plant lack of an AtPDR7 gene turned out to be a very sensitive phenotype unlike the wild-type one, when it was overly-treated with base (FIG. 21). The AtPDR7 had 80% similar base sequence to the AtPDR8. The mutant plants respectively lacking of these genes realized a sensitive phenotype. Accordingly, when genes with high similarity were highly expressed in a plant, the plant can be developed to have stronger base resistance than a wild-type one.

EXAMPLE 10

Introduction of GFP::TaTM20 and GFP::AtPDR8 into an Arabidopsis Protoplast

A TM/GFP-F primer (5'-AAGMGCTTATGGAGTGTG-GTGGC-GTCTCC G-3') (SEQ ID NO: 9) and a TM/GFP-R primer (5'-TAGAAGCTTAGAACTACACTACAGAGCTG CT-3') (SEQ ID NO: 10) were used to prepare a GFP:TaTM20 fused gene.

The GFP::TaTM20 can be prepared by inserting an amplified gene into HindIII site of a 326-GFP vector and is expressed under regulation of a CaMV35S promoter. In addition, as for AtPDR8, an AtPDR8 gene in a T-vector was cut into restriction enzymes and then, transferred to a 326GFP-3G vector, preparing GFP::AtPDR8. On the other hand, plasmid was introduced inside an Arabidopsis protoplast through PEG medium transformation method (Jin et al., 2001). The expression of GFP fused protein was examined with a fluorescent microscope 16 to 24 hours later, after it was transformed into a protoplast. In addition, the expressed protein was identified regarding its location by respectively separating cytoplasm and plasma membrane protein from a transformed Arabidopsis protoplast and then, performing a western blot thereto with GFP antibody.

Figure 2A:
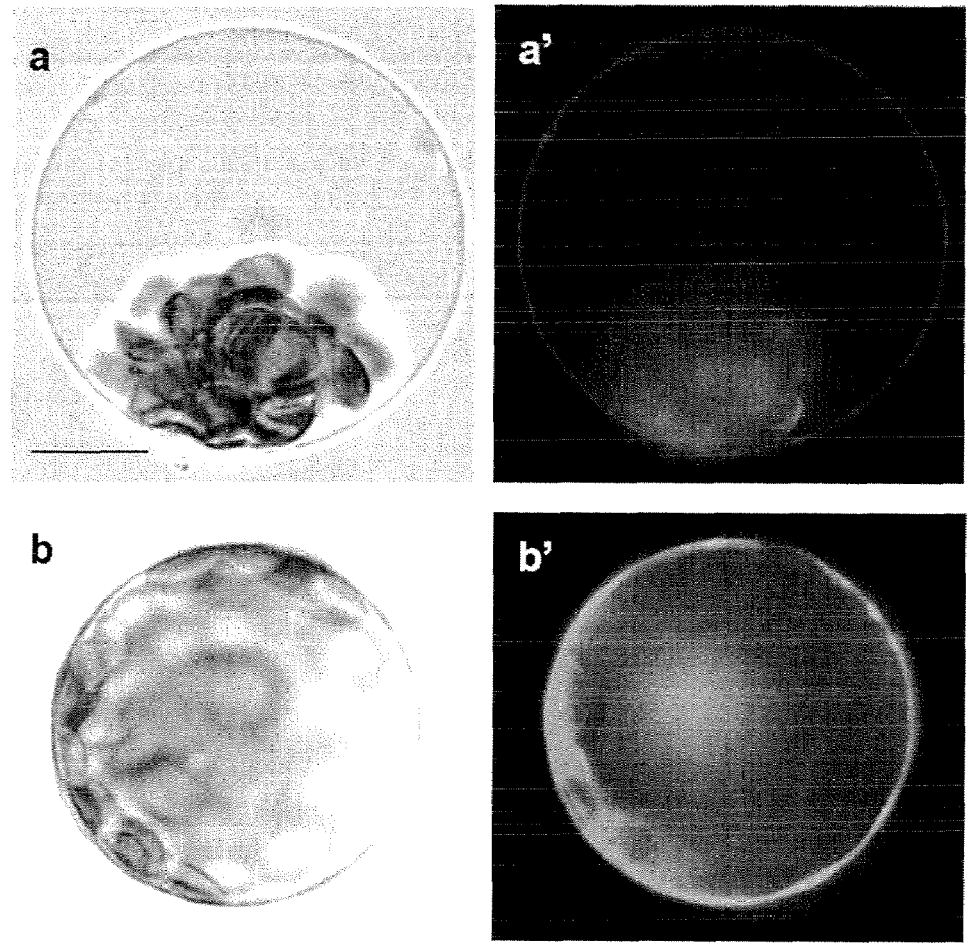
FIGS. 2A and 2B are photographs showing that a TaTM20 protein is positioned in a plant cell membrane. Green fluorescence shows that a GFP (green fluorescent protein)-TaTM20 fusion protein is expressed in a plant cell membrane (A) (a, b- bright field image) (a', b'-GFP images), and western blotting using a GFP antibody shows that the GFP-TaTM20 fusion protein is positioned in a cell membrane (B).

The results are shown in FIGS. 2A to 3B. FIG. 2A is a photograph showing where GFP (a green fluorescent protein)-TaTM20 fused protein expressed from a plant protoplast was expressed and that a GFP-TaTM20 protein existed on a plasma membrane of the protoplast and FIG. 2B is a photograph showing that the GFP-TaTM20 protein existed not on cytoplasm but a membrane when it was identified with a western blotting. FIG. 3A is a photograph showing where a GFP-AtPDR8 fused protein was expressed and FIG. 3B indicates its local expression using a western-blot method. Based on the results, the GFP-AtPDR8 protein was identified to exist on a plasma membrane of a protoplast.

EXAMPLE 11

RNA Identification

The total RNA of a plant was extracted from wheat incubated for 20 days or Arabidopsis incubated for 2 to 3 weeks by using trizol. In other words, the plants were incubated in a ½ MS for 2 to 3 weeks and then, evenly ground by using liquid nitrogen. Then, their total RNA was separated by using trizol, and the separated RNA was used for a northern blotting, RT-PCR, and the like.

EXAMPLE 12

RT-PCR

5 μg of RNA was synthesized with cDNA by using a Powerscript RT (reverse transcription)-kit (BD Bioscience Clontech) and an oligo dT primer. Then, PCR reaction was performed from 2 μl of cDNA, and specific primers were used for each TaTM20, AtPDR8, and AtRop2. As for wheat as a control, G3PDH (glycerolaldehyde-3-phosphate dehydrogenase) gene was used, while as for Arabidopsis, beta-tubuline and actin were used.

Figure 7A:
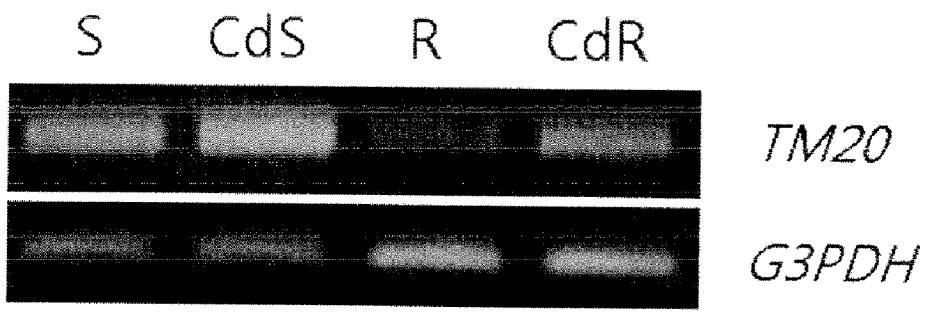
FIGS. 7A and 7B show that cadmium-treatment of a wheat increases expression of TaTM20 in leaves and roots of the wheat by RT-PCR (A) and realtime-PCR (B).
Figure 7B:
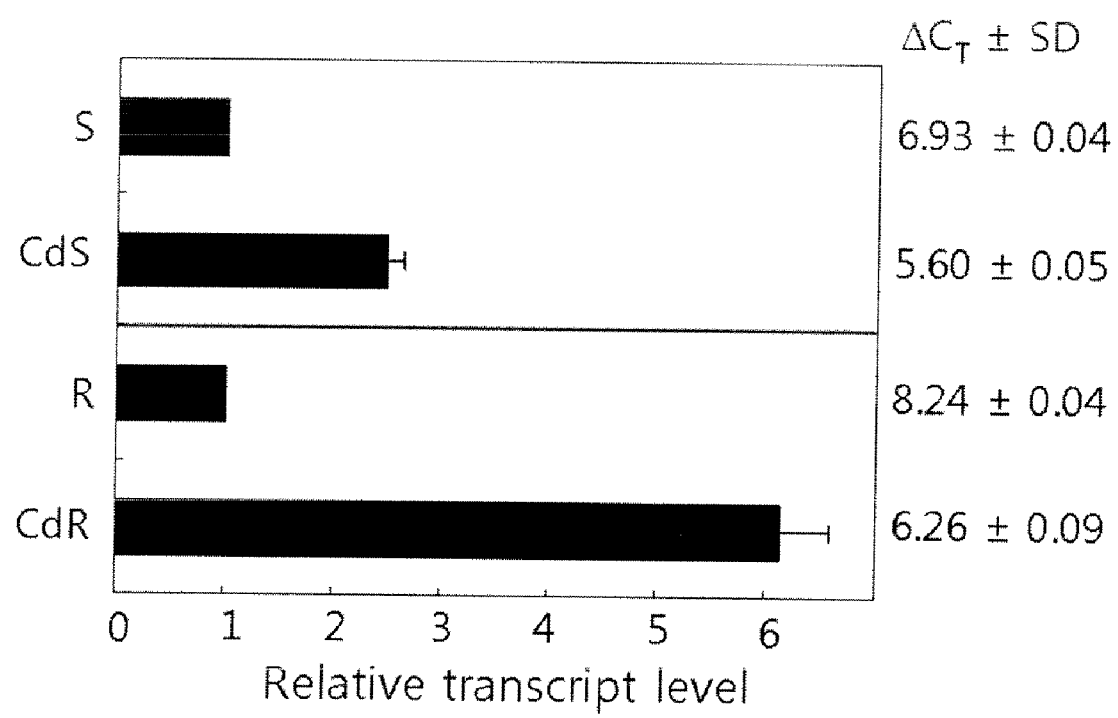

Then, expression of a TaTM20 gene due to a heavy metal was examined. First of all, a wheat root was treated with cadmium and synthesized with cDNA. Then, the resulting product was used as a template to perform PCR by using a TaTM20) RTF primer (5'-AAGGGTTGCTCCTCTTCGC-GATCTTG-3') (SEQ ID NO: 11) and a TaTM20) RTR primer (5'-GTACATGCCAG CACCGTATGGATTG-3') (SEQ ID NO: 12). As a result, the TaTM20 gene was expressed in a shoot region (CdS) and a root (CdR) by cadmium (FIG. 7A). Furthermore, real time-PCR was performed to identify expression of TaTM20 due to cadmium (FIG. 7B). Expression of a G3PDH (glyceraldehyde-3-phosphate dehydrogenase) gene was identified by using a TaG3PDHF (5'-CM-CGCTAGCTGCACCACTAACT-3') primer (SEQ ID NO: 13) and a TaG3PDHR primer (5'-ACTCCTCCTTGATAG-CAGCCTT-3') (SEQ ID NO: 14) as controls. As a result, this gene was not changed by cadmium.

Figure 9A:
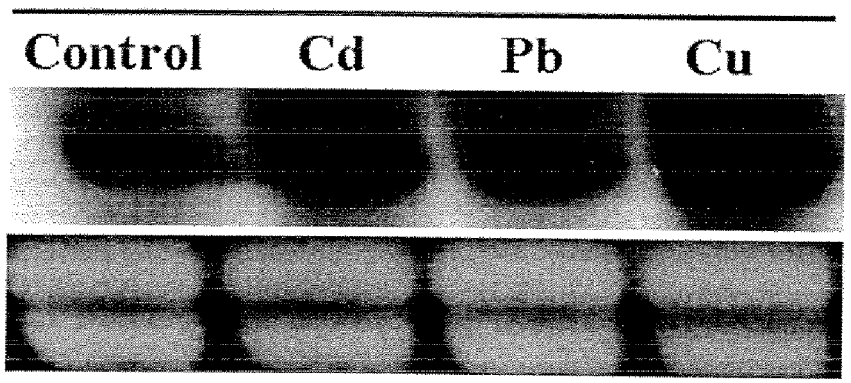
FIGS. 9A to 9C show that lead or copper-treatment of Arabidopsis increases expression of AtPDR8 gene by northern blotting (A) and realtime-PCR (B).
Figure 9B:
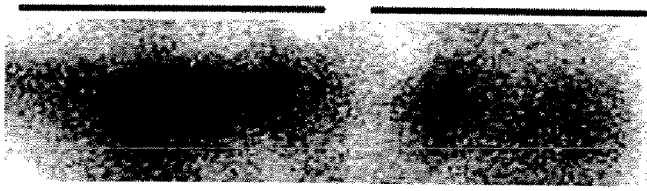
Figure 9C:
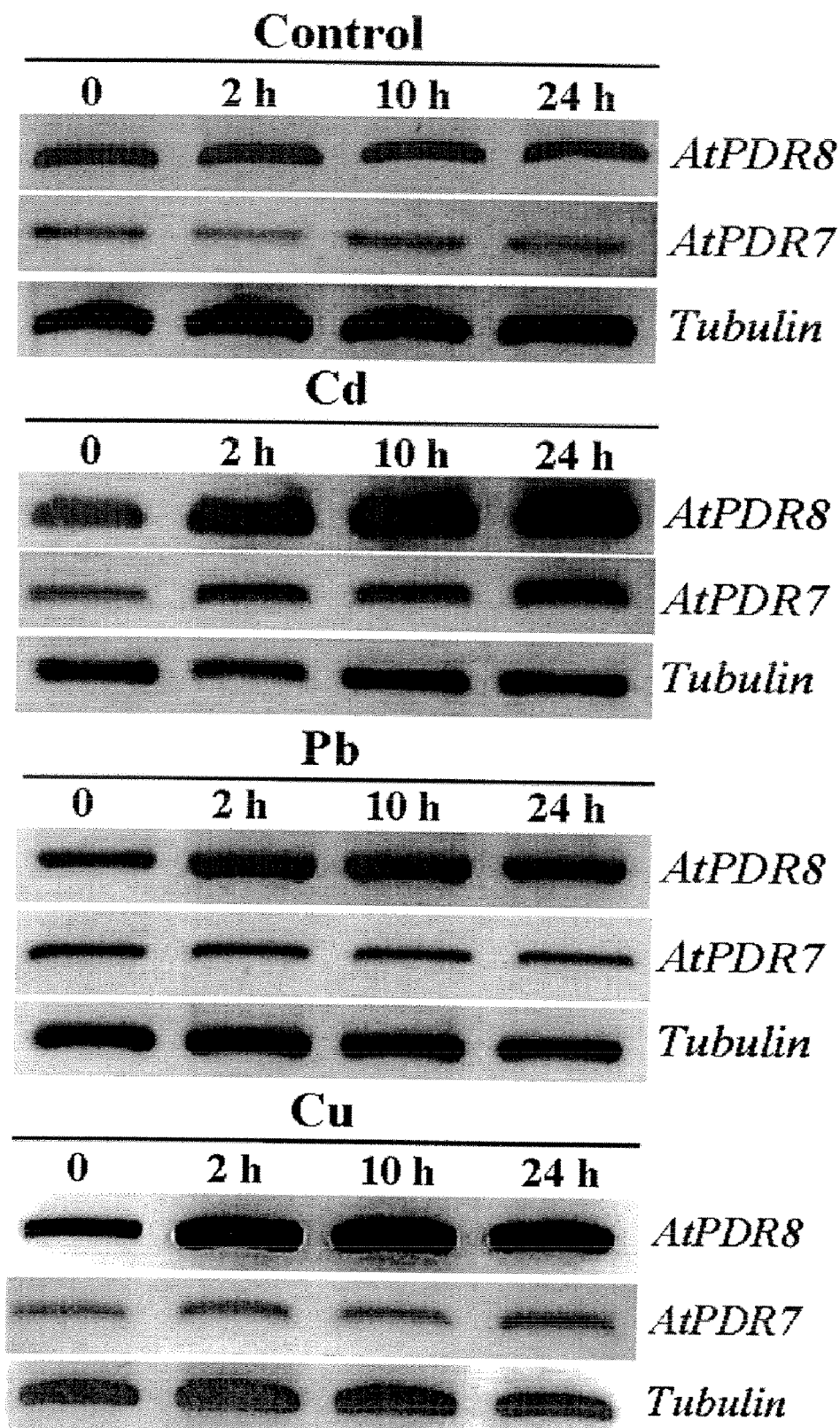
Figure 10A:
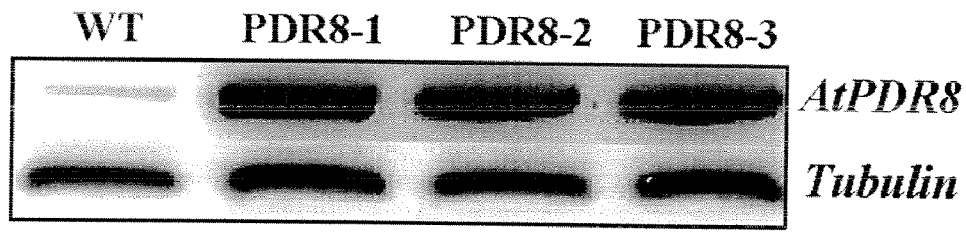
FIGS. 10A to 10D show that AtPDR8 over-expressing Arabidopsis transformant has improved cadmium or lead resistance. AtPDR8 gene expression in a AtPDR8 over-expressing Arabidopsis transformant is confirmed by RT-PCR (A); and shows growth (B), biomass (C), and root lengths (D) of the transformant when they are cultured in a medium including cadmium and lead.
Figure 10B:
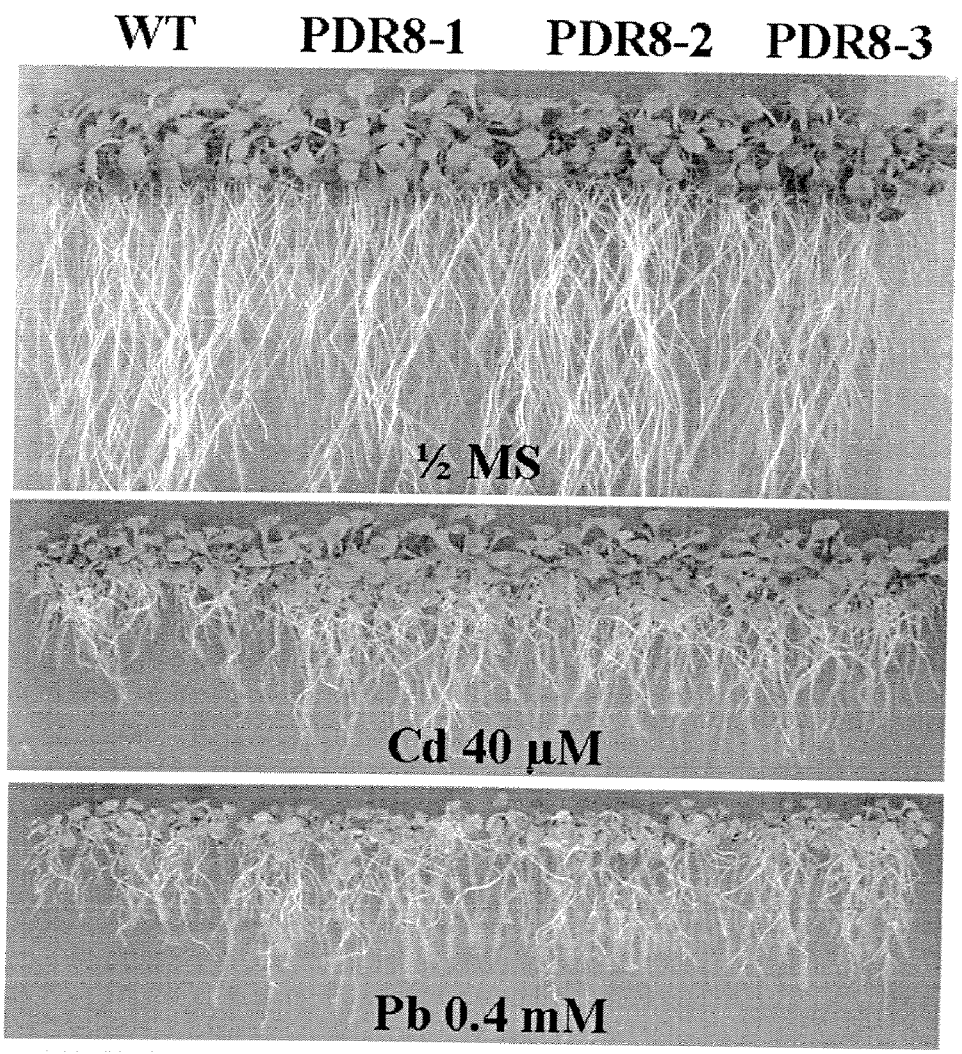
Figure 10C:
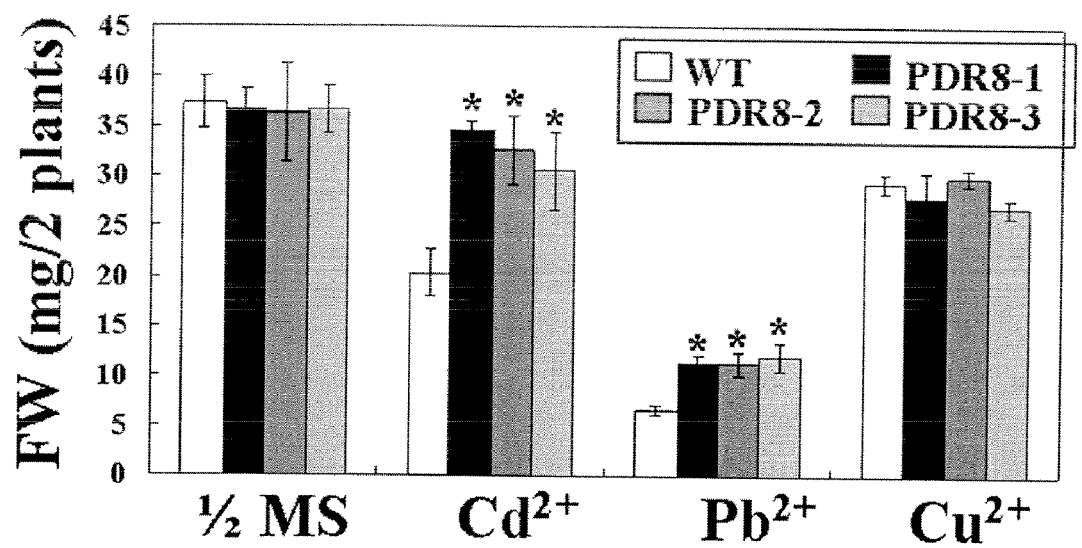
Figure 10D:
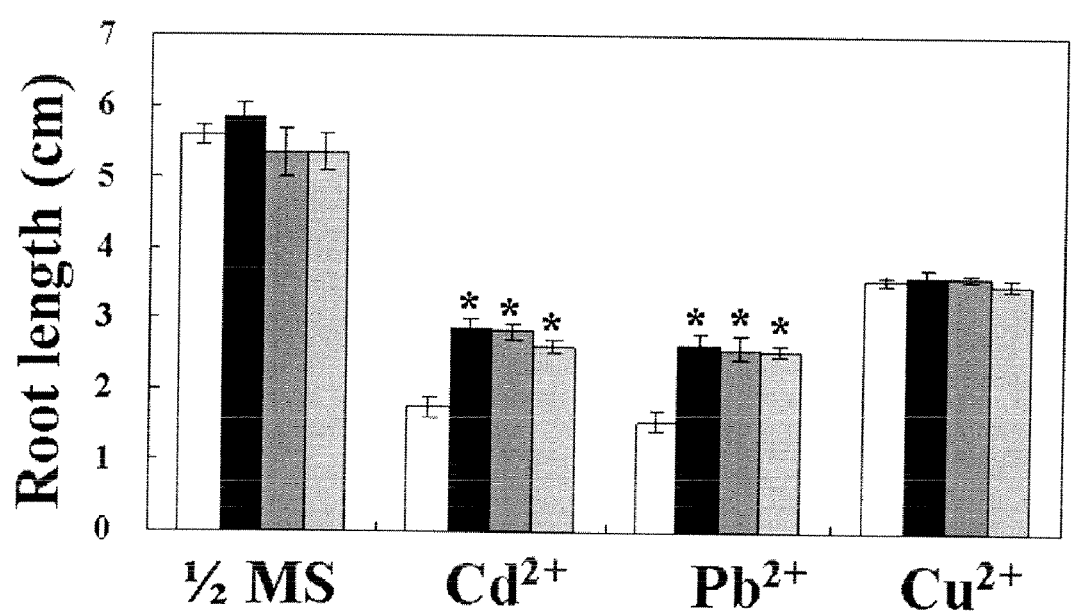

Next, expression of an AtPDR8 gene was examined by treating an Arabidopsis root with cadmium, lead, and copper and then, synthesized with cDNA. The resulting product was used as a template to perform PCR by using an AtPDR8-RTF (5'-CTCTTGATTGGTACAGTCTTCTG-3') primer (SEQ ID NO: 15) and an AtPDR8 RTR (5'-CCATAATGGTCCT CAATGTATTGC-3') primer (SEQ ID NO: 16). As a result, the AtPDR8 gene was highly expressed by cadmium, lead, and copper in the root (FIG. 9B). Then, expression of a tubulin gene was identified by performing PCR with (Tub-F (5'-GCTGACGTTTTCTGTATTCC-3') (SEQ ID NO: 17), Tub-R (5'-AGGCTCTGTATTGCTGTG AT-3') (SEQ ID NO: 18) primers as controls. As a result, the expression of tubulin was not changed by a heavy metal.

Figure 18A:
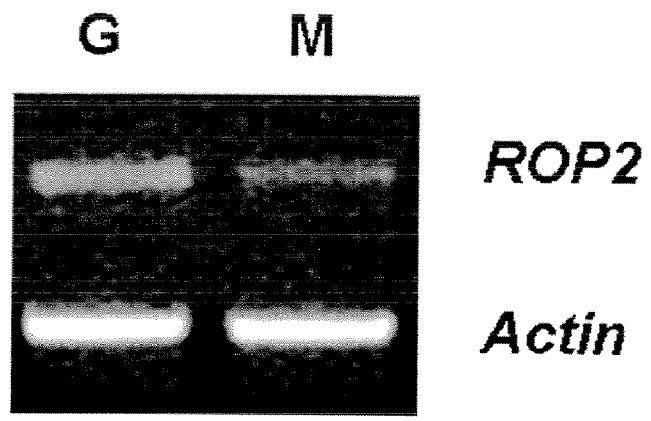
FIGS. 18A and 18B are photographs showing that Rop2 genes are actively expressed in guard cells of leaves of Arabidopsis which are analyzed by RT-PCR and Rop2 promoter:: GUS.
Figure 18B:
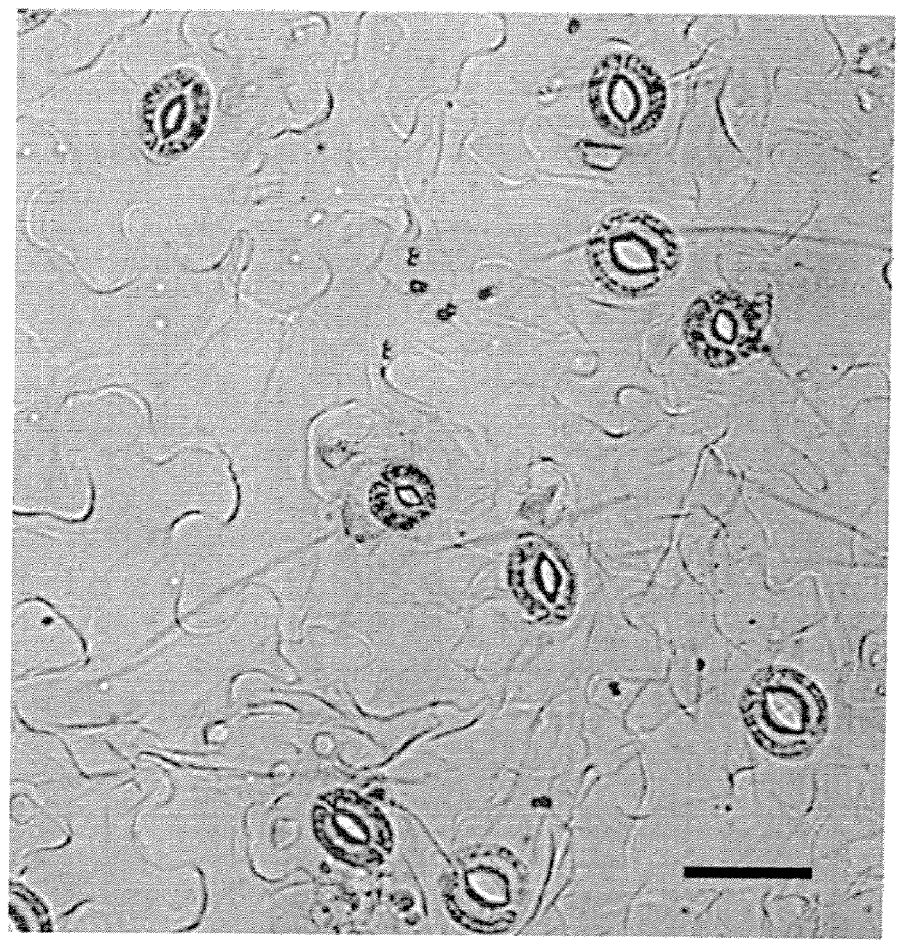

In addition, expression of a Rop2 gene in a guard cell was examined. Each cDNA was obtained from a guard cell and a somatic cell and used as a template. Then, PCR was performed to the cDNA by using a Rop2-forward primer (5'-CCGATCTTGGGCGAGATGGCGTCAAGG.-3') (SEQ ID NO: 19) and a Rop2-reverse primer (5'-CTTATCACA AGAACGCGCAACGGTTCTTATTC-3) (SEQ ID NO: 20). As a result, the Rop2 gene turned out to be highly expressed in the guard cell (FIGS. 18A and 18B). Expression of an actin2 gene as a control did not show any big difference in a guard cell and a somatic cell (Actin2-forward, 5'-GGC-CGATGGTGAGGATATTCAGCCACTTG-3', (SEQ ID NO: 21) Actin2-reverse, 5'-TCGATGGACCTGACTCATCG TACTCACTC-3') (SEQ ID NO: 22).

EXAMPLE 13

Northern Blotting 30 ug of RNA was subjected to electrophoresis in a formaldehyde gel, transferred to a nylon membrane, and then, bound by using a PCR product specific to a code sequence marked as .sup.32P-dCTP. The membrane was washed and exposed to a film to examine the expression degree of a gene. In order to gather base fragments specific to an AtPDR8 gene, the gene was amplified into PCR by using a PDR8NF primer (5'-AGCCTTGCTTTGTTTCACAG-3') (SEQ ID NO: 23) and a PDR8NR primer (5'-CCCTACTCATTCTC-CCCATTG-3') (SEQ ID NO: 24) and then, labeled as .sup32P, Then, expression of the AtPDR8 gene was identified in a northern blotting method. As a result, the expression of the AtPDR8 gene turned out to increase in a shoot region and a root due to cadmium, lead, and copper (FIG. 9A).

EXAMPLE 14

Western Blotting

Transformed yeast and an Arabidopsis were mixed with an extraction buffer (50 mM Hepes-KOH pH 7.4, 5 mM $MgCl_2$, 1 mM EDTA, 10 mM DTT, 0.7 ug/mL of pepstain A, 5 ug/mL of aprotinin, 20 ug/mL of leupeptin, 0.5 mM Phenylmethylsulfonyl fluoride) and thereafter, centrifuged at 12000 rpm for 5 minutes to separate a protein. The acquired supernatant was centrifuged again at 100,000 g for one hour, separating a membrane part of a cell from a liquid part thereof. About 10 to 50 ug of a protein was separated with a SDS-PAGE and then, transferred to nitrocellulose. The nitrocellulose was dipped in a 1×TBST (0.1% Tween 20 in 1×TBS) solution including 7.5% fat-free milk for one hour. The protein was repeatedly twice washed with a 1×TBST solution for 5 minutes and then, reacted with an antibody specific to each protein for 3 hours at a room temperature. Then, the resulting product was repeatedly three times washed with 1×TBST solution for 15 minutes, then, reacted with sheep anti-mouse IgG conjugated horshradish peroxidase for one hour, and three times washed with a 1×TBST solution for 10 minutes. An ECL (Amersham pharmacia Biotech) solution was used to detect expression signal of a protein with an x-ray film.

Figure 2B:
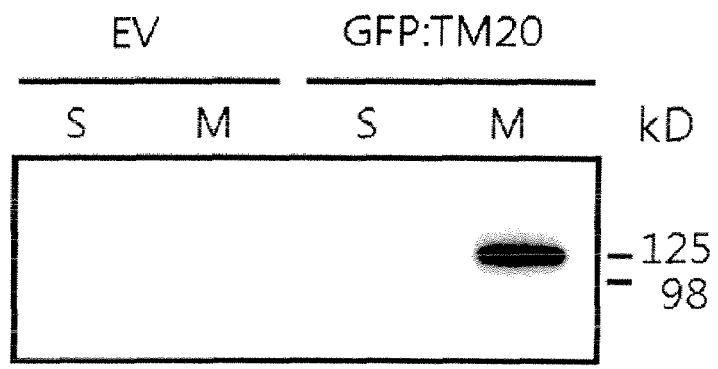
Figure 3A:
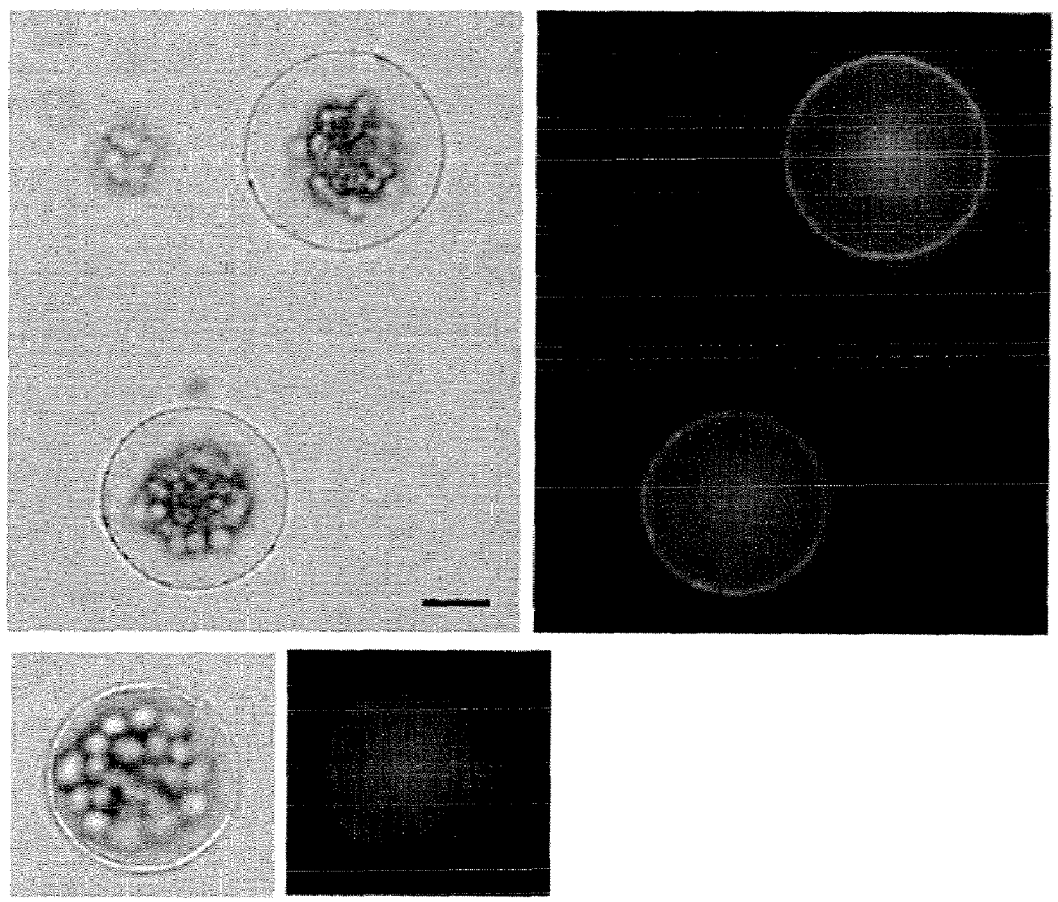
FIGS. 3A and 3B are photographs showing that GFP-AtPDR8 fusion protein expressed in a plant protoplast is positioned in a cell membrane, which is showed by green fluorescence (A); and a fusion protein position confirmed by western blotting using a GFP antibody (B).
Figure 3B:
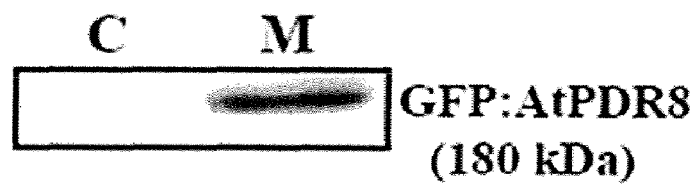

GFP-TaTM20 and GFP-AtPDR8 proteins were introduced into a protoplast, and then, the proteins were separated. Then, a western blotting method was performed regarding the proteins by using a GFP antibody. As a result, the proteins were identified to be located not in cytoplasm (cytosol, S, or C) but around a membrane (M) as shown in FIGS. 2B and 3B.

EXAMPLE 15

Construction of a RNAi Transgenic Plant

An AtPDR8 expression suppressing RNAi (RNA interference) plant was constructed by performing PCR with a P8RI-XK primer (5'-CCGCTCGAGCGGGATGCCT-TGCTTTGTTTCACAG-3') (SEQ ID NO: 25) and a P8RI-BX primer (5'-GGGGTACCGCCCCTACTCATTCTCCCCATTG-3') (SEQ ID NO: 26), inserting into a pHannibal vector by using XhoI-KpnI and BamHI-XbaI restriction enzymes, and then cloning in a pART27 binary vector using an Not I restriction enzyme.

The pART27-PDR8i vector was inserted into Arabidopsis by using agrobacterium, preparing an AtPDR8 RNAi transgenic plant.

EXAMPLE 16

Figure 4A:
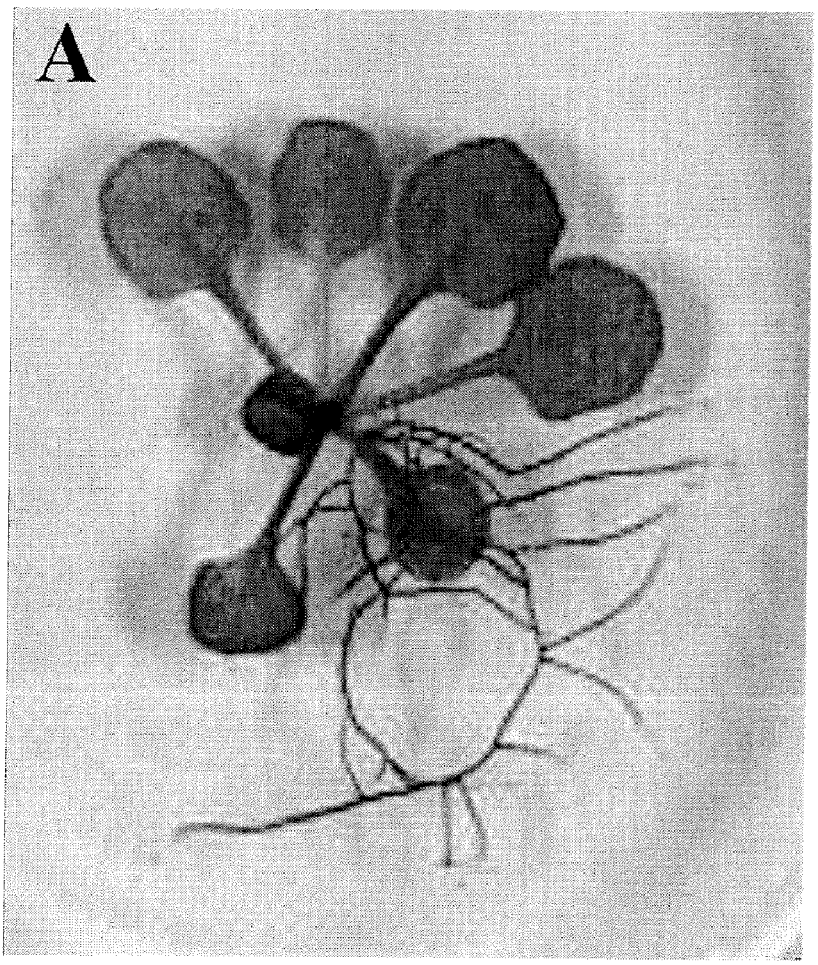
FIGS. 4A to 4G show an analysis result of expression position of a AtPDR8 gene in an Arabidopsis plant using a GUS marker gene. A fused gene of AtPDR8 gene promoter and GUS is expressed in both root and trunk and particularly is actively expressed in an epidermal cell.
Figure 4B:
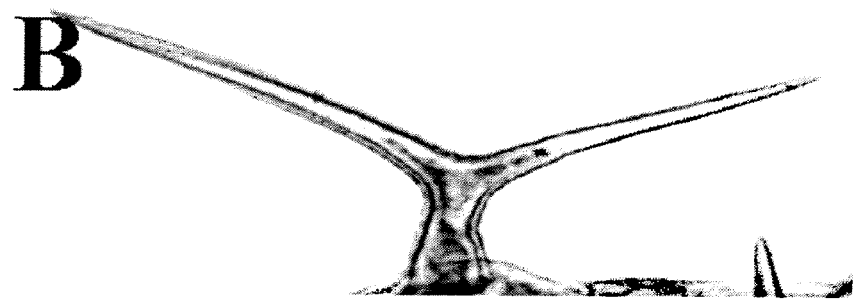
Figure 4C:
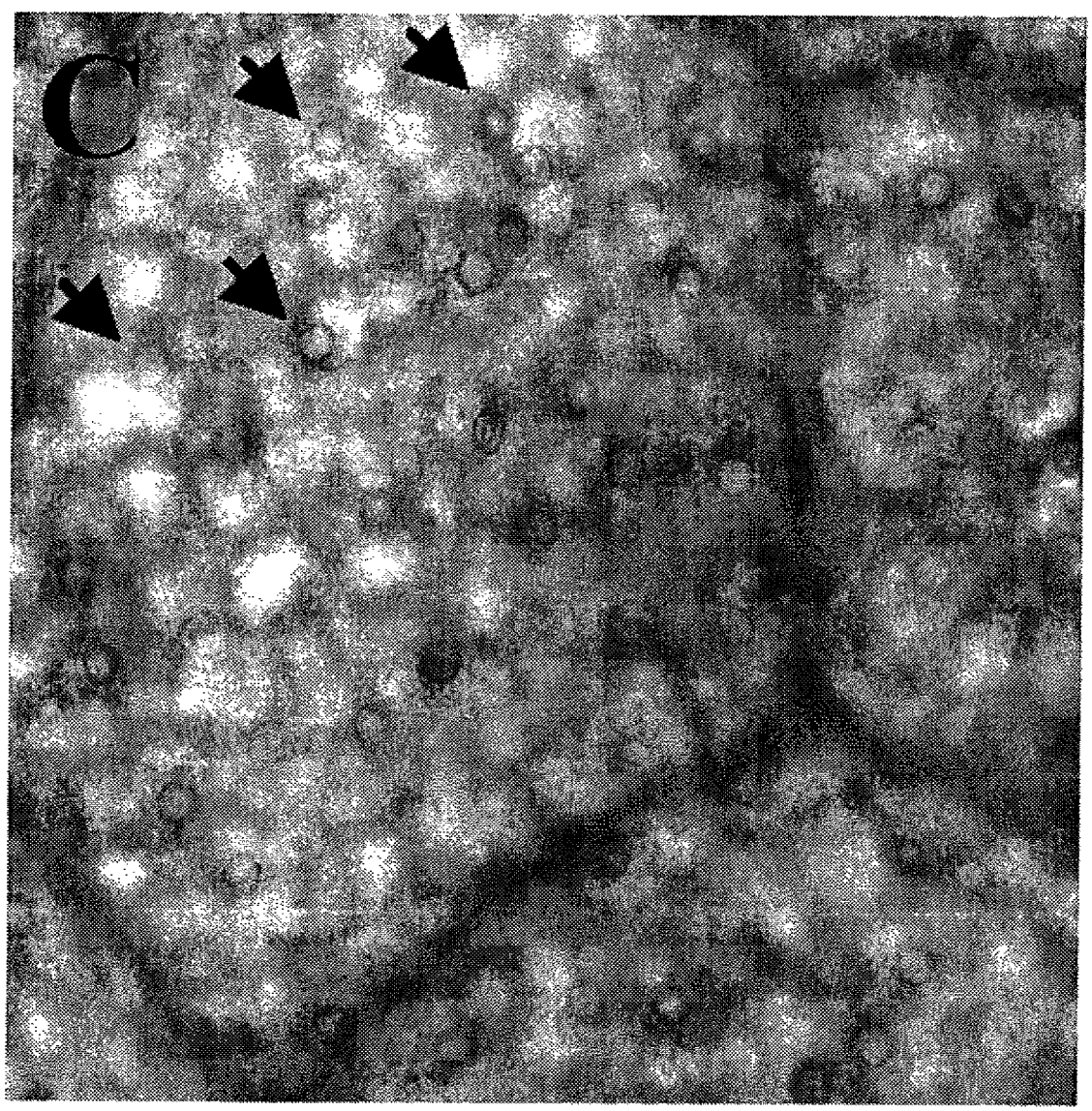
Figure 4D:
Figure 4E:
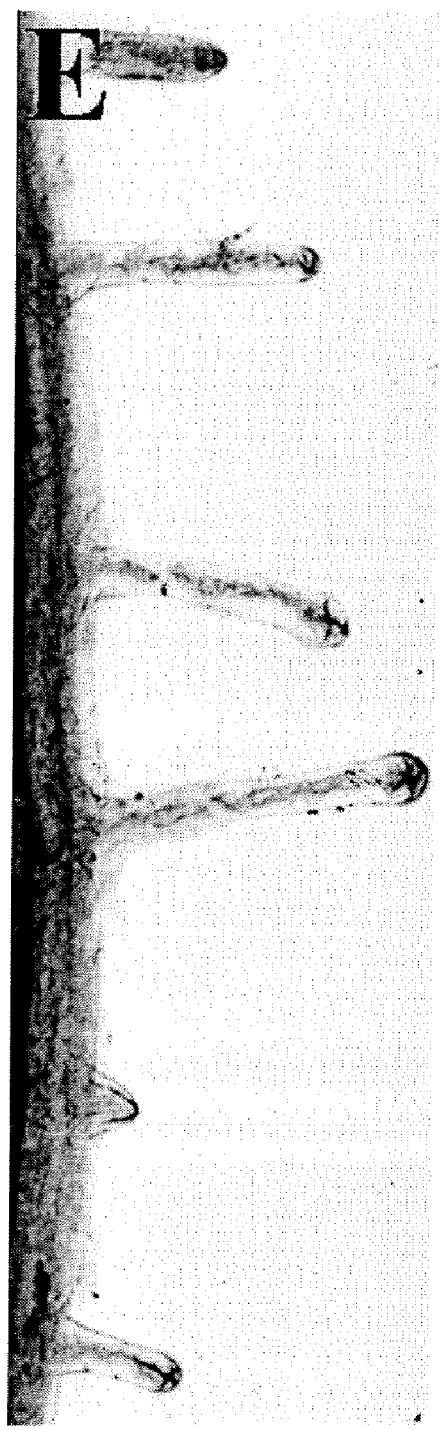
Figure 4F:
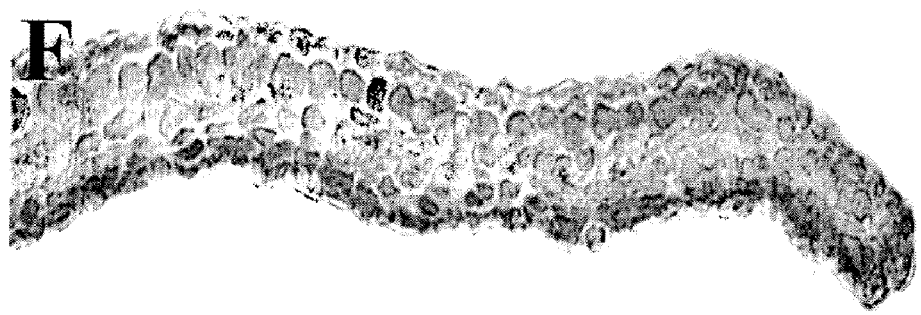
Figure 4G:
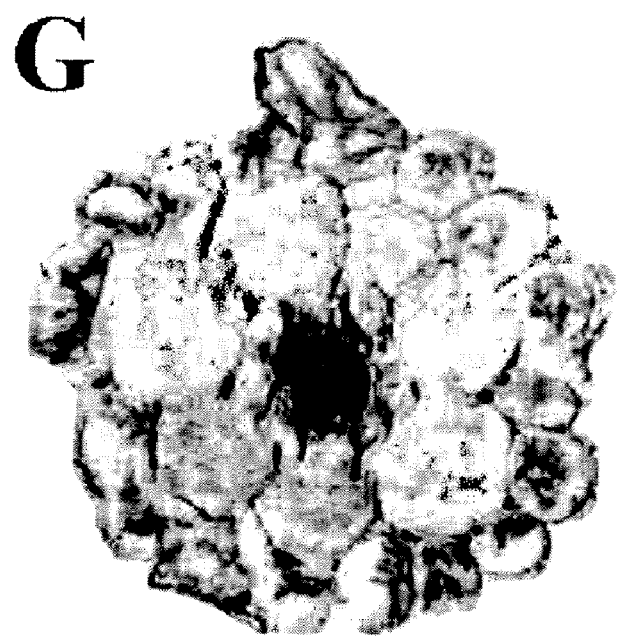

Determination of a Gene Expression Tissue by Using a Promoter-GUS Fused Protein A plant incubated in a MS medium for 2 weeks was incubated in 100 mM a phosphate buffer including 0.5 mM $K_4Fe(CN)_6$, 0.5 mM $K_3Fe(CN)_6$, 10 mM EDTA, 0.1% Triton X-100, and 500 mg/ml of X-Gluc for 24 hours, and 100% ethanol was added thereto to remove chlorophyll. Then, the chlorophyll was examined with an optic microscope. As a result, AtPDR8 promoter-GUS was expressed in both leaves and roots (FIGS. 4A to 4D), while Rop2 promoter-GUS was expressed around guard cells of the plant (FIGS. 18A and 18B). In addition, the expression in leaves and roots was more closely examined by dying their tissues. The tissues were severed with a microtome and thereafter, examined with a microscope. As a result, the AtPDR8 promoter-GUS gene was identified to be more strongly expressed in an epidermal cell (FIGS. 4E to G).

EXAMPLE 17

Figure 19A:
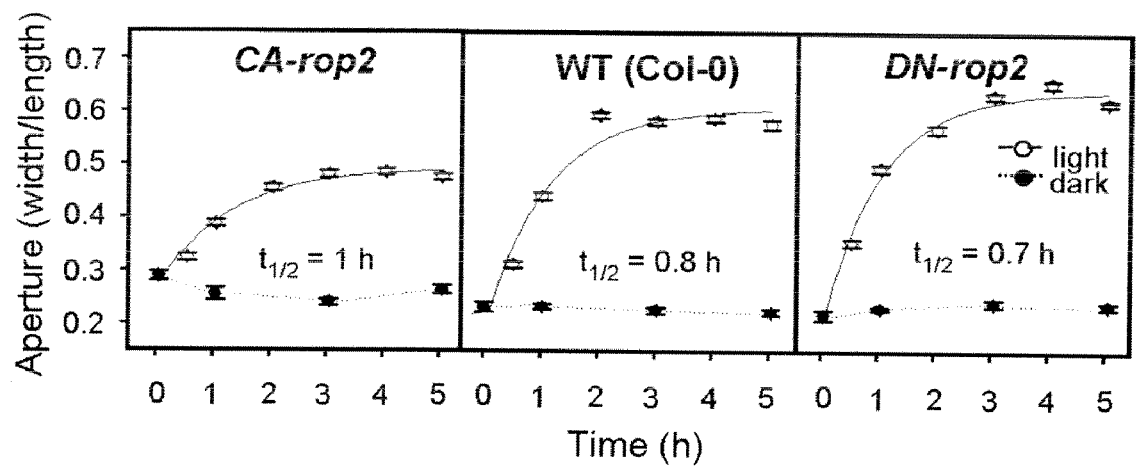
FIGS. 19A and 19B show pore-opening movement by light between Arabidopsis plants transformed with a mutant Rop2 gene and Arabidopsis plants where a Rop2 gene is not expressed. A plant expressing an active Rop2 (CA-Rop2) slowly opens pores a little compared to a wild type (wt), a plant expressing an inactive Rop2 (DN-Rop2) quickly opens pores more (A), and a plant that is not expressing Rop2 more quickly opens pores much more (B).
Figure 19B:
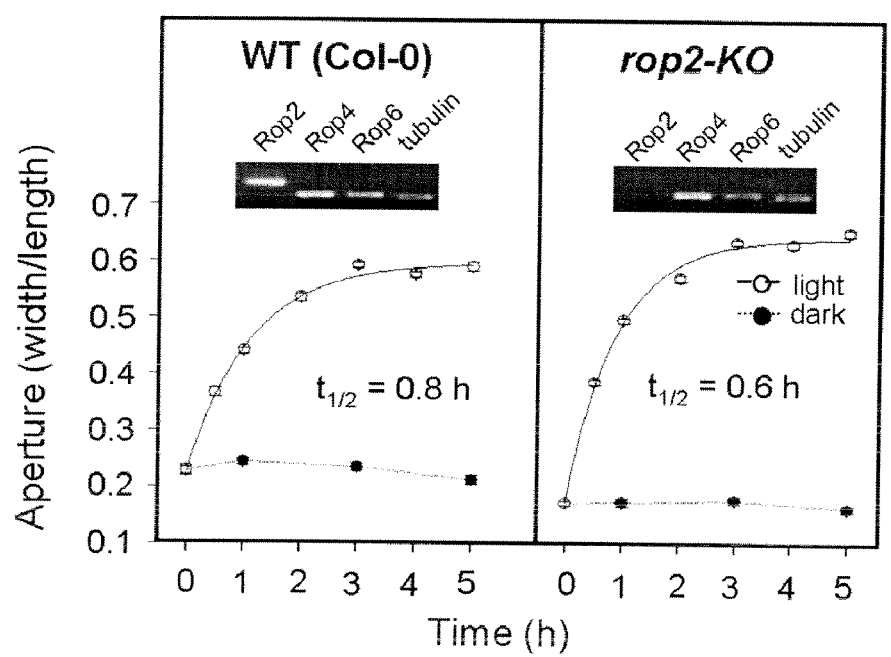

Measurement of Pore Movements as an Indicator of Transpiration, Through which Water and Other Materials are Transferred from a Root to a Shoot Region Epidermals of a plant leaf were peeled off and laid on a slide glass and then, examined with a microscope to measure the opening degree of a pore. In addition, the time for taking to reach half of the maximum opening was measured (t½). A plant expressed with an inactivated Rop2 gene (DN-Rop2) had more open pores than a wild-type one, and the pore opened faster (small t½ value) than the wild one. On the other hand, a plant expressed with an activated Rop2 gene (CA-Rop2) had a less open pore and the pore opened slowly (large t½ value) (FIG. 19A). In addition, when a plant had no gene expression, it had a more open Rop2-KO) pore than a wild-type one, and also, the pore opened faster (FIG. 19B). Therefore, when the amount or activity of a protein encoding this gene or other similar genes was deteriorated, the pore can be more open and open faster, increasing transpiration of a plant. In general, contamination materials come up to a shoot region of a plant during the transpiration. Accordingly, a plant pumping up a heavy metal to a shoot region and accumulating it therein can be developed. In other words, when a transgenic plant, which is developed to more open a pore and thereby, to do actively transpiration, was planted in a contaminated land, it can promote various contamination materials to move from a root to a shoot region, contributing to purifying the environment.

EXAMPLE 18

Figure 20:
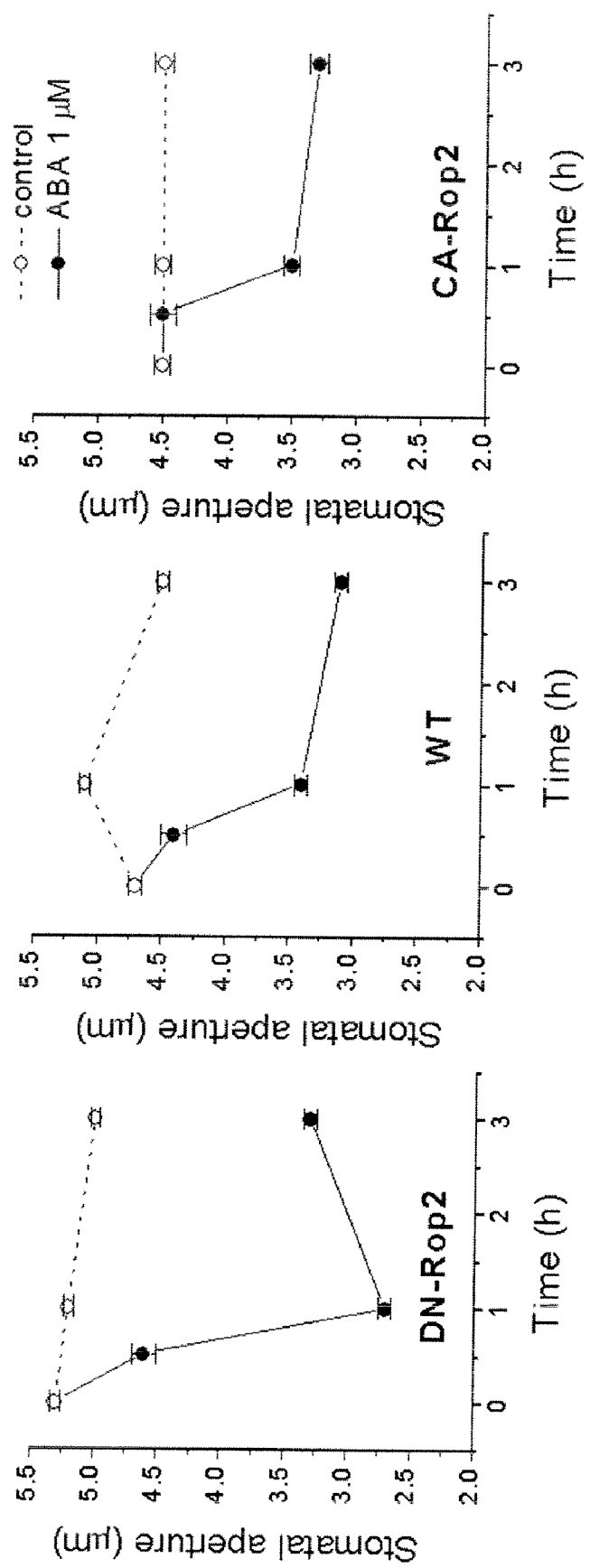
FIG. 20 shows pore closing movement by ABA of Arabidopsis plants transformed with a mutant Rop2 gene. A plant expressing an active Rop2 (CA-Rop2) slowly closesns pores a little compared to a wild type (wt), and a plant expressing an inactive Rop2 (DN-Rop2) quickly closes pores more.

Measurement of Pore-closing Movements as an Indicator of Drought Resistance by Using ABA A plant leaf was treated with ABA. Its epidermal was peeled off and laid on a slide glass to examine the closing degree of a pore with a microscope. A plant expressed with an inactivated Rop2 gene (DN-Rop2) had more closed pore than a wild-type one. On the other hand, a plant expressed with activated Rop2 gene (CA-Rop2) had more slowly and less closed pore than the wild-type one (FIG. 20). Therefore, when the amount or activity of a protein encoding this gene or other similar genes was deteriorated, a plant can be developed to have a pore close faster and more than a wild-type one and thereby, to have resistances against drought As aforementioned, the present invention provides a transformant including a gene with resistance against a heavy metal so that the transformant can grow in a polluted environment and thereby, be used for recovering the environment and thereby, establishing a pro-environmental park. In addition, it can prevent secondary contamination according to soil loss in the contaminated land and also, be used to develop a safe plant less absorbing a heavy metal than a wild-type one. In addition, a transgenic plant inserted with a gene having resistance against the heavy metal and base or drought does not only has excellent heavy metal resistance but also pump up various contamination materials from root to shoot region, contributing to developing a new plant for purifying the environment. According to the present invention, an AtPDR8 gene can increase resistance against base and drought as well as a heavy metal, so that a plant including it can be used for purifying and recovering contaminated areas. In addition, TaTM20 and AtPDR8 genes can decrease the amount of a heavy metal in a plant and thereby, be used to develop a plant less including heavy metals and thereby, more safe. Furthermore, when AtPDR8 or other similar genes are over-expressed or Rop2 is suppressed, a plant including them can have improved resistance against base or drought. Accordingly, a newly-developed species can contribute to farming and environment in a reclaimed land or an arid based on this technology.

While this invention has been described in connection with what is presently considered to be practical exemplary embodiments, it is to be understood that the invention is not limited to the disclosed embodiments, but on the contrary, is intended to cover various modifications and equivalent arrangements included within the spirit and scope of the appended claims.

What is claimed is:

1. A recombinant vector comprising a nucleic acid operably linked to transcription and translation controlling elements to be expressed in a plant, wherein the nucleic acid has heavy metal resistance and accumulation properties and comprises a sequence encoding a transmembrane protein having five times repeated similar four transmembrane domains, the sequence selected from the group consisting of the sequence of SEQ ID NO: 1 and a sequence having 95% to 99% sequence homology to SEQ ID NO: 1; wherein the vector further comprises a salt or drought resistance gene comprising a sequence encoding an ABC transporter protein selected from the group consisting of the sequence of SEQ ID NO: 3 and a sequence having 95% to 99% sequence homology to SEQ ID NO: 3 and comprising twice repeated six transmembrane domains and ATP-binding domains.

2. The recombinant vector of claim 1, wherein the sequence encoding an ABC transporter protein that comprises twice repeated six transmembrane domains and ATP-binding domains is SEQ ID NO: 3.

3. The recombinant vector of claim 1, wherein the sequence encoding an ABC transporter protein that comprises twice repeated six transmembrane domains and ATP-binding domains is a sequence having 95% to 99% sequence homology to SEQ ID NO: 3.

4. A transformed host cell obtained by transformation with a recombinant vector comprising a nucleic acid operably linked to transcription and translation controlling elements to be expressed in the host cell, wherein the nucleic acid has heavy metal resistance and accumulation properties and comprises a sequence encoding a transmembrane protein having five times repeated similar four transmembrane domains, the sequence selected from the group consisting of the sequence of SEQ ID NO: 1 and a sequence having 95% to 99% sequence homology to SEQ ID NO: 1, wherein the vector further comprises a salt or drought resistance gene comprising a sequence encoding an ABC transporter protein selected from the group consisting of the sequence of SEQ ID NO: 3 and a sequence having 95% to 99% sequence homology to SEQ ID NO: 3 and comprising twice repeated six transmembrane domains and ATP-binding domains.

5. The transformed host cell of claim 4, wherein the sequence encoding an ABC transporter protein that comprises twice repeated six transmembrane domains and ATP-binding domains is SEQ ID NO: 3.

6. The transformed host cell of claim 4, wherein the sequence encoding an ABC transporter protein that comprises twice repeated six transmembrane domains and ATP-binding domains is a sequence having 95% to 99% sequence homology to SEQ ID NO: 3.

7. The transformed host cell of claim 4, wherein the sequence encoding a transmembrane protein having five times repeated similar four transmembrane domains is a sequence having 95% to 99% sequence homology to SEQ ID NO: 1.

8. The transformed host cell of claim 4, which is a plant cell.

9. The transformed host cell of claim 8, wherein the plant cell is from a plant selected from the group consisting of an onion, a carrot, a cucumber, an olive tree, a sweet potato, a potato, a cabbage, a radish, lettuce, broccoli, tobacco, *Petunia hybrida*, a sunflower, *Brassica juncea*, turf, *Arabidopsis thaliana*, *Brassica campestris*, *Betula platyphylla*, a poplar, a hybrid poplar, and *Betula schmidtii*.

10. A transformed part of a transgenic plant wherein the transgenic plant is obtained by transformation with a recombination vector comprising a gene linked to transcription and translation controlling element to be expressed in the plant, wherein the gene has heavy metal resistance and accumulation properties and comprises a sequence encoding a transmembrane protein having five times repeated similar four transmembrane domains, the sequence selected from the group consisting of the sequence of SEQ ID NO: 1 and a sequence having 95%-99% sequence homology to SEQ ID NO: 1, wherein the vector further comprises a salt or drought resistance gene comprising a sequence encoding an ABC transporter protein selected from the group consisting of the sequence of SEQ ID NO: 3 and a sequence having 95%-99% sequence homology to SEQ ID NO: 3 and comprising twice repeated six transmembrane domains and ATP-binding domains.

11. A transformed plant cell obtained by transformation with a recombination vector comprising a nucleic acid operably linked to transcription and translation controlling elements to be expressed in a plant, wherein the nucleic acid has heavy metal resistance and accumulation properties and comprises a sequence encoding a transmembrane protein having five times repeated similar four transmembrane domains, the sequence selected from the group consisting of the sequence of SEQ ID NO: 1 and a sequence having 95% to 99% sequence homology to SEQ ID NO: 1, wherein the vector further comprises a salt or drought resistance gene comprising a sequence encoding an ABC transporter protein selected from the group consisting of the sequence of SEQ ID NO: 3 and a sequence having 95% to 99% sequence homology to SEQ ID NO: 3 and comprising twice repeated six transmembrane domains and ATP-binding domains.

12. The transformed plant cell of claim 11, wherein the plant cell is from a plant selected from the group consisting of an onion, a carrot, a cucumber, an olive tree, a sweet potato, a potato, a cabbage, a radish, lettuce, broccoli, tobacco, *Petunia hybrida*, a sunflower, *Brassica juncea*, turf, *Arabidopsis thaliana*, *Brassica campestris*, *Betula platyphylla*, a poplar, a hybrid poplar, and *Betula schmidtii*.

13. A method of producing a plant having heavy metal resistance and accumulation activities, comprising (a) constructing an expression cassette that includes a nucleic acid operably linked to a transcription and translation controlling element to be expressed in the plant, wherein the nucleic acid has heavy metal resistance and accumulation properties and comprises a sequence encoding a transmembrane protein having five times repeated similar four transmembrane domains, the sequence selected from the group consisting of the sequence of SEQ ID NO: 1 and a sequence having 95% to 99% sequence homology to SEQ ID NO: 1;

(b) preparing a recombinant vector including the expression cassette;

(c) introducing the recombinant vector into a plant cell or a plant tissue, wherein the expression cassette further comprises a salt or drought resistance gene comprising a sequence encoding an ABC transporter protein selected from the group consisting of the sequence of SEQ ID NO: 3 and a sequence having 95% to 99% sequence homology to SEQ ID NO: 3 and comprising twice repeated six transmembrane domains and ATP-binding domains;

and (d) regenerating a plant having heavy metal resistance and accumulation activities from the plant cell or plant tissue.

14. A recombinant vector comprising a nucleic acid operably linked to transcription and translation controlling elements to be expressed in a plant, wherein the nucleic acid has heavy metal resistance and accumulation properties and comprises SEQ ID NO: 1 encoding a transmembrane protein having five times repeated similar four transmembrane domains, wherein the vector further comprises a salt or drought resistance gene comprising the sequence of SEQ ID NO: 3 encoding an ABC transporter protein that comprises twice repeated six transmembrane domains and ATP-binding domains.

15. A transformed plant obtained by transformation with a recombination vector comprising a nucleic acid operably linked to transcription and translation controlling elements to be expressed in the plant, wherein the nucleic acid has heavy metal resistance and accumulation properties and comprises SEQ ID NO: 1 encoding a transmembrane protein having five times repeated similar four transmembrane domains, wherein the vector further comprises a salt or drought resistance gene comprising the sequence of SEQ ID NO: 3 encoding an ABC transporter protein that comprises twice repeated six transmembrane domains and ATP-binding domains.

* * * * *

SEQUENCE LISTING

<160> NUMBER OF SEQ ID NOS: 31

<210> SEQ ID NO 1
<211> LENGTH: 2998
<212> TYPE: DNA
<213> ORGANISM: Triticum aestivum

<400> SEQUENCE: 1

```
gtggaattcc aataattaga gtaagaacag gaagcgtacc acagccgttg agtgagagaa      60
tggagtgtgg tggcgtctcc gccgtgcagg tgcagccggc agtgcacatg ggtcagcccg     120
gccagccggc aaagccgccg gtgcagccat gggagtacag cctgcggaag tacctcctgc     180
tgctggccgc cctggtggtc accgtcacgt acgccgccgg cttcagcccg ccggggggcg     240
tctggcaggc cgcccacgac ggccagcccg ccggcgaccc catcatccgc ggaacccact     300
accgccgcta cctcgccttc ttctactgca acgccaccgc cttcgccgcg tcgctcgtgg     360
tcatcgtcct catcctcatc ctcgccgtcc gccacgacaa gaaggggaag gacagccgct     420
gggtcgtcgt gcccctgcgg ctggtcatgg tgctggacct gctcagcctc atgggcgcgt     480
acggcgccgg cacctgccag gacaagatct ccatcgtcta ctccgcggtg ctggtggccg     540
ccgtcttcct ctacgtcgcc gttctcaaga tgatggactg gtggtgccca gacaacaaaa     600
ccggccccgg ttgcgacggc acaatgtcat ccgcccccaa cagcaactcc aactccggcg     660
acgtgatgtc cactcctgat cccgactccg acgccgtcac gattccatcc ccctccgcg     720 actctgaccc caatgtcaaa gaagaagagg accgcaaacg cgaggccctg aagaagctga     780
aagccaacga acggctccgc aaagtcctga tgctcctggc gacgttcgcg gtgagcatca     840
cgtacgtcgc cgggctgagc atgccgggtg gcttctggga cagcaccggg accagctacc     900
gcccgggcga tgcaatcctc aaggaccgcc accgccgcg cctgacggcg ttcctgctct     960
gcaacaccac atcgttcgtg gcgtccctgc tcatcatcat gctgcttatc attgacggca    1020
agaagctccg cgacaagaag gctcggtcgc tcgtgctcta cgggttcatc gtcgtcgcgc    1080
tggtcagcct cgtcggcgct tacaccgctg gcagctgcag ggagacaaaa accaccatct    1140
acgtggtctc cctgaccggc ggcattctgg caatggcata catcctgctc tatgctttct    1200
```

-continued

```
atactttaaa gtcttctcgt tccagtccaa cgcaaccaac ggatgcactt cagcagacta      1260
ctgataatgt cagtgctaga aagggtctgg acaaggctcg ctctcttgtt ctactgcttg      1320
ccactcttgc cgccaccatc acctacacag cgggtttgga cccgccaggt ggcctttggc      1380
aggacaaggg cgatgggtac atcgccggcg acccgattct aatcacaacc acattagga      1440 ggtacagggc cttctactac tgcaactcgg ttgcgttcgt ggcgtccttg ctggtcatcg      1500
tcctggtcca gacggagagg ctgatcaagc caccgtgct ggaggcagcc atgatactcg       1560
acctgtttgg cctcatcggt gcgtatgccg ctgggagctg tcggaacgtg aattcctccg      1620
tttacgtcat ggctttggca ggcgccgccc tgatctatgt ggtgatccat attgtctttt      1680
tcacgctgga gctggaccag aaggacaaga agacgacga tcaagaagat gagttgctgg       1740
agaagaggcg caaaaggttg ctcctcttcg cgatcttggc cgcaaccatc acctatcaag      1800
ccggcctcac ccctcctggc gggttccttc tccaggatga cacgctcggg caccatgccg      1860
gtgacccgat cctcttgcac aactaccag tccgctacca tgccttcttc tactgcaact       1920
cagtgagctt catgctgtcc atcgccctca tcatcctcct ggtgaacccc aatctgtaca      1980
ggccagccat acaaagcaat gcactatccg tttgcacggc cgtgggcttg ttttgtttga      2040
tgggggccta cgccgccgga agcacgcaac accgcaagac atccatctac atcttcgtgt      2100
tggtggctgt ggtcctgctc gttgcagccg gactgctgct ggtattttg ctgaagagaa        2160 agctcagcaa tgccgtagtc tcaccaccca gagaacagaa cgaagaagaa aggaaggagg      2220
tagaagaaaa gaatgaggat gaagaagaag cgaagaagca tgcgaggcgc aagtatctga     2280
tgctgctagg aatcttggtg gcgagcgtag cctaccaggc cggcctggaa ccgcccggcg     2340
gggcgtggca gaacaacgac aacgggtacg aggcgggcaa cccggtgatg aacgacaaca     2400
ggaggccccg gtacctcacc ttcttctaca gcaactccgt ttcctttgtg gcttccatcg     2460
ttgtcatcat catgttgcta ccgcaatggc tgccaaagaa gaaagaagga gaatgggaga     2520
aatggtcgct gagggtgatg aactggatga tccgactgga tctgtttgct ctcctagtgg     2580
cctatgcagc cggctccaac aggggttga agacatccct ttatgtcgtc gcactcatct      2640
ttgctgtgct gggctacttt gcaatccata cggtgctggc atgtaccgtt tgtcgccatg     2700
agaggcgcca aagcagctct gtagtgtagt tctactatgt agtgtagctc tactatggcc     2760
ctcgtctgag ctctgtactg tagatctcta atcagcacgc cctactctag ctagctctgt     2820
ccctacgatc gaaaagcttc tctgttttta gattcctagt ctagttgatg taatcggata     2880
atcggattaa cctgaatccc aattggagca tgctaacatt gtttgtcgac tcactgggcc     2940
ggtctttctg tatcttaacc caatggatat gtatggtagg tgacatttc ctgaaaaa       2998
```

<210> SEQ ID NO 2
<211> LENGTH: 889
<212> TYPE: PRT
<213> ORGANISM: Triticum aestivum

<400> SEQUENCE: 2

Met Glu Cys Gly Gly Val Ser Ala Val Gln Val Gln Pro Ala Val His
1               5                   10                  15

Met Gly Gln Pro Gly Gln Pro Ala Lys Pro Val Gln Pro Trp Glu
            20                  25                  30

Tyr Ser Leu Arg Lys Tyr Leu Leu Leu Ala Ala Leu Val Val Thr
        35                  40                  45

Val Thr Tyr Ala Ala Gly Phe Ser Pro Pro Gly Gly Val Trp Gln Ala
    50                  55                  60

-continued

```
Ala His Asp Gly Gln Pro Ala Gly Asp Pro Ile Ile Arg Gly Thr His
 65                  70                  75                  80

Tyr Arg Arg Tyr Leu Ala Phe Phe Tyr Cys Asn Ala Thr Ala Phe Ala
                 85                  90                  95

Ala Ser Leu Val Val Ile Val Leu Ile Leu Ile Leu Ala Val Arg His
            100                 105                 110

Asp Lys Lys Gly Lys Asp Ser Arg Trp Val Val Pro Leu Arg Leu
            115                 120                 125

Val Met Val Leu Asp Leu Leu Ser Leu Met Gly Ala Tyr Gly Ala Gly
            130                 135                 140

Thr Cys Gln Asp Lys Ile Ser Ile Val Tyr Ser Ala Val Leu Val Ala
145                 150                 155                 160

Ala Val Phe Leu Tyr Val Ala Val Leu Lys Met Met Asp Trp Trp Cys
                165                 170                 175

Pro Asp Asn Lys Thr Gly Pro Gly Cys Asp Gly Thr Met Ser Ser Ala
            180                 185                 190

Pro Asn Ser Asn Ser Asn Ser Gly Asp Val Met Ser Thr Pro Asp Pro
            195                 200                 205

Asp Ser Asp Ala Val Thr Ile Pro Ser Pro Leu Arg Asp Ser Asp Pro
        210                 215                 220

Asn Val Lys Glu Glu Asp Arg Lys Arg Glu Ala Leu Lys Lys Leu
225                 230                 235                 240

Lys Ala Asn Glu Arg Leu Arg Lys Val Leu Met Leu Leu Ala Thr Phe
                245                 250                 255

Ala Val Ser Ile Thr Tyr Val Ala Gly Leu Ser Met Pro Gly Gly Phe
            260                 265                 270

Trp Asp Ser Thr Gly Thr Ser Tyr Arg Pro Gly Asp Ala Ile Leu Lys
            275                 280                 285

Asp Arg His Arg Pro Arg Leu Thr Ala Phe Leu Leu Cys Asn Thr Thr
            290                 295                 300

Ser Phe Val Ala Ser Leu Leu Ile Ile Met Leu Leu Ile Ile Asp Gly
305                 310                 315                 320

Lys Lys Leu Arg Asp Lys Lys Ala Arg Ser Leu Val Leu Tyr Gly Phe
                325                 330                 335

Ile Val Val Ala Leu Val Ser Leu Val Gly Ala Tyr Thr Ala Gly Ser
            340                 345                 350

Cys Arg Glu Thr Lys Thr Thr Ile Tyr Val Val Ser Leu Thr Gly Gly
            355                 360                 365

Ile Leu Ala Met Ala Tyr Ile Leu Leu Tyr Ala Phe Tyr Thr Leu Lys
            370                 375                 380

Ser Ser Arg Ser Ser Pro Thr Gln Pro Thr Asp Ala Leu Gln Gln Thr
385                 390                 395                 400

Thr Asp Asn Val Ser Ala Arg Lys Gly Leu Asp Lys Ala Arg Ser Leu
                405                 410                 415

Val Leu Leu Leu Ala Thr Leu Ala Ala Thr Ile Thr Tyr Thr Ala Gly
            420                 425                 430

Leu Asp Pro Pro Gly Gly Leu Trp Gln Asp Lys Gly Asp Gly Tyr Ile
            435                 440                 445

Ala Gly Asp Pro Ile Leu Ile Thr Thr Asn Ile Arg Arg Tyr Arg Ala
            450                 455                 460

Phe Tyr Tyr Cys Asn Ser Val Ala Phe Val Ala Ser Leu Leu Val Ile
465                 470                 475                 480
```

```
Val Leu Val Gln Thr Glu Arg Leu Ile Lys His His Val Leu Glu Ala
            485                 490                 495

Ala Met Ile Leu Asp Leu Phe Gly Leu Ile Gly Ala Tyr Ala Ala Gly
            500                 505                 510

Ser Cys Arg Asn Val Asn Ser Ser Val Tyr Val Met Ala Leu Ala Gly
            515                 520                 525

Ala Ala Leu Ile Tyr Val Val Ile His Ile Val Phe Phe Thr Leu Glu
            530                 535                 540

Leu Asp Gln Lys Asp Lys Lys Asp Asp Gln Glu Asp Glu Leu Leu
545                 550                 555                 560

Glu Lys Arg Arg Lys Arg Leu Leu Leu Phe Ala Ile Leu Ala Ala Thr
            565                 570                 575

Ile Thr Tyr Gln Ala Gly Leu Thr Pro Pro Gly Gly Phe Leu Leu Gln
            580                 585                 590

Asp Asp Thr Leu Gly His His Ala Gly Asp Pro Ile Leu Leu His Asn
            595                 600                 605

Tyr Pro Val Arg Tyr His Ala Phe Phe Tyr Cys Asn Ser Val Ser Phe
            610                 615                 620

Met Leu Ser Ile Ala Leu Ile Ile Leu Leu Val Asn Pro Asn Leu Tyr
625                 630                 635                 640

Arg Pro Ala Ile Gln Ser Asn Ala Leu Ser Val Cys Thr Ala Val Gly
            645                 650                 655

Leu Phe Cys Leu Met Gly Ala Tyr Ala Ala Gly Ser Thr Gln His Arg
            660                 665                 670

Lys Thr Ser Ile Tyr Ile Phe Val Leu Val Ala Val Leu Leu Val
            675                 680                 685

Ala Ala Gly Leu Leu Leu Val Phe Leu Leu Lys Arg Lys Leu Ser Asn
            690                 695                 700

Ala Val Val Ser Pro Pro Arg Glu Gln Asn Glu Glu Glu Arg Lys Glu
705                 710                 715                 720

Val Glu Glu Lys Asn Glu Asp Glu Glu Glu Ala Lys Lys His Ala Arg
            725                 730                 735

Arg Lys Tyr Leu Met Leu Leu Gly Ile Leu Val Ala Ser Val Ala Tyr
            740                 745                 750

Gln Ala Gly Leu Glu Pro Pro Gly Gly Ala Trp Gln Asn Asn Asp Asn
            755                 760                 765

Gly Tyr Glu Ala Gly Asn Pro Val Met Asn Asp Asn Arg Arg Pro Arg
            770                 775                 780

Tyr Leu Thr Phe Phe Tyr Ser Asn Ser Val Ser Phe Val Ala Ser Ile
785                 790                 795                 800

Val Val Ile Ile Met Leu Leu Pro Gln Trp Leu Pro Lys Lys Lys Glu
            805                 810                 815

Gly Glu Trp Glu Lys Trp Ser Leu Arg Val Met Asn Trp Met Ile Arg
            820                 825                 830

Leu Asp Leu Phe Ala Leu Leu Ala Tyr Ala Ala Gly Ser Asn Arg
            835                 840                 845

Gly Leu Lys Thr Ser Leu Tyr Val Val Ala Leu Ile Phe Ala Val Leu
            850                 855                 860

Gly Tyr Phe Ala Ile His Thr Val Leu Ala Cys Thr Val Cys Arg His
865                 870                 875                 880

Glu Arg Arg Gln Ser Ser Ser Val Val
            885
```

<210> SEQ ID NO 3
<211> LENGTH: 4410
<212> TYPE: DNA
<213> ORGANISM: Arabidopsis thaliana

<400> SEQUENCE: 3

| | | | | | |
|---|---|---|---|---|---|
| atggattaca | atccaaatct | tcctccttta | ggaggaggtg | gtgttagtat | gagaagaagc | 60 |
| ataagtcgaa | gtgtaagcag | agcaagtagg | aacattgaag | atatcttctc | atctggttca | 120 |
| agaagaacac | aatcagtcaa | cgacgatgaa | gaagctctta | aatgggctgc | cattgagaag | 180 |
| ctaccaactt | acagtcgtct | ccgaaccact | ctcatgaacg | ctgtagtcga | agacgatgtt | 240 |
| tacggtaacc | agctcatgag | caaggaggtt | gatgtaacca | agcttgatgg | tgaagatcgt | 300 |
| cagaagttta | ttgacatggt | tttcaaagta | gctgagcaag | ataatgaaag | gatcttgact | 360 |
| aagctaagaa | acaggatcga | tagagttggt | atcaaacttc | caactgttga | agtcaggtac | 420 |
| gagcatttga | cgattaaagc | tgattgttac | actggtaata | gatctcttcc | tacacttttg | 480 |
| aatgttgtga | ggaacatggg | agagtctgct | ttaggtatga | ttggtattca | atttgctaag | 540 |
| aaagctcagc | ttacgattct | taaagatatc | tctggggtta | ttaaacctgg | aaggatgaca | 600 |
| cttttgttgg | gtcctccttc | ttctggtaag | accactcttt | tgttggcttt | agctgggaaa | 660 |
| cttgataaat | ctctacaagt | cagtggtgat | attacttaca | atggttacca | actcgatgag | 720 |
| tttgttccga | gaaagacctc | tgcttacatt | agtcagaacg | atcttcatgt | tggtatcatg | 780 |
| actgttaagg | agactcttga | cttctctgct | aggtgtcaag | gtgttggtac | tcgttatgat | 840 |
| ctgttgaatg | agcttgcgag | gagagaaaag | gacgctggta | tattcccgga | agccgatgtt | 900 |
| gatctcttca | tgaaagcttc | tgctgctcaa | ggtgttaaga | acagtctcgt | cactgattat | 960 |
| actctcaaaa | ttttggggct | tgacatttgc | aaagacacaa | tagttggaga | tgacatgatg | 1020 |
| agaggtatat | ctggaggtca | gaagaaacgt | gtcacaactg | gtgagatgat | tgttggacct | 1080 |
| actaagacac | tcttcatgga | cgaaatatcc | actggtcttg | acagttccac | tacttttcaa | 1140 |
| atcgtcaagt | gtctgcaaca | aatcgttcac | ctcaatgaag | ccacggtgct | catgtctctc | 1200 |
| ctccagcctg | ctcctgagac | ttttgattta | ttcgatgata | tcatcttggt | gtcggaaggt | 1260 |
| cagatcgtgt | accaaggacc | gagagacaac | attcttgagt | tctttgagag | ctttgggttc | 1320 |
| aagtgtcctg | agagaaaagg | aacagctgat | ttcctgcaag | aggttacttc | caagaaagat | 1380 |
| caagaacagt | actgggtgaa | cccgaacaga | ccttatcact | acattccggt | tcagagtttt | 1440 |
| gccagtagat | acaagagttt | ccatgttggg | acgaagatgt | ctaacgaact | tgcagtaccg | 1500 |
| ttcgataagt | ctcgcggcca | caaagcagct | cttgtgttcg | ataagtactc | tgtctcaaag | 1560 |
| agggagcttc | tcaagagctg | ttgggacaaa | gagtggctgc | ttatgcagcg | aaacgcgttc | 1620 |
| ttctatgttt | tcaagactgt | ccagatcgtc | atcattgctg | caatcacgtc | tacactcttc | 1680 |
| ctgagaaccg | aaatgaacac | aagaaacgag | ggtgatgcta | atctctacat | aggagcattg | 1740 |
| ctatttggaa | tgatcatcaa | catgtttaat | gggtttgcgg | agatggctat | gatggtttca | 1800 |
| agactccctg | tgttctacaa | acagagggat | ctccttgtttt | atccatcctg | gaccttctca | 1860 |
| cttcccactt | tcttgcttgg | gattccaagc | tcaatattag | aatcgacggc | ttggatggtg | 1920 |
| gtgacttatt | actccattgg | ttttgcacct | gacgccagcc | gcttcttcaa | gcagtttctt | 1980 |
| ctggtgtttc | tgattcaaca | aatggctgca | tccctctttta | ggttgattgc | ttctgtgtgc | 2040 |
| agaaccatga | tgattgctaa | tactggtggt | gctctcactc | tacttcttgt | gttcttgctc | 2100 |
| ggaggcttcc | ttcttccgaa | aggcaagatt | cctgactggt | ggggttgggc | ttactgggta | 2160 |

```
tctcctctca cctatgcttt caacggtcta gtagtcaatg aaatgtttgc tcccagatgg    2220
atgaacaaaa tggcttcttc taacagcaca ataaagcttg aactatggt gcttaatact     2280 tgggatgtct accatcaaaa gaactggtac tggatttcag ttggagcctt gctttgtttc    2340
acagccctct tcaacattct attcaccttg gcacttacct atctcaaccc tcttgggaag    2400
aaggcaggtt tacttccaga agaagaaaat gaagacgctg atcagggaa agatccaatg     2460 cgtagatctt tgtctactgc agatgggaac agaagaggag aggtcgcaat ggggagaatg    2520
agtagggact ctgcggctga agcatcaggt ggtgcaggca ataagaaagg aatggttctt    2580
cctttcactc ctttagctat gtcctttgac gacgtcaaat actttgttga catgcctggg    2640
gaaatgagag accaaggagt tacagaaaca agactccaac tgcttaaagg tgtgactggt    2700
gcatttaggc caggagtttt gactgcgctt atgggagtga gtggtgccgg taagactacg    2760
cttatggacg tttggccgg aaggaaaaca ggtggataca ttgaaggaga tgtgagaata    2820
tcaggattcc caaggttca agaaacattt gctagaatct caggatattg tgagcagacc    2880
gatattcact ccccgcaagt aacagtcaga gaatctctga ttttctctgc tttccttcgt    2940
cttcctaaag aagtcggcaa agatgaaaaa atgatgtttg tggatcaagt gatggaattg    3000
gtagagctgg acagtcttag ggactccatt gttggtttac cgggtgtcac ggggctttcc    3060
acggagcaga gaaagagact gacaatcgcg gtggagcttg tagccaaccc ttccatcatc    3120
tttatggatg agccaacttc agggctagac gctagagcag cggctattgt gatgagggcg    3180
gtaaggaaca cagtggacac tggaagaacc gtggtctgca ccattcatca gcctagcatt    3240
gatatctttg aagcatttga tgaattgatg ctgatgaaga gaggaggaca agtgatttac    3300
gcgggtccat tgggtcaaaa ctctcacaag gtggttgagt actttgaatc tttcccccgga    3360 gtgtccaaga ttcagaaaaa gtataacccg gccacttgga tgctcgaagc tagctcactc    3420
gccgctgagc taaagcttag tgttgacttt gctgagttat acaatcaatc agcattgcac    3480
cagcgaaaca aagcgttggt aaaagaacta agtgtaccac cagcaggagc atcagatctt    3540
tactttgcta cacaattctc acaaaacaca tggggacagt tcaaatcatg cttatggaaa    3600
caatggtgga cgtattggag atctccagac tacaatcttg tccgtttcat cttcacattg    3660
gcaacatctc tcttgattgg tacagtcttc tggcaaatcg gaggtaacag gtcgaacgca    3720
ggggatctaa caatggtgat aggagcattg tatgccgcga ttatcttcgt gggaatcaac    3780
aactgttcaa cagtacaacc gatggttgca gtggaaagaa cagtgttcta cagagaaaga    3840
gcagcaggaa tgtactcagc catgcccatat gccatctctc aagtcacttg tgagcttccc    3900
tatgtcctta ttcaaaccgt ttactactca ctcatcgtct acgccatggt tggtttcgaa    3960
tggaaagccg aaaagttctt ctggttcgtc ttcgttagct acttctcatt cctctactgg    4020
acttactacg gcatgatgac tgtttccctc acaccaaacc aacaagtcgc ttcgattttc    4080
gcctcagcgt tttacggtat tttcaacctc ttctctggtt tcttcattcc aagacccaaa    4140
atcccaaaat ggtggatttg gtactactgg atctgccctg ttgcatggac cgtgtatgga    4200
ttgatagtgt cgcagtacgg tgatgtggag acacgtatcc aagtccttgg tggtgctcct    4260
gacttaaccg tcaagcaata cattgaggac cattatggtt tccaatctga ctttatggga    4320
ccagtggcgt ctgtactcat cgctttcacc gtcttcttcg ccttcatctt cgccttctgc    4380
atcagaactc tcaacttcca gaccagataa                                     4410
```

<210> SEQ ID NO 4
<211> LENGTH: 1469

```
<212> TYPE: PRT
<213> ORGANISM: Arabidopsis thaliana

<400> SEQUENCE: 4

Met Asp Tyr Asn Pro Asn Leu Pro Pro Leu Gly Gly Gly Gly Val Ser
1               5                   10                  15

Met Arg Arg Ser Ile Ser Arg Ser Val Ser Arg Ala Ser Arg Asn Ile
            20                  25                  30

Glu Asp Ile Phe Ser Ser Gly Ser Arg Arg Thr Gln Ser Val Asn Asp
        35                  40                  45

Asp Glu Glu Ala Leu Lys Trp Ala Ala Ile Glu Lys Leu Pro Thr Tyr
    50                  55                  60

Ser Arg Leu Arg Thr Thr Leu Met Asn Ala Val Val Glu Asp Asp Val
65                  70                  75                  80

Tyr Gly Asn Gln Leu Met Ser Lys Glu Val Asp Val Thr Lys Leu Asp
                85                  90                  95

Gly Glu Asp Arg Gln Lys Phe Ile Asp Met Val Phe Lys Val Ala Glu
            100                 105                 110

Gln Asp Asn Glu Arg Ile Leu Thr Lys Leu Arg Asn Arg Ile Asp Arg
        115                 120                 125

Val Gly Ile Lys Leu Pro Thr Val Glu Val Arg Tyr Glu His Leu Thr
    130                 135                 140

Ile Lys Ala Asp Cys Tyr Thr Gly Asn Arg Ser Leu Pro Thr Leu Leu
145                 150                 155                 160

Asn Val Val Arg Asn Met Gly Glu Ser Ala Leu Gly Met Ile Gly Ile
                165                 170                 175

Gln Phe Ala Lys Lys Ala Gln Leu Thr Ile Leu Lys Asp Ile Ser Gly
            180                 185                 190

Val Ile Lys Pro Gly Arg Met Thr Leu Leu Leu Gly Pro Pro Ser Ser
    195                 200                 205

Gly Lys Thr Thr Leu Leu Ala Leu Ala Gly Lys Leu Asp Lys Ser
    210                 215                 220

Leu Gln Val Ser Gly Asp Ile Thr Tyr Asn Gly Tyr Gln Leu Asp Glu
225                 230                 235                 240

Phe Val Pro Arg Lys Thr Ser Ala Tyr Ile Ser Gln Asn Asp Leu His
                245                 250                 255

Val Gly Ile Met Thr Val Lys Glu Thr Leu Asp Phe Ser Ala Arg Cys
            260                 265                 270

Gln Gly Val Gly Thr Arg Tyr Asp Leu Leu Asn Glu Leu Ala Arg Arg
        275                 280                 285

Glu Lys Asp Ala Gly Ile Phe Pro Glu Ala Asp Val Asp Leu Phe Met
    290                 295                 300

Lys Ala Ser Ala Ala Gln Gly Val Lys Asn Ser Leu Val Thr Asp Tyr
305                 310                 315                 320

Thr Leu Lys Ile Leu Gly Leu Asp Ile Cys Lys Asp Thr Ile Val Gly
                325                 330                 335

Asp Asp Met Met Arg Gly Ile Ser Gly Gly Gln Lys Lys Arg Val Thr
            340                 345                 350

Thr Gly Glu Met Ile Val Gly Pro Thr Lys Thr Leu Phe Met Asp Glu
        355                 360                 365

Ile Ser Thr Gly Leu Asp Ser Ser Thr Thr Phe Gln Ile Val Lys Cys
    370                 375                 380

Leu Gln Gln Ile Val His Leu Asn Glu Ala Thr Val Leu Met Ser Leu
385                 390                 395                 400
```

-continued

```
Leu Gln Pro Ala Pro Glu Thr Phe Asp Leu Phe Asp Asp Ile Ile Leu
                405                 410                 415
Val Ser Glu Gly Gln Ile Val Tyr Gln Gly Pro Arg Asp Asn Ile Leu
                420                 425                 430
Glu Phe Phe Glu Ser Phe Gly Phe Lys Cys Pro Glu Arg Lys Gly Thr
                435                 440                 445
Ala Asp Phe Leu Gln Glu Val Thr Ser Lys Lys Asp Gln Glu Gln Tyr
                450                 455                 460
Trp Val Asn Pro Asn Arg Pro Tyr His Tyr Ile Pro Val Ser Glu Phe
465                 470                 475                 480
Ala Ser Arg Tyr Lys Ser Phe His Val Gly Thr Lys Met Ser Asn Glu
                485                 490                 495
Leu Ala Val Pro Phe Asp Lys Ser Arg Gly His Lys Ala Ala Leu Val
                500                 505                 510
Phe Asp Lys Tyr Ser Val Ser Lys Arg Glu Leu Leu Lys Ser Cys Trp
                515                 520                 525
Asp Lys Glu Trp Leu Leu Met Gln Arg Asn Ala Phe Phe Tyr Val Phe
                530                 535                 540
Lys Thr Val Gln Ile Val Ile Ile Ala Ala Ile Thr Ser Thr Leu Phe
545                 550                 555                 560
Leu Arg Thr Glu Met Asn Thr Arg Asn Glu Gly Asp Ala Asn Leu Tyr
                565                 570                 575
Ile Gly Ala Leu Leu Phe Gly Met Ile Ile Asn Met Phe Asn Gly Phe
                580                 585                 590
Ala Glu Met Ala Met Met Val Ser Arg Leu Pro Val Phe Tyr Lys Gln
                595                 600                 605
Arg Asp Leu Leu Phe Tyr Pro Ser Trp Thr Phe Ser Leu Pro Thr Phe
                610                 615                 620
Leu Leu Gly Ile Pro Ser Ser Ile Leu Glu Ser Thr Ala Trp Met Val
625                 630                 635                 640
Val Thr Tyr Tyr Ser Ile Gly Phe Ala Pro Asp Ala Ser Arg Phe Phe
                645                 650                 655
Lys Gln Phe Leu Leu Val Phe Leu Ile Gln Gln Met Ala Ala Ser Leu
                660                 665                 670
Phe Arg Leu Ile Ala Ser Val Cys Arg Thr Met Met Ile Ala Asn Thr
                675                 680                 685
Gly Gly Ala Leu Thr Leu Leu Leu Val Phe Leu Leu Gly Gly Phe Leu
                690                 695                 700
Leu Pro Lys Gly Lys Ile Pro Asp Trp Trp Gly Trp Ala Tyr Trp Val
705                 710                 715                 720
Ser Pro Leu Thr Tyr Ala Phe Asn Gly Leu Val Val Asn Glu Met Phe
                725                 730                 735
Ala Pro Arg Trp Met Asn Lys Met Ala Ser Ser Asn Ser Thr Ile Lys
                740                 745                 750
Leu Gly Thr Met Val Leu Asn Thr Trp Asp Val Tyr His Gln Lys Asn
                755                 760                 765
Trp Tyr Trp Ile Ser Val Gly Ala Leu Leu Cys Phe Thr Ala Leu Phe
                770                 775                 780
Asn Ile Leu Phe Thr Leu Ala Leu Thr Tyr Leu Asn Pro Leu Gly Lys
785                 790                 795                 800
Lys Ala Gly Leu Leu Pro Glu Glu Glu Asn Glu Asp Ala Asp Gln Gly
                805                 810                 815
```

-continued

```
Lys Asp Pro Met Arg Arg Ser Leu Ser Thr Ala Asp Gly Asn Arg Arg
            820                 825                 830

Gly Glu Val Ala Met Gly Arg Met Ser Arg Asp Ser Ala Ala Glu Ala
            835                 840                 845

Ser Gly Gly Ala Gly Asn Lys Lys Gly Met Val Leu Pro Phe Thr Pro
    850                 855                 860

Leu Ala Met Ser Phe Asp Asp Val Lys Tyr Phe Val Asp Met Pro Gly
865                 870                 875                 880

Glu Met Arg Asp Gln Gly Val Thr Glu Thr Arg Leu Gln Leu Leu Lys
                885                 890                 895

Gly Val Thr Gly Ala Phe Arg Pro Gly Val Leu Thr Ala Leu Met Gly
            900                 905                 910

Val Ser Gly Ala Gly Lys Thr Thr Leu Met Asp Val Leu Ala Gly Arg
            915                 920                 925

Lys Thr Gly Gly Tyr Ile Glu Gly Asp Val Arg Ile Ser Gly Phe Pro
    930                 935                 940

Lys Val Gln Glu Thr Phe Ala Arg Ile Ser Gly Tyr Cys Glu Gln Thr
945                 950                 955                 960

Asp Ile His Ser Pro Gln Val Thr Val Arg Glu Ser Leu Ile Phe Ser
                965                 970                 975

Ala Phe Leu Arg Leu Pro Lys Glu Val Gly Lys Asp Glu Lys Met Met
            980                 985                 990

Phe Val Asp Gln Val Met Glu Leu Val Glu Leu Asp Ser Leu Arg Asp
        995                 1000                1005

Ser Ile Val Gly Leu Pro Gly Val Thr Gly Leu Ser Thr Glu Gln
    1010                1015                1020

Arg Lys Arg Leu Thr Ile Ala Val Glu Leu Val Ala Asn Pro Ser
    1025                1030                1035

Ile Ile Phe Met Asp Glu Pro Thr Ser Gly Leu Asp Ala Arg Ala
    1040                1045                1050

Ala Ala Ile Val Met Arg Ala Val Arg Asn Thr Val Asp Thr Gly
    1055                1060                1065

Arg Thr Val Val Cys Thr Ile His Gln Pro Ser Ile Asp Ile Phe
    1070                1075                1080

Glu Ala Phe Asp Glu Leu Met Leu Met Lys Arg Gly Gly Gln Val
    1085                1090                1095

Ile Tyr Ala Gly Pro Leu Gly Gln Asn Ser His Lys Val Val Glu
    1100                1105                1110

Tyr Phe Glu Ser Phe Pro Gly Val Ser Lys Ile Pro Glu Lys Tyr
    1115                1120                1125

Asn Pro Ala Thr Trp Met Leu Glu Ala Ser Ser Leu Ala Ala Glu
    1130                1135                1140

Leu Lys Leu Ser Val Asp Phe Ala Glu Leu Tyr Asn Gln Ser Ala
    1145                1150                1155

Leu His Gln Arg Asn Lys Ala Leu Val Lys Glu Leu Ser Val Pro
    1160                1165                1170

Pro Ala Gly Ala Ser Asp Leu Tyr Phe Ala Thr Gln Phe Ser Gln
    1175                1180                1185

Asn Thr Trp Gly Gln Phe Lys Ser Cys Leu Trp Lys Gln Trp Trp
    1190                1195                1200

Thr Tyr Trp Arg Ser Pro Asp Tyr Asn Leu Val Arg Phe Ile Phe
    1205                1210                1215

Thr Leu Ala Thr Ser Leu Leu Ile Gly Thr Val Phe Trp Gln Ile
```

|      |      |      |
|------|------|------|
| 1220 | 1225 | 1230 |

Gly Gly Asn Arg Ser Asn Ala Gly Asp Leu Thr Met Val Ile Gly
    1235                1240                1245

Ala Leu Tyr Ala Ala Ile Ile Phe Val Gly Ile Asn Asn Cys Ser
    1250                1255                1260

Thr Val Gln Pro Met Val Ala Val Glu Arg Thr Val Phe Tyr Arg
    1265                1270                1275

Glu Arg Ala Ala Gly Met Tyr Ser Ala Met Pro Tyr Ala Ile Ser
    1280                1285                1290

Gln Val Thr Cys Glu Leu Pro Tyr Val Leu Ile Gln Thr Val Tyr
    1295                1300                1305

Tyr Ser Leu Ile Val Tyr Ala Met Val Gly Phe Glu Trp Lys Ala
    1310                1315                1320

Glu Lys Phe Phe Trp Phe Val Phe Val Ser Tyr Phe Ser Phe Leu
    1325                1330                1335

Tyr Trp Thr Tyr Tyr Gly Met Met Thr Val Ser Leu Thr Pro Asn
    1340                1345                1350

Gln Gln Val Ala Ser Ile Phe Ala Ser Ala Phe Tyr Gly Ile Phe
    1355                1360                1365

Asn Leu Phe Ser Gly Phe Phe Ile Pro Arg Pro Lys Ile Pro Lys
    1370                1375                1380

Trp Trp Ile Trp Tyr Tyr Trp Ile Cys Pro Val Ala Trp Thr Val
    1385                1390                1395

Tyr Gly Leu Ile Val Ser Gln Tyr Gly Asp Val Glu Thr Arg Ile
    1400                1405                1410

Gln Val Leu Gly Gly Ala Pro Asp Leu Thr Val Lys Gln Tyr Ile
    1415                1420                1425

Glu Asp His Tyr Gly Phe Gln Ser Asp Phe Met Gly Pro Val Ala
    1430                1435                1440

Ala Val Leu Ile Ala Phe Thr Val Phe Phe Ala Phe Ile Phe Ala
    1445                1450                1455

Phe Cys Ile Arg Thr Leu Asn Phe Gln Thr Arg
    1460                1465

<210> SEQ ID NO 5
<211> LENGTH: 588
<212> TYPE: DNA
<213> ORGANISM: Arabidopsis thaliana

<400> SEQUENCE: 5

```
atggcgtcaa ggtttataaa gtgtgtgacc gtcggagatg gtgccgtcgg aaaaacttgc      60
atgctcattt cttacactag caatactttt cctactgatt atgtgccaac tgttttcgac     120
aacttcagtg ctaatgtggt tgttgatgga acactgtca atcttggatt gtgggatact      180
gctggtcaag aggactacaa caggttacga cctttgagtt accgtggtgc tgatgttttc     240
attcttgctt tctctcttat tagcaaggct agctatgaga atatagccaa gaagtggatt     300
cctgagctca ggcattatgc tcctggtgtt cccattatcc ttgttgggac aaaactcgct     360
cttcgagatg acaagcaatt ctttatagat catcctggtg ctgtgccaat tactacaaac     420
cagggagagg aactgaagaa actgattgga tctgctgtct acattgaatg tagttcaaag     480
acacagcaga acgtgaaggc agtgtttgat gcagctataa aagtggtgct tcagccacca     540
aagcagaaga agaagaaaaa gaataagaac cgttgcgcgt tcttgtga                  588
```

```
<210> SEQ ID NO 6
<211> LENGTH: 195
<212> TYPE: PRT
<213> ORGANISM: Arabidopsis thaliana

<400> SEQUENCE: 6

Met Ala Ser Arg Phe Ile Lys Cys Val Thr Val Gly Asp Gly Ala Val
1               5                   10                  15

Gly Lys Thr Cys Met Leu Ile Ser Tyr Thr Ser Asn Thr Phe Pro Thr
            20                  25                  30

Asp Tyr Val Pro Thr Val Phe Asp Asn Phe Ser Ala Asn Val Val Val
        35                  40                  45

Asp Gly Asn Thr Val Asn Leu Gly Leu Trp Asp Thr Ala Gly Gln Glu
    50                  55                  60

Asp Tyr Asn Arg Leu Arg Pro Leu Ser Tyr Arg Gly Ala Asp Val Phe
65                  70                  75                  80

Ile Leu Ala Phe Ser Leu Ile Ser Lys Ala Ser Tyr Glu Asn Ile Ala
                85                  90                  95

Lys Lys Trp Ile Pro Glu Leu Arg His Tyr Ala Pro Gly Val Pro Ile
            100                 105                 110

Ile Leu Val Gly Thr Lys Leu Ala Leu Arg Asp Asp Lys Gln Phe Phe
        115                 120                 125

Ile Asp His Pro Gly Ala Val Pro Ile Thr Thr Asn Gln Gly Glu Glu
    130                 135                 140

Leu Lys Lys Leu Ile Gly Ser Ala Val Tyr Ile Glu Cys Ser Ser Lys
145                 150                 155                 160

Thr Gln Gln Asn Val Lys Ala Val Phe Asp Ala Ala Ile Lys Val Val
                165                 170                 175

Leu Gln Pro Pro Lys Gln Lys Lys Lys Lys Asn Lys Asn Arg Cys
            180                 185                 190

Ala Phe Leu
        195

<210> SEQ ID NO 7
<211> LENGTH: 46
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: AtPDR8F-SB

<400> SEQUENCE: 7
tcccccgggg gcgcggatcc gcgatggatt acaatccaaa tcttcc                46

<210> SEQ ID NO 8
<211> LENGTH: 43
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: AtPDR8R-PX

<400> SEQUENCE: 8
gacacgtgct ccgctcgagc ggttatctgg tctggaagtt gag                   43

<210> SEQ ID NO 9
<211> LENGTH: 31
```

```
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: TM/GFP-F

<400> SEQUENCE: 9
aagaagctta tggagtgtgg tggcgtctcc g                              31

<210> SEQ ID NO 10
<211> LENGTH: 31
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: TM/GFP-R

<400> SEQUENCE: 10
tagaagctta gaactacact acagagctgc t                              31

<210> SEQ ID NO 11
<211> LENGTH: 26
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: TaTM20 RTF

<400> SEQUENCE: 11
aagggttgct cctcttcgcg atcttg                                    26

<210> SEQ ID NO 12
<211> LENGTH: 25
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: TaTM20 RTR

<400> SEQUENCE: 12
gtacatgcca gcaccgtatg gattg                                     25

<210> SEQ ID NO 13
<211> LENGTH: 23
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: TaG3PDHF

<400> SEQUENCE: 13
caacgctagc tgcaccacta act                                       23

<210> SEQ ID NO 14
<211> LENGTH: 22
<212> TYPE: DNA
<213> ORGANISM: Artificial Sequence
<220> FEATURE:
<223> OTHER INFORMATION: Synthetic primer
```

```
<220> FEATURE:
<221> NAME/KEY: misc_feature
<223> OTHER INFORMATION: TaG3PDHR

<400> SEQUENCE: 14
actcctcctt gatagcagcc tt                                              22

<210> SEQ ID NO 15
<211> LENGTH: 23
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: AtPDR8-RTF

<400> SEQUENCE: 15
ctcttgattg gtacagtctt ctg                                             23

<210> SEQ ID NO 16
<211> LENGTH: 24
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: AtPDR8 RTR

<400> SEQUENCE: 16
ccataatggt cctcaatgta ttgc                                            24

<210> SEQ ID NO 17
<211> LENGTH: 20
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Tub-F

<400> SEQUENCE: 17
gctgacgttt tctgtattcc                                                 20

<210> SEQ ID NO 18
<211> LENGTH: 18
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Tub-R

<400> SEQUENCE: 18
aggctctgta ttgctgtg                                                   18

<210> SEQ ID NO 19
<211> LENGTH: 29
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Rop2-forward
```

<400> SEQUENCE: 19
ccgatcttgc ggcagagatg gcgtcaagg                                29

<210> SEQ ID NO 20
<211> LENGTH: 32
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Rop2-reverse

<400> SEQUENCE: 20
cttatcacaa gaacgcgcaa cggttcttat tc                            32

<210> SEQ ID NO 21
<211> LENGTH: 29
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Actin2-forward

<400> SEQUENCE: 21
ggccgatggt gaggatattc agccacttg                                29

<210> SEQ ID NO 22
<211> LENGTH: 29
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Actin2-reverse

<400> SEQUENCE: 22
tcgatggacc tgactcatcg tactcactc                                29

<210> SEQ ID NO 23
<211> LENGTH: 20
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: PDR8NF

<400> SEQUENCE: 23
agccttgctt tgtttcacag                                          20

<210> SEQ ID NO 24
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: PDR8NR

<400> SEQUENCE: 24
ccctactcat tctccccatt g                                        21

-continued

```
<210> SEQ ID NO 25
<211> LENGTH: 34
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: P8RI-XK

<400> SEQUENCE: 25
ccgctcgagc gggatgcctt gctttgtttc acag                                  34

<210> SEQ ID NO 26
<211> LENGTH: 31
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: P8RI-BX

<400> SEQUENCE: 26
ggggtacccc ccctactcat tctccccatt g                                     31

<210> SEQ ID NO 27
<211> LENGTH: 200
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: TM1-4

<400> SEQUENCE: 27
```

| | | | | | | | | | | | | | | | |
|---|---|---|---|---|---|---|---|---|---|---|---|---|---|---|---|
| Met | Glu | Cys | Gly | Gly | Val | Ser | Ala | Val | Gln | Val | Gln | Pro | Ala | Val | His |
| 1 | | | | 5 | | | | | 10 | | | | | 15 | |
| Met | Gly | Gln | Pro | Gly | Gln | Pro | Ala | Lys | Pro | Pro | Val | Gln | Pro | Trp | Glu |
| | | | 20 | | | | | 25 | | | | | 30 | | |
| Tyr | Ser | Leu | Arg | Lys | Tyr | Leu | Leu | Leu | Ala | Ala | Leu | Val | Val | Thr | |
| | | | 35 | | | | 40 | | | | | 45 | | | |
| Val | Thr | Tyr | Ala | Ala | Gly | Phe | Ser | Pro | Pro | Gly | Gly | Val | Trp | Gln | Ala |
| | 50 | | | | | 55 | | | | | 60 | | | | |
| Ala | His | Asp | Gly | Gln | Pro | Ala | Gly | Asp | Pro | Ile | Ile | Arg | Gly | Thr | His |
| 65 | | | | | 70 | | | | | 75 | | | | | 80 |
| Tyr | Arg | Arg | Tyr | Leu | Ala | Phe | Phe | Tyr | Cys | Asn | Ala | Thr | Ala | Phe | Ala |
| | | | | 85 | | | | | 90 | | | | | 95 | |
| Ala | Ser | Leu | Val | Val | Ile | Val | Leu | Ile | Leu | Ile | Leu | Ala | Val | Arg | His |
| | | | 100 | | | | | 105 | | | | | 110 | | |
| Asp | Lys | Lys | Gly | Lys | Asp | Ser | Arg | Trp | Val | Val | Pro | Leu | Arg | Leu | |
| | | | 115 | | | | | 120 | | | | | 125 | | |
| Val | Met | Val | Leu | Asp | Leu | Leu | Ser | Leu | Met | Gly | Ala | Tyr | Gly | Ala | Gly |
| | 130 | | | | | 135 | | | | | 140 | | | | |
| Thr | Cys | Gln | Asp | Lys | Ile | Ser | Ile | Val | Tyr | Ser | Ala | Val | Leu | Val | Ala |
| 145 | | | | | 150 | | | | | 155 | | | | | 160 |
| Ala | Val | Phe | Leu | Tyr | Val | Ala | Val | Leu | Lys | Met | Met | Asp | Trp | Trp | Cys |
| | | | | 165 | | | | | 170 | | | | | 175 | |
| Pro | Asp | Asn | Lys | Thr | Gly | Pro | Gly | Cys | Asp | Gly | Thr | Met | Ser | Ser | Ala |
| | | | 180 | | | | | 185 | | | | | 190 | | |

-continued

Pro Asn Ser Asn Ser Asn Ser Gly
        195                 200

<210> SEQ ID NO 28
<211> LENGTH: 200
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: TM5-8

<400> SEQUENCE: 28

Asp Val Met Ser Thr Pro Asp Pro Ser Asp Ala Val Thr Ile Pro
1               5                   10                  15

Ser Pro Leu Arg Asp Ser Asp Pro Asn Val Lys Glu Glu Asp Arg
                20                  25                  30

Lys Arg Glu Ala Leu Lys Lys Leu Lys Ala Asn Glu Arg Leu Arg Lys
            35                  40                  45

Val Leu Met Leu Leu Ala Thr Phe Ala Val Ser Ile Thr Tyr Val Ala
        50                  55                  60

Gly Leu Ser Met Pro Gly Gly Phe Trp Asp Ser Thr Gly Thr Ser Tyr
65                  70                  75                  80

Arg Pro Gly Asp Ala Ile Leu Lys Asp Arg His Arg Pro Arg Leu Thr
                85                  90                  95

Ala Phe Leu Leu Cys Asn Thr Thr Ser Phe Val Ala Ser Leu Leu Ile
            100                 105                 110

Ile Met Leu Leu Ile Ile Asp Gly Lys Lys Leu Arg Asp Lys Lys Ala
        115                 120                 125

Arg Ser Leu Val Leu Tyr Gly Phe Ile Val Val Ala Leu Val Ser Leu
    130                 135                 140

Val Gly Ala Tyr Thr Ala Gly Ser Cys Arg Glu Thr Lys Thr Thr Ile
145                 150                 155                 160

Tyr Val Val Ser Leu Thr Gly Gly Ile Leu Ala Met Ala Tyr Ile Leu
                165                 170                 175

Leu Tyr Ala Phe Tyr Thr Leu Lys Ser Ser Arg Ser Ser Pro Thr Gln
            180                 185                 190

Pro Thr Asp Ala Leu Gln Gln Thr
        195                 200

<210> SEQ ID NO 29
<211> LENGTH: 150
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: TM9-12

<400> SEQUENCE: 29

Thr Asp Asn Val Ser Ala Arg Lys Gly Leu Asp Lys Ala Arg Ser Leu
1               5                   10                  15

Val Leu Leu Leu Ala Thr Leu Ala Ala Thr Ile Thr Tyr Thr Ala Gly
            20                  25                  30

Leu Asp Pro Pro Gly Gly Leu Trp Gln Asp Lys Gly Asp Gly Tyr Ile
        35                  40                  45

Ala Gly Asp Pro Ile Leu Ile Thr Thr Asn Ile Arg Arg Tyr Arg Ala
    50                  55                  60

```
Phe Tyr Tyr Cys Asn Ser Val Ala Phe Val Ala Ser Leu Leu Val Ile
 65                  70                  75                  80

Val Leu Val Gln Thr Glu Arg Leu Ile Lys His His Val Leu Glu Ala
                 85                  90                  95

Ala Met Ile Leu Asp Leu Phe Gly Leu Ile Gly Ala Tyr Ala Ala Gly
            100                 105                 110

Ser Cys Arg Asn Val Asn Ser Val Tyr Val Met Ala Leu Ala Gly
            115                 120                 125

Ala Ala Leu Ile Tyr Val Val Ile His Ile Val Phe Phe Thr Leu Glu
            130                 135                 140

Leu Asp Gln Lys Asp Lys
145                 150

<210> SEQ ID NO 30
<211> LENGTH: 172
<212> TYPE: PRT
<213> ORGANISM: Artificial Sequence
<220> FEATURE:
<223> OTHER INFORMATION: Synthetic polypeptide

<400> SEQUENCE: 30

Lys Asp Asp Asp Gln Glu Asp Glu Leu Leu Glu Lys Arg Arg Lys Arg
  1               5                  10                  15

Leu Leu Leu Phe Ala Ile Leu Ala Ala Thr Ile Thr Tyr Gln Ala Gly
                 20                  25                  30

Leu Thr Pro Pro Gly Gly Phe Leu Leu Gln Asp Thr Leu Gly His
            35                  40                  45

His Ala Gly Asp Pro Ile Leu Leu His Asn Tyr Pro Val Arg Tyr His
     50                  55                  60

Ala Phe Phe Tyr Cys Asn Ser Val Ser Phe Met Leu Ser Ile Ala Leu
 65                  70                  75                  80

Ile Ile Leu Leu Val Asn Pro Asn Leu Tyr Arg Pro Ala Ile Gln Ser
                 85                  90                  95

Asn Ala Leu Ser Val Cys Thr Ala Val Gly Leu Phe Cys Leu Met Gly
            100                 105                 110

Ala Tyr Ala Ala Gly Ser Thr Gln His Arg Lys Thr Ser Ile Tyr Ile
            115                 120                 125

Phe Val Leu Val Ala Val Val Leu Leu Val Ala Ala Gly Leu Leu Leu
130                 135                 140

Val Phe Leu Leu Lys Arg Lys Leu Ser Asn Ala Val Val Ser Pro Pro
145                 150                 155                 160

Arg Glu Gln Asn Glu Glu Glu Arg Lys Glu Val Glu
                165                 170

<210> SEQ ID NO 31
<211> LENGTH: 167
<212> TYPE: PRT
<213> ORGANISM: Artificial Sequence
<220> FEATURE:
<223> OTHER INFORMATION: Synthetic polypeptide

<400> SEQUENCE: 31

Glu Lys Asn Glu Asp Glu Glu Glu Ala Lys Lys His Ala Arg Arg Lys
  1               5                  10                  15

Tyr Leu Met Leu Leu Gly Ile Leu Val Ala Ser Val Ala Tyr Gln Ala
                 20                  25                  30

Gly Leu Glu Pro Pro Gly Gly Ala Trp Gln Asn Asn Asp Asn Gly Tyr
```

-continued

```
                35                  40                  45
Glu Ala Gly Asn Pro Val Met Asn Asp Asn Arg Arg Pro Arg Tyr Leu
    50                  55                  60

Thr Phe Phe Tyr Ser Asn Ser Val Ser Phe Val Ala Ser Ile Val Val
65                  70                  75                  80

Ile Ile Met Leu Leu Pro Gln Trp Leu Pro Lys Lys Lys Glu Gly Glu
                85                  90                  95

Trp Glu Lys Trp Ser Leu Arg Val Met Asn Trp Met Ile Arg Leu Asp
                100                 105                 110

Leu Phe Ala Leu Leu Val Ala Tyr Ala Ala Gly Ser Asn Arg Gly Leu
                115                 120                 125

Lys Thr Ser Leu Tyr Val Val Ala Leu Ile Phe Ala Val Leu Gly Tyr
        130                 135                 140

Phe Ala Ile His Thr Val Leu Ala Cys Thr Val Cys Arg His Glu Arg
145                 150                 155                 160

Arg Gln Ser Ser Ser Val Val
                165
```